US006083712A

United States Patent [19]

Birch et al.

[11] Patent Number: 6,083,712

[45] Date of Patent: Jul. 4, 2000

[54] BIOTECHNOLOGICAL METHOD OF PRODUCING BIOTIN

[75] Inventors: Olwen Birch, Naters; Johann Brass, Ausserberg; Martin Fuhrmann; Nicholas Shaw, both of Visp, all of Switzerland

[73] Assignee: Lonza A.G., Basel, Switzerland

[21] Appl. No.: 08/411,768

[22] PCT Filed: Oct. 1, 1993

[86] PCT No.: PCT/EP93/02688

§ 371 Date: Jun. 8, 1995

§ 102(e) Date: Jun. 8, 1995

[87] PCT Pub. No.: WO94/08023

PCT Pub. Date: Apr. 14, 1994

[30] Foreign Application Priority Data

| | | | |
|---|---|---|---|
| Oct. 2, 1992 | [CH] | Switzerland | 3124/92 |
| Jul. 15, 1993 | [CH] | Switzerland | 2134/93 |

[51] Int. Cl.[7] .......... C12P 21/06; C12N 15/00; C07H 17/00

[52] U.S. Cl. .......... 435/69.1; 435/320.1; 435/252.3; 435/252.33; 536/23.1

[58] Field of Search .......... 435/119, 252.2, 435/252.33, 243, 320.1, 69.1, 252.3; 536/24.1, 23.7, 23.1

[56] References Cited

U.S. PATENT DOCUMENTS

| | | | |
|---|---|---|---|
| 5,096,823 | 3/1992 | Gloeckler et al. | 435/252.31 |
| 5,110,731 | 5/1992 | Fisher | 435/119 |
| 5,445,952 | 8/1995 | Campbell et al. | 435/121 |
| 5,494,816 | 2/1996 | Murdock | 435/183 |

FOREIGN PATENT DOCUMENTS

| | | |
|---|---|---|
| 0266240 | 5/1988 | European Pat. Off. . |
| 0316229 | 5/1989 | European Pat. Off. . |
| 0449724 | 10/1991 | European Pat. Off. . |
| 2216530 | 10/1989 | United Kingdom . |
| 8701391 | 3/1987 | WIPO . |

OTHER PUBLICATIONS

Alvares–Morales et al. Activation of the *Bradyrhizobium japonicum* nifH and nifDK operons is dependent on promoter–upstream DNA sequences. Nucleic Acid Research. vol. 14, No. 10, pp. 4207–4227, 1986.

Das et al. A ribosome binding site sequence is necessary for efficient expression of the distal gene of a translationally–coupled gene pair. Nucleic Acids Research. vol. 12, No. 11, pp. 4757–4768, 1984.

D. Shiuan et al., "Transcriptional regulation and gene arrangement of *Escherichia coli, Citrobacter freundii* and *Salmonella typhimurium* biotin operons", *Gene,* vol. 67 (1988), pp. 203–211.

Y. Izumi et al., "Characterization of biotin biosynthetic enzymes of *Bacillus sphaericus:* a dethobiotin producing bacterium", *Agric. Biol. Chem.* vol. 45, No. 9 (1981), pp. 1983–1989.

O. Ifuku et al., "Conversion of dethobiotin to biotin in cell–free extracts of *Escherichia coli", Bioscience Biotechnology Biochemistry,* vol. 56, No. 11 (1992), pp. 1780–1785.

A. Fujisawa et al., "Bioconversion of dethobiotin to biotin by a cell–free system of a bio YB transformant of *Bacillus sphaericus"FEMS Microbiol. Letters,* vol. 110 (1993), pp. 1–4.

C.K. Das Gupta et al, "Isolation and Characterization of the Biotin Genes of *Escherichia coli* K–12", *Gene 1* (1977) 331–345.

Anthony J. Otsuka et al., "The *Escherichia coli* Biotin Biosynthetic Enzyme Sequences . . . ", *J. Biolog. Chem. 263* (1988) 19577–19585.

*Primary Examiner*—Karen Cochrane Carlson
*Attorney, Agent, or Firm*—Baker & Botts, L.L.P.

[57] ABSTRACT

In DNA fragments and plasmids comprising the bioB, bioF, bioC, bioD and bioA genes responsible for biosynthesis of biotin, or their functionally equivalent genetic variants and mutants from enteric bacteria, the genes are arranged in a transcription unit. These DNA fragments and plasmids can be contained in microorganisms which can be used to produce biotin.

30 Claims, 16 Drawing Sheets

FROM FIG.2A
pB027
7.5kb
BamHI
fill-in dCTP
mbn
pB028
7.5kb
SalI
rabn
SnaI
Fragment 6.7kb
pB030
9.5kb
FROM FIG.2A
M13mp18
7.25kb
FROM FIG.2A
BanI
KpnI
Fragment 4.4kb
BamHI
KpnI
M13bio18
11.6kb
NcoI
BalBI
XbaI
fill-in
M13bio18/13
9.3kb
SalI
SphI
M13bioDA
10.3kb
EcoRI
fill-in
SnaI
Fragment 2.8kb
FROM FIG.2A
SphI
SalI
Fragment 0.97kb

```
     HindIII                  HindII
1  5'-AAGCTTACTCCCCATCCCCCTGTTGACAATTAATCATCGGCTCGTATAATGTGTGGAATT
                               -35        ptac       -10      +1

                                              KpnI  SauI   SpeI  bioB
61    GTGAGCGGATAACAATTTCACACAGGAAACAGGATCGGTACCTAAGGAGACTAGTCATGG
                                                     SD          METAla

121   CTCACCGCCCACGCTGGACATTGTCGCAAGTCACAGAATTATTTGAAAAACCGTTGCTGG
        HisArgProArgTrpThrLeuSerGlnValThrGluLeuPheGluLysProLeuLeuAsp

181   ATCTGCTGTTTGAAGCGCAGCAGGTGCATCGCCAGCATTTCGATCCTCGTCAGGTGCAGG
        LeuLeuPheGluAlaGlnGlnValHisArgGlnHisPheAspProArgGlnValGlnVal

241   TCAGCACGTTGCTGTCGATTAAGACCGGAGCTTGTCCGGAAGATTGCAAATACTGCCCGC
        SerThrLeuLeuSerIleLysThrGlyAlaCysProGluAspCysLysTyrCysProGln

301   AAAGCTCGCGCTACAAAACCGGGCTGGAAGCCGAGCGGTTGATGGAAGTTGAACAGGTGC
        SerSerArgTyrLysThrGlyLeuGluAlaGluArgLeuMETGluValGluGlnValLeu

             BssHII
361   TGGAGTCGGCGCGCAAAGCGAAAGCGGCAGGATCGACGCGCTTCTGTATGGGCGCGGCGT
        GluSerAlaArgLysAlaLysAlaAlaGlySerThrArgPheCysMETGlyAlaAlaTrp

421   GGAAGAATCCCCACGAACGCGATATGCCGTACCTGGAACAAATGGTGCAGGGGGTAAAAG
        LysAsnProHisGluArgAspMETProTyrLeuGluGlnMETValGlnGlyValLysAla

481   CGATGGGGCTGGAGGCGTGTATGACGCTGGGCACGTTGAGTGAATCTCAGGCGCAGCGCC
        METGlyLeuGluAlaCysMETThrLeuGlyThrLeuSerGluSerGlnAlaGlnArgLeu
      NruI
541   TCGCGAACGCCGGGCTGGATTACTACAACCACAACCTGGACACCTCGCCGGAGTTTTACG
        AlaAsnAlaGlyLeuAspTyrTyrAsnHisAsnLeuAspThrSerProGluPheTyrGly

601   GCAATATCATCACCACACGCACTTATCAGGAACGCCTCGATACGCTGGAAAAAGTGCGCG
        AsnIleIleThrThrArgThrTyrGlnGluArgLeuAspThrLeuGluLysValArgAsp

661   ATGCCGGGATCAAAGTCTGTTCTGGCGGCATTGTGGGCTTAGGCGAAACGGTAAAAGATC
        AlaGlyIleLysValCysSerGlyGlyIleValGlyLeuGlyGluThrValLysAspArg

721   GCGCCGGATTATTGCTGCAACTGGCAAACCTGCCGACGCCGCCGGAAAGCGTGCCAATCA
        AlaGlyLeuLeuLeuGlnLeuAlaAsnLeuProThrProProGluSerValProIleAsn

781   ACATGCTGGTGAAGGTGAAAGGCACGCCGCTTGCCGATAACGATGATGTCGATGCCTTTG
        METLeuValLysValLysGlyThrProLeuAlaAspAsnAspAspValAspAlaPheAsp
```

FIG.6A

```
                                        (BspHI)
841   ATTTTATTCGCACCATTGCGGTCGCGCGGATCATGATGCCAACCTCTTACGTGCGCCTTT
        PheIleArgThrIleAlaValAlaArgIleMETMETProThrSerTyrValArgLeuSer

901   CTGCCGGACGCGAGCAGATGAACGAACAGACTCAGGCGATGTGCTTTATGGCAGGCGCAA
        AlaGlyArgGluGlnMETAsnGluGlnThrGlnAlaMETCysPheMETAlaGlyAlaAsn

961   ACTCGATTTTCTACGGTTGCAAACTGCTGACCACGCCGAATCCGGAAGAAGATAAAGACC
        SerIlePheTyrGlyCysLysLeuLeuThrThrProAsnProGluGluAspLysAspLeu

1021  TGCAACTGTTCCGCAAACTGGGGCTAAATCCGCAGCAAACTGCCGTGCTGGCAGGGGATA
        GlnLeuPheArgLysLeuGlyLeuAsnProGlnGlnThrAlaValLeuAlaGlyAspAsn

                                                          SspI
1081  ACGAACAACAGCAACGTCTTGAACAGGCGCTGATGACCCCGGACACCGACGAATATTACA
        GluGlnGlnGlnArgLeuGluGlnAlaLeuMETThrProAspThrAspGluTyrTyrAsn

                 bioF
1141  ACGCGGCAGCATTATGAGCTGGCAGGAGAAAATCAACGCGGCGCTCGATGCGCGGCGTGC
        SD            METSerTrpGlnGluLysIleAsnAlaAlaLeuAspAlaArgArgAla
        AlaAlaAlaLeu***

1201  TGCCGATGCCCTGCGTCGCCGTTATCCGGTGGCGCAAGGAGCCGGACGCTGGCTGGTGGC
       AlaAspAlaLeuArgArgArgTyrProValAlaGlnGlyAlaGlyArgTrpLeuValAla

1261  GGATGATCGCCAGTATCTGAACTTTTCCAGTAACGATTATTTAGGTTTAAGCCATCATCC
       AspAspArgGlnTyrLeuAsnPheSerSerAsnAspTyrLeuGlyLeuSerHisHisPro

1321  GCAAATTATCCGTGCCTGGCAGCAGGGGGCGGAGCAATTTGGCATCGGTAGCGGCGGCTC
       GlnIleIleArgAlaTrpGlnGlnGlyAlaGluGlnPheGlyIleGlySerGlyGlySer

1381  CGGTCACGTCAGCGGTTATAGCGTGGTGCATCAGGCACTGGAAGAAGAGCTGGCCGAGTG
       GlyHisValSerGlyTyrSerValValHisGlnAlaLeuGluGluGluLeuAlaGluTrp

1441  GCTTGGCTATTCGCGGGCACTGCTGTTTATCTCTGGTTTCGCCGCTAATCAGGCAGTTAT
       LeuGlyTyrSerArgAlaLeuLeuPheIleSerGlyPheAlaAlaAsnGlnAlaValIle

                         AvaII
1501  TGCCGCGATGATGGCGAAAGAGGACCGTATTGCTGCCGACCGGCTTAGCCATGCCTCATT
       AlaAlaMETMETAlaLysGluAspArgIleAlaAlaAspArgLeuSerHisAlaSerLeu

1561  GCTGGAAGCTGCCAGTTTAAGCCCGTCGCAGCTTCGCCGTTTTGCTCATAACGATGTCAC
       LeuGluAlaAlaSerLeuSerProSerGlnLeuArgArgPheAlaHisAsnAspValThr

1621  TCATTTGGCGCGATTGCTTGCTTCCCCCTGTCCGGGGCAGCAAATGGTGGTGACAGAAGG
       HisLeuAlaArgLeuLeuAlaSerProCysProGlyGlnGlnMETValValThrGluGly
```

FIG.6B

```
1681 CGTGTTCAGCATGGACGGCGATAGTGCGCCACTGGCGGAAATCCAGCAGGTAACGCAACA
      ValPheSerMETAspGlyAspSerAlaProLeuAlaGluIleGlnGlnValThrGlnGln

1741 GCACAATGGCTGGTTGATGGTCGATGATGCCCACGGCACGGGCGTTATCGGGGAGCAGGG
      HisAsnGlyTrpLeuMETValAspAspAlaHisGlyThrGlyValIleGlyGluGlnGly

        PvuII
1801 GCGCGGCAGCTGCTGGCTGCAAAAGGTAAAACCAGAATTGCTGGTAGTGACTTTTGGCAA
      ArgGlySerCysTrpLeuGlnLysValLysProGluLeuLeuValValThrPheGlyLys

1861 AGGATTTGGCGTCAGCGGGGCAGCGGTGCTTTGCTCCAGTACGGTGGCGGATTATCTGCT
      GlyPheGlyValSerGlyAlaAlaValLeuCysSerSerThrValAlaAspTyrLeuLeu

1921 GCAATTCGCCCGCCACCTTATCTACAGCACCAGTATGCCGCCCGCTCAGGCGCAGGCATT
      GlnPheAlaArgHisLeuIleTyrSerThrSerMETProProAlaGlnAlaGlnAlaLeu

1981 ACGTGCGTCGCTGGCGGTCATTCGCAGTGATGAGGGTGATGCACGGCGCGAAAAACTGGC
      ArgAlaSerLeuAlaValIleArgSerAspGluGlyAspAlaArgArgGluLysLeuAla

            MluI
2041 GGCACTCATTACGCGTTTTCGTGCCGGAGTACAGGATTTGCCGTTTACGCTTGCTGATTC
      AlaLeuIleThrArgPheArgAlaGlyValGlnAspLeuProPheThrLeuAlaAspSer

2101 ATGCAGCGCCATCCAGCCATTGATTGTCGGTGATAACAGCCGTGCGTTACAACTGGCAGA
      CysSerAlaIleGlnProLeuIleValGlyAspAsnSerArgAlaLeuGlnLeuAlaGlu

2161 AAAACTGCGTCAGCAAGGCTGCTGGGTCACGGCGATTCGCCCGCCAACCGTACCCGCTGG
      LysLeuArgGlnGlnGlyCysTrpValThrAlaIleArgProProThrValProAlaGly

                                  FspI        EcoRV
2221 TACTGCGCGACTGCGCTTAACGCTAACCGCTGCGCATGAAATGCAGGATATCGACCGTCT
      ThrAlaArgLeuArgLeuThrLeuThrAlaAlaHisGluMETGlnAspIleAspArgLeu

                 bioC
2281 GCTGGAGGTGCTGCATGGCAACGGTTAATAAACAAGCCATTGCAGCGGCATTTGGTCGGG
        SD         METAlaThrValAsnLysGlnAlaIleAlaAlaAlaPheGlyArgAla
     LeuGluValLeuHisGlyAsnGly******

                              BglII
2341 CAGCCGCACACTATGAGCAACATGCAGATCTACAGCGCCAGAGTGCTGACGCCTTACTGG
       AlaAlaHisTyrGluGlnHisAlaAspLeuGlnArgGlnSerAlaAspAlaLeuLeuAla

                                                (AvaII)
2401 CAATGCTTCCACAGCGTAAATACACCCACGTACTGGACGCGGGTTGTGGACCTGGCTGGA
       METLeuProGlnArgLysTyrThrHisValLeuAspAlaGlyCysGlyProGlyTrpMET
```

FIG.6C

```
                                                  BglII
2461 TGAGCCGCCACTGGCGGGAACGTCACGCGCAGGTGACGGCCTTAGATCTCTCGCCGCCAA
      SerArgHisTrpArgGluArgHisAlaGlnValThrAlaLeuAspLeuSerProProMET

                                                            EcoRV
2521 TGCTTGTTCAGGCACGCCAGAAGGATGCCGCAGACCATTATCTGGCGGGAGATATCGAAT
      LeuValGlnAlaArgGlnLysAspAlaAlaAspHisTyrLeuAlaGlyAspIleGluSer

2581 CCCTGCCGTTAGCGACTGCGACGTTCGATCTTGCATGGAGCAATCTCGCAGTGCAGTGGT
      LeuProLeuAlaThrAlaThrPheAspLeuAlaTrpSerAsnLeuAlaValGlnTrpCys

2641 GCGGTAATTTATCCACGGCACTCCGCGAGCTGTATCGGGTGGTGCGCCCCAAAGGCGTGG
      GlyAsnLeuSerThrAlaLeuArgGluLeuTyrArgValValArgProLysGlyValVal

2701 TCGCGTTTACCACGCTGGTGCAGGGATCGTTACCCGAACTGCATCAGGCGTGGCAGGCGG
      AlaPheThrThrLeuValGlnGlySerLeuProGluLeuHisGlnAlaTrpGlnAlaVal

             SphI
2761 TGGACGAGCGTCCGCATGCTAATCGCTTTTTACCGCCAGATGAAATCGAACAGTCGCTGA
      AspGluArgProHisAlaAsnArgPheLeuProProAspGluIleGluGlnSerLeuAsn

2821 ACGGCGTGCATTATCAACATCATATTCAGCCCATCACGCTGTGGTTTGATGATGCGCTCA
      GlyValHisTyrGlnHisHisIleGlnProIleThrLeuTrpPheAspAspAlaLeuSer

                                             BspHI
2881 GTGCCATGCGTTCGCTGAAAGGCATCGGTGCCACGCATCTTCATGAAGGGCGCGACCCGC
      AlaMETArgSerLeuLysGlyIleGlyAlaThrHisLeuHisGluGlyArgAspProArg

  SspI   MluI
2941 GAATATTAACGCGTTCGCAGTTGCAGCGATTGCAACTGGCCTGGCCGCAACAGCAGGGGC
      IleLeuThrArgSerGlnLeuGlnArgLeuGlnLeuAlaTrpProGlnGlnGlnGlyArg

 EcoRV                                           bioD15
3001 GATATCCTCTGACGTATCATCTTTTTTTGGGAGTGATTGCTCGTGAGTAAACGTTATTTT
                                    SD          xMETSerLysArgTyrPhe
      TyrProLeuThrTyrHisLeuPheLeuGlyValIleAlaArgGlu***

                                                   SnoI
3061 GTCACCGGAACGGATACCGAAGTGGGGAAAACTGTCGCCAGTTGTGCACTTTTACAAGCC
     ValThrGlyThrAspThrGluValGlyLysThrValAlaSerCysAlaLeuLeuGlnAla

3121 GCAAAGGCAGCAGGCTACCGGACGGCAGGTTATAAACCGGTCGCCTCTGGCAGCGAAAAG
     AlaThrGlyThrAspThrGluValGlyLysThrValAlaserCysAlaLeuLeuGlnAla
```

FIG.6D

```
                                                                  PstI
3181 ACCCCGGAAGGTTTACGCAATAGCGACGCGCTGGCGTTACAGCGCAACAGCAGCCTGCAG
     ThrProGluGlyLeuArgAsnSerAspAlaLeuAlaLeuGlnArgAsnSerSerLeuGln

    PvuII
3241 CTGGATTACGCAACAGTAAATCCTTACACCTTCGCAGAACCCACTTCGCCGCACATCATC
     LeuaspTyrAlaThrValAsnProTyrThrPheAlaGluProThrSerProHisIleIle

     BssHII                                                BssHII
3301 AGCGCGCAAGAGGGCAGACCGATAGAATCATTGGTAATGAGCGCCGGATTACGCGCGCTT
     SerAlaGlnGluGlyArgProIleGluSerLeuValMETSerAlaGlyLeuArgAlaLeu

3361 GAACAACAGGCTGACTGGGTGTTAGTGGAAGGTGCTGGCGGCTGGTTTACGCCGCTTTCT
     GluGlnGlnAlaAspTrpValLeuValGluGlyAlaGlyGlyTrpPheThrProLeuSer

3421 GACACTTTCACTTTTGCAGATTGGGTAACACAGGAACAACTGCCGGTGATACTGGTAGTT
     AspThrPheThrPheAlaAspTrpValThrGlnGluGlnLeuProValIleLeuValVal

                                    HindII
3481 GGTGTGAAACTCGGCTGTATTAATCACGCGATGTTGACTGCACAGGTAATACAACACGCC
     GlyValLysLeuGlyCysIleAsnHisAlaMETLeuThrAlaGlnValIleGlnHisAla

3541 GGACTGACTCTGGCGGGTTGGGTGGCGAACGATGTTACGCCTCCGGGAAAACGTCACGCT
     GlyLeuThrLeuAlaGlyTrpValAlaAsnAspValThrProProGlyLysArgHisAla

3601 GAATATATGACCACGCTCACCCGCATGATTCCCGCGCCGCTGCTGGGAGAGATCCCCTGG
     GluTyrMETThrThrLeuThrArgMETIleProAlaProLeuLeuGlyGluIleProTrp
                                                           HindII
                                                            SalI
3661 CTTGCAGAAAATCCAGAAAATGCGGCAACCGGAAAGTACATAAACCTTGCCTTCGTCGAC
     LeuAlaGluAsnProGluAsnAlaAlaThrGlyLysTyrIleAsnLeuAlaPheValAsp
       HindII

    MluI SalI                      bioA
3721 GCGTCGACTCTAGGGTTTACAAGTCGATTATGACAACGGACGATCTTGCCTTTGACCAAC
                                SD   METThrThrAspAspLeuAlaPheAspGlnArg
     AlaSerThrLeuGlyPheThrSerArgLeu***

3781 GCCATATCTGGCACCCATACACATCCATGACCTCCCCTCTGCCGGTTTATCCGGTGGTGA
       HisIleTrpHisProTyrThrSerMETThrSerProLeuProValTyrProValValSer

                                                  HindII
3841 GCGCCGAAGGTTGCGAGCTGATTTTGTCTGACGGCAGACGCCTGGTTGACGGTATGTCGT
       AlaGluGlyCysGluLeuIleLeuSerAspGlyArgArgLeuValAspGlyMETSerSer
```

FIG.6E

```
3901 CCTGGTGGGCGGCGATCCACGGCTACAATCACCCGCAGCTTAATGCGGCGATGAAGTCGC
       TrpTrpAlaAlaIleHisGlyTyrAsnHisProGlnLeuAsnAlaAlaMETLysSerGln

3961 AAATTGATGCCATGTCGCATGTGATGTTTGGCGGTATCACCCATGCGCCAGCCATTGAGC
       IleAspAlaMETSerHisValMETPheGlyGlyIleThrHisAlaProAlaIleGluLeu

4021 TGTGCCGCAAACTGGTGGCGATGACGCCGCAACCGCTGGAGTGCGTTTTTCTCGCGGACT
       CysArgLysLeuValAlaMETThrProGlnProLeuGluCysValPheLeuAlaAspSer

                                                  ScaI
4081 CCGGTTCCGTAGCGGTGGAAGTGGCGATGAAAATGGCGTTGCAGTACTGGCAAGCCAAAG
       GlySerValAlaValGluvalAlaMETLysMETAlaLeuGlnTyrTrpGlnAlaLysGly

        BssHII
4141 GCGAAGCGCGCCAGCGTTTTCTGACCTTCCGCAATGGTTATCATGGCGATACCTTTGGCG
       GluAlaArgGlnArgPheLeuThrPheArgAsnGlyTyrHisGlyAspThrPheGlyAla

4201 CGATGTCGGTGTGCGATCCGGATAACTCAATGCACAGTCTGTGGAAAGGCTACCTGCCAG
       METSerValCysAspProAspAsnSerMETHisSerLeuTrpLysGlyTyrLeuProGlu

4261 AAAACCTGTTTGCTCCCGCCCCGCAAAGCCGCATGGATGGCGAATGGGATGAGCGCGATA
       AsnLeuPheAlaProAlaProGlnSerArgMETAspGlyGluTrpAspGluArgAspMET

                                            BspHI
4321 TGGTGGGCTTTGCCCGCCTGATGGCGGCGCATCGTCATGAAATCGCGGCGGTGATCATTG
       ValGlyPheAlaArgLeuMETAlaAlaHisArgHisGluIleAlaAlaValIleIleGlu

                                      FspI
4381 AGCCGATTGTCCAGGGCGCAGGCGGGATGCGCATGTACCATCCGGAATGGTTAAAACGAA
       ProIleValGlnGlyAlaGlyGlyMETArgMETTyrHisProGluTrpLeuLysArgIle

               PvuI NruI
4441 TCCGCAAAATATGCGATCGCGAAGGTATCTTGCTGATTGCCGACGAGATCGCCACTGGAT
       ArgLysIleCysAspArgGluGlyIleLeuLeuIleAlaAspGluIleAlaThrGlyPhe

4501 TTGGTCGTACCGGGAAACTGTTTGCCTGTGAACATGCAGAAATCGCGCCGGACATTTTGT
       GlyArgThrGlyLysLeuPheAlaCysGluHisAlaGluIleAlaProAspIleLeuCys

4561 GCCTCGGTAAAGCCTTAACCGGCGGCACAATGACCCTTTCCGCCACACTCACCACGCGCG
       LeuGlyLysAlaLeuThrGlyGlyThrMETThrLeuSerAlaThrLeuThrThrArgGlu

                                                  NsiI
4621 AGGTTGCAGAAACCATCAGTAACGGTGAAGCCGGTTGCTTTATGCATGGGCCAACTTTTA
       ValAlaGluThrIleSerAsnGlyGluAlaGlyCysPheMETHisGlyProThrPheMET

4681 TGGGCAATCCGCTGGCCTGCGCGGCAGCAAACGCCAGCCTGGCGATTCTCGAATCTGGCG
       GlyAsnProLeuAlaCysAlaAlaAlaAsnAlaSerLeuAlaIleLeuGluSerGlyAsp
```

FIG.6F

```
                                     PvuII
4741 ACTGGCAGCAACAGGTGGCGGATATTGAAGTACAGCTGCGCGAGCAACTTGCCCCCGCCC
       TrpGlnGlnGlnValAlaAspIleGluValGlnLeuArgGluGlnLeuAlaProAlaArg

4801 GTGATGCCGAAATGGTTGCCGATGTGCGCGTACTGGGGGCCATTGGCGTGGTCGAAACCA
       AspAlaGluMETValAlaAspValArgValLeuGlyAlaIleGlyValValGluThrThr

                                                             BamHI
4861 CTCATCCGGTGAATATGGCGGCGCTGCAAAAATTCTTTGTCGAACAGGGTGTCTGGATCC
       HisProValAsnMETAlaAlaLeuGlnLysPhePheValGluGlnGlyValTrpIleArg

4921 GGCCTTTTGGCAAACTGATTTACCTGATGCCGCCCTATATTATTCTCCCGCAACAGTTGC
       ProPheGlyLysLeuIleTyrLeuMETProProTyrIleIleLeuProGlnGlnLeuGln
                     HindII
                      HpaI
4981 AGCGTCTGACCGCAGCGGTTAACCGCGCGGTACAGGATGAAACATTTTTTTGCCAATAAC
       ArgLeuThrAlaAlaValAsnArgAlaValGlnAspGluThrPhePheCysGln***

                                                             BspHI
5041 GAGAAGTCCGCGTGAGGGTTTCTGGCTACACTTTCTGCAAACAAGAAAGGAGGGTTCATG
                                                    SD       MET
ORFI
5101 AAACTCATCAGTAACGATCTGCGCGATGGCGATAAATTGCCGCATCGTCATGTCTTTAAC
     LysLeuIleSerAsnAspLeuArgAspGlyAspLysLeuProHisArgHisValPheAsn

                              SspI
5161 GGCATGGGTTACGATGGCGATAATATTTCACCGCATCTGGCGTGGGATGATGTTCCTGCG
     GlyMETGlyTyrAspGlyAspAsnIleSerProHisLeuAlaTrpAspAspValProAla

5221 GGAACGAAAAGTTTTGTTGTCACCTGCTACGACCCGGATGCGCCAACCGGCTCCGGCTGG
     GlyThrLysSerPheValValThrCysTyrAspProAspAlaProThrGlySerGlyTrp
                   HindII
                    HpaI
5281 TGGCACTGGGTAGTTGTTAACTTACCCGCTGATACCCGCGTATTACCGCAAGGGTTTGGC
     TrpHisTrpValValValAsnLeuProAlaAspThrArgValLeuProGlnGlyPheGly

                                          MluI
5341 TCTGGTCTGGTAGCAATGCCAGACGGCGTTTTGCAGACGCGTACCGACTTTGGTAAAACC
     SerGlyLeuValAlaMETProAspGlyValLeuGlnThrArgThrAspPheGlyLysThr

5401 GGGTACGATGGCGCAGCACCGCCGAAAGGCGAAACTCATCGCTACATTTTTACCGTTCAC
     GlyTyrAspGlyAlaAlaProProLysGlyGluThrHisArgTyrIlePheThrValHis
```

FIG.6G

```
5461 GCGCTGGATATAGAACGTATTGATGTCGATGAAGGTGCCAGCGGCGCGATGGTCGGGTTT
     AlaLeuAspIleGluArgIleAspValAspGluGlyAlaSerGlyAlaMETValGlyPhe

5521 AACGTTCATTTCCACTCTCTGGCAAGCGCCTCGATTACTGCGATGTTTAGTTAATCACTC
     AsnValHisPheHisSerLeuAlaSerAlaSerIleThrAlaMETPheSer***

5581 TGCCAGATGGCGCAATGCCATCTGGTATCACTTAAAGGTATTAAAAACAACTTTTTGTCT

5641 TTTTACCTTCCCGTTTCGCTCAAGTTAGTATAAAAAAGCAGGCTTCAACGGATTCATTTT

5701 TCTATTTCATAGCCCGGAGCAACCTGTGAACACATTTTCAGTTTCCCGTCTGGCGCTGGC

5761 ATTGGCTTTTGGCGTGACGCTGACCGCCTGTAGCTCAACCCCGCCCGATCAACGTCCTTC

                     KpnI  SacI EcoRI  PstI  SphI HindIII
5821 TGATCAAACCGCGCCTGGTACCGAGCTCGAATTCCTGCAGGCATGCAAGCTT-3'
```

FIG.6H

SEQUENCE LISTING

```
(1) GENERAL INFORMATION:

   (iii) NUMBER OF SEQUENCES: 19

(2) INFORMATION FOR SEQ ID NO: 1:

     (i) SEQUENCE CHARACTERISTICS:
          (A) LENGTH: 5872 base pairs
          (B) TYPE: nucleic acid
          (C) STRANDEDNESS: double
          (D) TOPOLOGY: linear

    (ii) MOLECULE TYPE: DNA (genomic)

   (iii) HYPOTHETICAL: NO

   (iii) ANTI-SENSE: NO
```

```
    (vi) ORIGINAL SOURCE:
          (A) ORGANISM: Escherichia coli
          (B) STRAIN: DSM498

   (vii) IMMEDIATE SOURCE:
          (B) CLONE: pBO30A-15/9

    (ix) FEATURE:
          (A) NAME/KEY: CDS
          (B) LOCATION: 117..1157
          (C) IDENTIFICATION METHOD: experimental
          (D) OTHER INFORMATION: /codon_start= 117
               /product= "Biotin synthase"
               /evidence= EXPERIMENTAL
               /gene= "bioB"
               /number= 1

    (ix) FEATURE:
          (A) NAME/KEY: CDS
          (B) LOCATION: 2295..3050
          (D) OTHER INFORMATION: /codon_start= 2295
               /function= "involved in pimeloyl-CoA synthesis"
               /product= "protein"
               /gene= "bioC"
               /number= 3

    (ix) FEATURE:
          (A) NAME/KEY: CDS
          (B) LOCATION: 3750..5039
          (C) IDENTIFICATION METHOD: experimental
          (D) OTHER INFORMATION: /codon_start= 3750
               /EC_number= 2.6.1.62
               /product= "DAPA synthase"
               /evidence= EXPERIMENTAL
               /gene= "bioA"
               /number= 5
               /standard_name=
               "S-Adenosyl-L-methionine:8-amino-7-oxononanoate
               aminotransf."

    (ix) FEATURE:
          (A) NAME/KEY: CDS
          (B) LOCATION: 5098..5574
          (C) IDENTIFICATION METHOD: experimental
          (D) OTHER INFORMATION: /codon_start= 5098
               /function= "unknown, involved in biotin synthesis"
               /product= "protein"
               /evidence= EXPERIMENTAL
               /gene= "ORFI"
               /number= 6

    (ix) FEATURE:
          (A) NAME/KEY: -10_signal
          (B) LOCATION: 45..49
          (C) IDENTIFICATION METHOD: experimental
          (D) OTHER INFORMATION: /evidence= EXPERIMENTAL
               /standard_name= "promoter ptac"

    (ix) FEATURE:
          (A) NAME/KEY: -35_signal
          (B) LOCATION: 23..28
          (D) OTHER INFORMATION: /standard_name= "promoter ptac"

    (ix) FEATURE:
          (A) NAME/KEY: RBS
          (B) LOCATION: 105..119
          (C) IDENTIFICATION METHOD: experimental
          (D) OTHER INFORMATION: /evidence= EXPERIMENTAL
               /standard_name= "bioB RBS no.9"

    (ix) FEATURE:
          (A) NAME/KEY: RBS
          (B) LOCATION: 2284..2297
          (D) OTHER INFORMATION: /standard_name= "bioC RBS"

    (ix) FEATURE:
          (A) NAME/KEY: RBS
          (B) LOCATION: 3742..3752
```

-continued

```
          (D) OTHER INFORMATION: /standard_name= "bioA RBS"

     (ix) FEATURE:
          (A) NAME/KEY: RBS
          (B) LOCATION: 5088..5100
          (D) OTHER INFORMATION: /standard_name= "ORFI RBS"

     (ix) FEATURE:
          (A) NAME/KEY: terminator
          (B) LOCATION: 5583..5644
          (D) OTHER INFORMATION: /standard_name= "rho-independent
               transcriptional terminator"

     (ix) FEATURE:
          (A) NAME/KEY: stem_loop
          (B) LOCATION: 5583..5605

     (ix) FEATURE:
          (A) NAME/KEY: promoter
          (B) LOCATION: 1..96
          (C) IDENTIFICATION METHOD: experimental
          (D) OTHER INFORMATION: /function= "promoter ptac"
               /evidence= EXPERIMENTAL

      (x) PUBLICATION INFORMATION:
          (H) DOCUMENT NUMBER: WO 87/01391 B1
          (I) FILING DATE: 26-AUG-1986
          (J) PUBLICATION DATE: 07-APR-1993

     (xi) SEQUENCE DESCRIPTION: SEQ ID NO: 1:

AAGCTTACTC CCCATCCCCC TGTTGACAAT TAATCATCGG CTCGTATAAT GTGTGGAATT      60

GTGAGCGGAT AACAATTTCA CACAGGAAAC AGGATCGGTA CCTAAGGAGA CTAGTC         116

ATG GCT CAC CGC CCA CGC TGG ACA TTG TCG CAA GTC ACA GAA TTA TTT       164
Met Ala His Arg Pro Arg Trp Thr Leu Ser Gln Val Thr Glu Leu Phe
  1               5                  10                  15

GAA AAA CCG TTG CTG GAT CTG CTG TTT GAA GCG CAG CAG GTG CAT CGC       212
Glu Lys Pro Leu Leu Asp Leu Leu Phe Glu Ala Gln Gln Val His Arg
             20                  25                  30

CAG CAT TTC GAT CCT CGT CAG GTG CAG GTC AGC ACG TTG CTG TCG ATT       260
Gln His Phe Asp Pro Arg Gln Val Gln Val Ser Thr Leu Leu Ser Ile
         35                  40                  45

AAG ACC GGA GCT TGT CCG GAA GAT TGC AAA TAC TGC CCG CAA AGC TCG       308
Lys Thr Gly Ala Cys Pro Glu Asp Cys Lys Tyr Cys Pro Gln Ser Ser
     50                  55                  60

CGC TAC AAA ACC GGG CTG GAA GCC GAG CGG TTG ATG GAA GTT GAA CAG       356
Arg Tyr Lys Thr Gly Leu Glu Ala Glu Arg Leu Met Glu Val Glu Gln
 65                  70                  75                  80

GTG CTG GAG TCG GCG CGC AAA GCG AAA GCG GCA GGA TCG ACG CGC TTC       404
Val Leu Glu Ser Ala Arg Lys Ala Lys Ala Ala Gly Ser Thr Arg Phe
                 85                  90                  95

TGT ATG GGC GCG GCG TGG AAG AAT CCC CAC GAA CGC GAT ATG CCG TAC       452
Cys Met Gly Ala Ala Trp Lys Asn Pro His Glu Arg Asp Met Pro Tyr
            100                 105                 110

CTG GAA CAA ATG GTG CAG GGG GTA AAA GCG ATG GGG CTG GAG GCG TGT       500
Leu Glu Gln Met Val Gln Gly Val Lys Ala Met Gly Leu Glu Ala Cys
        115                 120                 125

ATG ACG CTG GGC ACG TTG AGT GAA TCT CAG GCG CAG CGC CTC GCG AAC       548
Met Thr Leu Gly Thr Leu Ser Glu Ser Gln Ala Gln Arg Leu Ala Asn
    130                 135                 140

GCC GGG CTG GAT TAC TAC AAC CAC AAC CTG GAC ACC TCG CCG GAG TTT       596
Ala Gly Leu Asp Tyr Tyr Asn His Asn Leu Asp Thr Ser Pro Glu Phe
145                 150                 155                 160

TAC GGC AAT ATC ATC ACC ACA CGC ACT TAT CAG GAA CGC CTC GAT ACG       644
Tyr Gly Asn Ile Ile Thr Thr Arg Thr Tyr Gln Glu Arg Leu Asp Thr
                165                 170                 175
```

-continued

```
CTG GAA AAA GTG CGC GAT GCC GGG ATC AAA GTC TGT TCT GGC GGC ATT      692
Leu Glu Lys Val Arg Asp Ala Gly Ile Lys Val Cys Ser Gly Gly Ile
            180                 185                 190

GTG GGC TTA GGC GAA ACG GTA AAA GAT CGC GCC GGA TTA TTG CTG CAA      740
Val Gly Leu Gly Glu Thr Val Lys Asp Arg Ala Gly Leu Leu Leu Gln
        195                 200                 205

CTG GCA AAC CTG CCG ACG CCG CCG GAA AGC GTG CCA ATC AAC ATG CTG      788
Leu Ala Asn Leu Pro Thr Pro Pro Glu Ser Val Pro Ile Asn Met Leu
    210                 215                 220

GTG AAG GTG AAA GGC ACG CCG CTT GCC GAT AAC GAT GAT GTC GAT GCC      836
Val Lys Val Lys Gly Thr Pro Leu Ala Asp Asn Asp Asp Val Asp Ala
225                 230                 235                 240

TTT GAT TTT ATT CGC ACC ATT GCG GTC GCG CGG ATC ATG ATG CCA ACC      884
Phe Asp Phe Ile Arg Thr Ile Ala Val Ala Arg Ile Met Met Pro Thr
                245                 250                 255

TCT TAC GTG CGC CTT TCT GCC GGA CGC GAG CAG ATG AAC GAA CAG ACT      932
Ser Tyr Val Arg Leu Ser Ala Gly Arg Glu Gln Met Asn Glu Gln Thr
            260                 265                 270

CAG GCG ATG TGC TTT ATG GCA GGC GCA AAC TCG ATT TTC TAC GGT TGC      980
Gln Ala Met Cys Phe Met Ala Gly Ala Asn Ser Ile Phe Tyr Gly Cys
        275                 280                 285

AAA CTG CTG ACC ACG CCG AAT CCG GAA GAA GAT AAA GAC CTG CAA CTG     1028
Lys Leu Leu Thr Thr Pro Asn Pro Glu Glu Asp Lys Asp Leu Gln Leu
    290                 295                 300

TTC CGC AAA CTG GGG CTA AAT CCG CAG CAA ACT GCC GTG CTG GCA GGG     1076
Phe Arg Lys Leu Gly Leu Asn Pro Gln Gln Thr Ala Val Leu Ala Gly
305                 310                 315                 320

GAT AAC GAA CAA CAG CAA CGT CTT GAA CAG GCG CTG ATG ACC CCG GAC     1124
Asp Asn Glu Gln Gln Gln Arg Leu Glu Gln Ala Leu Met Thr Pro Asp
                325                 330                 335

ACC GAC GAA TAT TAC AAC GCG GCA GCA TTA TGAGCTGGCA GGAGAAAATC       1174
Thr Asp Glu Tyr Tyr Asn Ala Ala Ala Leu
            340                 345

AACGCGGCGC TCGATGCGCG GCGTGCTGCC GATGCCCTGC GTCGCCGTTA TCCGGTGGCG   1234

CAAGGAGCCG GACGCTGGCT GGTGGCGGAT GATCGCCAGT ATCTGAACTT TTCCAGTAAC   1294

GATTATTTAG GTTTAAGCCA TCATCCGCAA ATTATCCGTG CCTGGCAGCA GGGGGCGGAG   1354

CAATTTGGCA TCGGTAGCGG CGGCTCCGGT CACGTCAGCG GTTATAGCGT GGTGCATCAG   1414

GCACTGGAAG AAGAGCTGGC CGAGTGGCTT GGCTATTCGC GGGCACTGCT GTTTATCTCT   1474

GGTTTCGCCG CTAATCAGGC AGTTATTGCC GCGATGATGG CGAAAGAGGA CCGTATTGCT   1534

GCCGACCGGC TTAGCCATGC CTCATTGCTG GAAGCTGCCA GTTTAAGCCC GTCGCAGCTT   1594

CGCCGTTTTG CTCATAACGA TGTCACTCAT TTGGCGCGAT TGCTTGCTTC CCCCTGTCCG   1654

GGGCAGCAAA TGGTGGTGAC AGAAGGCGTG TTCAGCATGG ACGGCGATAG TGCGCCACTG   1714

GCGGAAATCC AGCAGGTAAC GCAACAGCAC AATGGCTGGT TGATGGTCGA TGATGCCCAC   1774

GGCACGGGCG TTATCGGGGA GCAGGGGCGC GGCAGCTGCT GGCTGCAAAA GGTAAAACCA   1834

GAATTGCTGG TAGTGACTTT TGGCAAAGGA TTTGGCGTCA GCGGGGCAGC GGTGCTTTGC   1894

TCCAGTACGG TGGCGGATTA TCTGCTGCAA TTCGCCCGCC ACCTTATCTA CAGCACCAGT   1954

ATGCCGCCCG CTCAGGCGCA GGCATTACGT GCGTCGCTGG CGGTCATTCG CAGTGATGAG   2014

GGTGATGCAC GGCGCGAAAA ACTGGCGGCA CTCATTACGC GTTTTCGTGC CGGAGTACAG   2074

GATTTGCCGT TTACGCTTGC TGATTCATGC AGCGCCATCC AGCCATTGAT TGTCGGTGAT   2134

AACAGCCGTG CGTTACAACT GGCAGAAAAA CTGCGTCAGC AAGGCTGCTG GGTCACGGCG   2194

ATTCGCCCGC CAACCGTACC CGCTGGTACT GCGCGACTGC GCTTAACGCT AACCGCTGCG   2254
```

-continued

```
CATGAAATGC AGGATATCGA CCGTCTGCTG GAGGTGCTGC ATG GCA ACG GTT AAT     2309
                                            Met Ala Thr Val Asn
                                              1               5

AAA CAA GCC ATT GCA GCG GCA TTT GGT CGG GCA GCC GCA CAC TAT GAG     2357
Lys Gln Ala Ile Ala Ala Ala Phe Gly Arg Ala Ala Ala His Tyr Glu
                 10                  15                  20

CAA CAT GCA GAT CTA CAG CGC CAG AGT GCT GAC GCC TTA CTG GCA ATG     2405
Gln His Ala Asp Leu Gln Arg Gln Ser Ala Asp Ala Leu Leu Ala Met
             25                  30                  35

CTT CCA CAG CGT AAA TAC ACC CAC GTA CTG GAC GCG GGT TGT GGA CCT     2453
Leu Pro Gln Arg Lys Tyr Thr His Val Leu Asp Ala Gly Cys Gly Pro
         40                  45                  50

GGC TGG ATG AGC CGC CAC TGG CGG GAA CGT CAC GCG CAG GTG ACG GCC     2501
Gly Trp Met Ser Arg His Trp Arg Glu Arg His Ala Gln Val Thr Ala
     55                  60                  65

TTA GAT CTC TCG CCG CCA ATG CTT GTT CAG GCA CGC CAG AAG GAT GCC     2549
Leu Asp Leu Ser Pro Pro Met Leu Val Gln Ala Arg Gln Lys Asp Ala
 70                  75                  80                  85

GCA GAC CAT TAT CTG GCG GGA GAT ATC GAA TCC CTG CCG TTA GCG ACT     2597
Ala Asp His Tyr Leu Ala Gly Asp Ile Glu Ser Leu Pro Leu Ala Thr
                 90                  95                 100

GCG ACG TTC GAT CTT GCA TGG AGC AAT CTC GCA GTG CAG TGG TGC GGT     2645
Ala Thr Phe Asp Leu Ala Trp Ser Asn Leu Ala Val Gln Trp Cys Gly
            105                 110                 115

AAT TTA TCC ACG GCA CTC CGC GAG CTG TAT CGG GTG GTG CGC CCC AAA     2693
Asn Leu Ser Thr Ala Leu Arg Glu Leu Tyr Arg Val Val Arg Pro Lys
        120                 125                 130

GGC GTG GTC GCG TTT ACC ACG CTG GTG CAG GGA TCG TTA CCC GAA CTG     2741
Gly Val Val Ala Phe Thr Thr Leu Val Gln Gly Ser Leu Pro Glu Leu
    135                 140                 145

CAT CAG GCG TGG CAG GCG GTG GAC GAG CGT CCG CAT GCT AAT CGC TTT     2789
His Gln Ala Trp Gln Ala Val Asp Glu Arg Pro His Ala Asn Arg Phe
150                 155                 160                 165

TTA CCG CCA GAT GAA ATC GAA CAG TCG CTG AAC GGC GTG CAT TAT CAA     2837
Leu Pro Pro Asp Glu Ile Glu Gln Ser Leu Asn Gly Val His Tyr Gln
                170                 175                 180

CAT CAT ATT CAG CCC ATC ACG CTG TGG TTT GAT GAT GCG CTC AGT GCC     2885
His His Ile Gln Pro Ile Thr Leu Trp Phe Asp Asp Ala Leu Ser Ala
            185                 190                 195

ATG CGT TCG CTG AAA GGC ATC GGT GCC ACG CAT CTT CAT GAA GGG CGC     2933
Met Arg Ser Leu Lys Gly Ile Gly Ala Thr His Leu His Glu Gly Arg
        200                 205                 210

GAC CCG CGA ATA TTA ACG CGT TCG CAG TTG CAG CGA TTG CAA CTG GCC     2981
Asp Pro Arg Ile Leu Thr Arg Ser Gln Leu Gln Arg Leu Gln Leu Ala
    215                 220                 225

TGG CCG CAA CAG CAG GGG CGA TAT CCT CTG ACG TAT CAT CTT TTT TTG     3029
Trp Pro Gln Gln Gln Gly Arg Tyr Pro Leu Thr Tyr His Leu Phe Leu
230                 235                 240                 245

GGA GTG ATT GCT CGT GAG TAAACGTTAT TTTGTCACCG GAACGGATAC            3077
Gly Val Ile Ala Arg Glu
                250

CGAAGTGGGG AAAACTGTCG CCAGTTGTGC ACTTTTACAA GCCGCAAAGG CAGCAGGCTA   3137

CCGGACGGCA GGTTATAAAC CGGTCGCCTC TGGCAGCGAA AAGACCCCGG AAGGTTTACG   3197

CAATAGCGAC GCGCTGGCGT TACAGCGCAA CAGCAGCCTG CAGCTGGATT ACGCAACAGT   3257

AAATCCTTAC ACCTTCGCAG AACCCACTTC GCCGCACATC ATCAGCGCGC AAGAGGGCAG   3317

ACCGATAGAA TCATTGGTAA TGAGCGCCGG ATTACGCGCG CTTGAACAAC AGGCTGACTG   3377
```

-continued

```
GGTGTTAGTG GAAGGTGCTG GCGGCTGGTT TACGCCGCTT TCTGACACTT TCACTTTTGC   3437

AGATTGGGTA ACACAGGAAC AACTGCCGGT GATACTGGTA GTTGGTGTGA AACTCGGCTG   3497

TATTAATCAC GCGATGTTGA CTGCACAGGT AATACAACAC GCCGGACTGA CTCTGGCGGG   3557

TTGGGTGGCG AACGATGTTA CGCCTCCGGG AAAACGTCAC GCTGAATATA TGACCACGCT   3617

CACCCGCATG ATTCCCGCGC CGCTGCTGGG AGAGATCCCC TGGCTTGCAG AAAATCCAGA   3677

AAATGCGGCA ACCGGAAAGT ACATAAACCT TGCCTTCGTC GACGCGTCGA CTCTAGGGTT   3737

TACAAGTCGA TT ATG ACA ACG GAC GAT CTT GCC TTT GAC CAA CGC CAT       3785
              Met Thr Thr Asp Asp Leu Ala Phe Asp Gln Arg His
                1               5                  10

ATC TGG CAC CCA TAC ACA TCC ATG ACC TCC CCT CTG CCG GTT TAT CCG     3833
Ile Trp His Pro Tyr Thr Ser Met Thr Ser Pro Leu Pro Val Tyr Pro
        15                  20                  25

GTG GTG AGC GCC GAA GGT TGC GAG CTG ATT TTG TCT GAC GGC AGA CGC     3881
Val Val Ser Ala Glu Gly Cys Glu Leu Ile Leu Ser Asp Gly Arg Arg
    30                  35                  40

CTG GTT GAC GGT ATG TCG TCC TGG TGG GCG GCG ATC CAC GGC TAC AAT     3929
Leu Val Asp Gly Met Ser Ser Trp Trp Ala Ala Ile His Gly Tyr Asn
 45                  50                  55                  60

CAC CCG CAG CTT AAT GCG GCG ATG AAG TCG CAA ATT GAT GCC ATG TCG     3977
His Pro Gln Leu Asn Ala Ala Met Lys Ser Gln Ile Asp Ala Met Ser
                65                  70                  75

CAT GTG ATG TTT GGC GGT ATC ACC CAT GCG CCA GCC ATT GAG CTG TGC     4025
His Val Met Phe Gly Gly Ile Thr His Ala Pro Ala Ile Glu Leu Cys
            80                  85                  90

CGC AAA CTG GTG GCG ATG ACG CCG CAA CCG CTG GAG TGC GTT TTT CTC     4073
Arg Lys Leu Val Ala Met Thr Pro Gln Pro Leu Glu Cys Val Phe Leu
        95                 100                 105

GCG GAC TCC GGT TCC GTA GCG GTG GAA GTG GCG ATG AAA ATG GCG TTG     4121
Ala Asp Ser Gly Ser Val Ala Val Glu Val Ala Met Lys Met Ala Leu
    110                 115                 120

CAG TAC TGG CAA GCC AAA GGC GAA GCG CGC CAG CGT TTT CTG ACC TTC     4169
Gln Tyr Trp Gln Ala Lys Gly Glu Ala Arg Gln Arg Phe Leu Thr Phe
125                 130                 135                 140

CGC AAT GGT TAT CAT GGC GAT ACC TTT GGC GCG ATG TCG GTG TGC GAT     4217
Arg Asn Gly Tyr His Gly Asp Thr Phe Gly Ala Met Ser Val Cys Asp
                145                 150                 155

CCG GAT AAC TCA ATG CAC AGT CTG TGG AAA GGC TAC CTG CCA GAA AAC     4265
Pro Asp Asn Ser Met His Ser Leu Trp Lys Gly Tyr Leu Pro Glu Asn
            160                 165                 170

CTG TTT GCT CCC GCC CCG CAA AGC CGC ATG GAT GGC GAA TGG GAT GAG     4313
Leu Phe Ala Pro Ala Pro Gln Ser Arg Met Asp Gly Glu Trp Asp Glu
        175                 180                 185

CGC GAT ATG GTG GGC TTT GCC CGC CTG ATG GCG GCG CAT CGT CAT GAA     4361
Arg Asp Met Val Gly Phe Ala Arg Leu Met Ala Ala His Arg His Glu
    190                 195                 200

ATC GCG GCG GTG ATC ATT GAG CCG ATT GTC CAG GGC GCA GGC GGG ATG     4409
Ile Ala Ala Val Ile Ile Glu Pro Ile Val Gln Gly Ala Gly Gly Met
205                 210                 215                 220

CGC ATG TAC CAT CCG GAA TGG TTA AAA CGA ATC CGC AAA ATA TGC GAT     4457
Arg Met Tyr His Pro Glu Trp Leu Lys Arg Ile Arg Lys Ile Cys Asp
                225                 230                 235

CGC GAA GGT ATC TTG CTG ATT GCC GAC GAG ATC GCC ACT GGA TTT GGT     4505
Arg Glu Gly Ile Leu Leu Ile Ala Asp Glu Ile Ala Thr Gly Phe Gly
            240                 245                 250

CGT ACC GGG AAA CTG TTT GCC TGT GAA CAT GCA GAA ATC GCG CCG GAC     4553
Arg Thr Gly Lys Leu Phe Ala Cys Glu His Ala Glu Ile Ala Pro Asp
        255                 260                 265
```

-continued

```
ATT TTG TGC CTC GGT AAA GCC TTA ACC GGC GGC ACA ATG ACC CTT TCC     4601
Ile Leu Cys Leu Gly Lys Ala Leu Thr Gly Gly Thr Met Thr Leu Ser
    270                 275                 280

GCC ACA CTC ACC ACG CGC GAG GTT GCA GAA ACC ATC AGT AAC GGT GAA     4649
Ala Thr Leu Thr Thr Arg Glu Val Ala Glu Thr Ile Ser Asn Gly Glu
285                 290                 295                 300

GCC GGT TGC TTT ATG CAT GGG CCA ACT TTT ATG GGC AAT CCG CTG GCC     4697
Ala Gly Cys Phe Met His Gly Pro Thr Phe Met Gly Asn Pro Leu Ala
                305                 310                 315

TGC GCG GCA GCA AAC GCC AGC CTG GCG ATT CTC GAA TCT GGC GAC TGG     4745
Cys Ala Ala Ala Asn Ala Ser Leu Ala Ile Leu Glu Ser Gly Asp Trp
            320                 325                 330

CAG CAA CAG GTG GCG GAT ATT GAA GTA CAG CTG CGC GAG CAA CTT GCC     4793
Gln Gln Gln Val Ala Asp Ile Glu Val Gln Leu Arg Glu Gln Leu Ala
        335                 340                 345

CCC GCC CGT GAT GCC GAA ATG GTT GCC GAT GTG CGC GTA CTG GGG GCC     4841
Pro Ala Arg Asp Ala Glu Met Val Ala Asp Val Arg Val Leu Gly Ala
    350                 355                 360

ATT GGC GTG GTC GAA ACC ACT CAT CCG GTG AAT ATG GCG GCG CTG CAA     4889
Ile Gly Val Val Glu Thr Thr His Pro Val Asn Met Ala Ala Leu Gln
365                 370                 375                 380

AAA TTC TTT GTC GAA CAG GGT GTC TGG ATC CGG CCT TTT GGC AAA CTG     4937
Lys Phe Phe Val Glu Gln Gly Val Trp Ile Arg Pro Phe Gly Lys Leu
                385                 390                 395

ATT TAC CTG ATG CCG CCC TAT ATT ATT CTC CCG CAA CAG TTG CAG CGT     4985
Ile Tyr Leu Met Pro Pro Tyr Ile Ile Leu Pro Gln Gln Leu Gln Arg
            400                 405                 410

CTG ACC GCA GCG GTT AAC CGC GCG GTA CAG GAT GAA ACA TTT TTT TGC     5033
Leu Thr Ala Ala Val Asn Arg Ala Val Gln Asp Glu Thr Phe Phe Cys
        415                 420                 425

CAA TAACGAGAAG TCCGCGTGAG GGTTTCTGGC TACACTTTCT GCAAACAAGA          5086
Gln
    430

AAGGAGGGTT C ATG AAA CTC ATC AGT AAC GAT CTG CGC GAT GGC GAT AAA    5136
             Met Lys Leu Ile Ser Asn Asp Leu Arg Asp Gly Asp Lys
               1               5                  10

TTG CCG CAT CGT CAT GTC TTT AAC GGC ATG GGT TAC GAT GGC GAT AAT     5184
Leu Pro His Arg His Val Phe Asn Gly Met Gly Tyr Asp Gly Asp Asn
     15                  20                  25

ATT TCA CCG CAT CTG GCG TGG GAT GAT GTT CCT GCG GGA ACG AAA AGT     5232
Ile Ser Pro His Leu Ala Trp Asp Asp Val Pro Ala Gly Thr Lys Ser
 30                  35                  40                  45

TTT GTT GTC ACC TGC TAC GAC CCG GAT GCG CCA ACC GGC TCC GGC TGG     5280
Phe Val Val Thr Cys Tyr Asp Pro Asp Ala Pro Thr Gly Ser Gly Trp
                 50                  55                  60

TGG CAC TGG GTA GTT GTT AAC TTA CCC GCT GAT ACC CGC GTA TTA CCG     5328
Trp His Trp Val Val Val Asn Leu Pro Ala Asp Thr Arg Val Leu Pro
             65                  70                  75

CAA GGG TTT GGC TCT GGT CTG GTA GCA ATG CCA GAC GGC GTT TTG CAG     5376
Gln Gly Phe Gly Ser Gly Leu Val Ala Met Pro Asp Gly Val Leu Gln
         80                  85                  90

ACG CGT ACC GAC TTT GGT AAA ACC GGG TAC GAT GGC GCA GCA CCG CCG     5424
Thr Arg Thr Asp Phe Gly Lys Thr Gly Tyr Asp Gly Ala Ala Pro Pro
     95                 100                 105

AAA GGC GAA ACT CAT CGC TAC ATT TTT ACC GTT CAC GCG CTG GAT ATA     5472
Lys Gly Glu Thr His Arg Tyr Ile Phe Thr Val His Ala Leu Asp Ile
110                 115                 120                 125

GAA CGT ATT GAT GTC GAT GAA GGT GCC AGC GGC GCG ATG GTC GGG TTT     5520
Glu Arg Ile Asp Val Asp Glu Gly Ala Ser Gly Ala Met Val Gly Phe
```

-continued

```
                130                 135                 140

AAC GTT CAT TTC CAC TCT CTG GCA AGC GCC TCG ATT ACT GCG ATG TTT     5568
Asn Val His Phe His Ser Leu Ala Ser Ala Ser Ile Thr Ala Met Phe
            145                 150                 155

AGT TAATCACTCT GCCAGATGGC GCAATGCCAT CTGGTATCAC TTAAAGGTAT          5621
Ser

TAAAAACAAC TTTTTGTCTT TTTACCTTCC CGTTTCGCTC AAGTTAGTAT AAAAAAGCAG   5681

GCTTCAACGG ATTCATTTTT CTATTTCATA GCCCGGAGCA ACCTGTGAAC ACATTTTCAG   5741

TTTCCCGTCT GGCGCTGGCA TTGGCTTTTG GCGTGACGCT GACCGCCTGT AGCTCAACCC   5801

CGCCCGATCA ACGTCCTTCT GATCAAACCG CGCCTGGTAC CGAGCTCGAA TTCCTGCAGG   5861

CATGCAAGCT T                                                        5872
```

(2) INFORMATION FOR SEQ ID NO: 2:

(i) SEQUENCE CHARACTERISTICS:
(A) LENGTH: 346 amino acids
(B) TYPE: amino acid
(D) TOPOLOGY: linear (ii) MOLECULE TYPE: protein (xi) SEQUENCE DESCRIPTION: SEQ ID NO: 2:

```
Met Ala His Arg Pro Arg Trp Thr Leu Ser Gln Val Thr Glu Leu Phe
  1               5                  10                  15

Glu Lys Pro Leu Leu Asp Leu Leu Phe Glu Ala Gln Gln Val His Arg
             20                  25                  30

Gln His Phe Asp Pro Arg Gln Val Gln Val Ser Thr Leu Leu Ser Ile
         35                  40                  45

Lys Thr Gly Ala Cys Pro Glu Asp Cys Lys Tyr Cys Pro Gln Ser Ser
     50                  55                  60

Arg Tyr Lys Thr Gly Leu Glu Ala Glu Arg Leu Met Glu Val Glu Gln
 65                  70                  75                  80

Val Leu Glu Ser Ala Arg Lys Ala Lys Ala Ala Gly Ser Thr Arg Phe
                 85                  90                  95

Cys Met Gly Ala Ala Trp Lys Asn Pro His Glu Arg Asp Met Pro Tyr
            100                 105                 110

Leu Glu Gln Met Val Gln Gly Val Lys Ala Met Gly Leu Glu Ala Cys
        115                 120                 125

Met Thr Leu Gly Thr Leu Ser Glu Ser Gln Ala Gln Arg Leu Ala Asn
    130                 135                 140

Ala Gly Leu Asp Tyr Tyr Asn His Asn Leu Asp Thr Ser Pro Glu Phe
145                 150                 155                 160

Tyr Gly Asn Ile Ile Thr Thr Arg Thr Tyr Gln Glu Arg Leu Asp Thr
                165                 170                 175

Leu Glu Lys Val Arg Asp Ala Gly Ile Lys Val Cys Ser Gly Gly Ile
            180                 185                 190

Val Gly Leu Gly Glu Thr Val Lys Asp Arg Ala Gly Leu Leu Leu Gln
        195                 200                 205

Leu Ala Asn Leu Pro Thr Pro Pro Glu Ser Val Pro Ile Asn Met Leu
    210                 215                 220

Val Lys Val Lys Gly Thr Pro Leu Ala Asp Asn Asp Asp Val Asp Ala
225                 230                 235                 240

Phe Asp Phe Ile Arg Thr Ile Ala Val Ala Arg Ile Met Met Pro Thr
                245                 250                 255
```

-continued

```
Ser Tyr Val Arg Leu Ser Ala Gly Arg Glu Gln Met Asn Glu Gln Thr
            260                 265                 270

Gln Ala Met Cys Phe Met Ala Gly Ala Asn Ser Ile Phe Tyr Gly Cys
        275                 280                 285

Lys Leu Leu Thr Thr Pro Asn Pro Glu Glu Asp Lys Asp Leu Gln Leu
    290                 295                 300

Phe Arg Lys Leu Gly Leu Asn Pro Gln Gln Thr Ala Val Leu Ala Gly
305                 310                 315                 320

Asp Asn Glu Gln Gln Gln Arg Leu Glu Gln Ala Leu Met Thr Pro Asp
                325                 330                 335

Thr Asp Glu Tyr Tyr Asn Ala Ala Ala Leu
            340                 345
```

(2) INFORMATION FOR SEQ ID NO: 3:

(i) SEQUENCE CHARACTERISTICS:
(A) LENGTH: 251 amino acids
(B) TYPE: amino acid
(D) TOPOLOGY: linear (ii) MOLECULE TYPE: protein (xi) SEQUENCE DESCRIPTION: SEQ ID NO: 3:

```
Met Ala Thr Val Asn Lys Gln Ala Ile Ala Ala Ala Phe Gly Arg Ala
  1               5                  10                  15

Ala Ala His Tyr Glu Gln His Ala Asp Leu Gln Arg Gln Ser Ala Asp
             20                  25                  30

Ala Leu Leu Ala Met Leu Pro Gln Arg Lys Tyr Thr His Val Leu Asp
         35                  40                  45

Ala Gly Cys Gly Pro Gly Trp Met Ser Arg His Trp Arg Glu Arg His
     50                  55                  60

Ala Gln Val Thr Ala Leu Asp Leu Ser Pro Pro Met Leu Val Gln Ala
 65                  70                  75                  80

Arg Gln Lys Asp Ala Ala Asp His Tyr Leu Ala Gly Asp Ile Glu Ser
                 85                  90                  95

Leu Pro Leu Ala Thr Ala Thr Phe Asp Leu Ala Trp Ser Asn Leu Ala
            100                 105                 110

Val Gln Trp Cys Gly Asn Leu Ser Thr Ala Leu Arg Glu Leu Tyr Arg
        115                 120                 125

Val Val Arg Pro Lys Gly Val Val Ala Phe Thr Thr Leu Val Gln Gly
    130                 135                 140

Ser Leu Pro Glu Leu His Gln Ala Trp Gln Ala Val Asp Glu Arg Pro
145                 150                 155                 160

His Ala Asn Arg Phe Leu Pro Pro Asp Glu Ile Glu Gln Ser Leu Asn
                165                 170                 175

Gly Val His Tyr Gln His His Ile Gln Pro Ile Thr Leu Trp Phe Asp
            180                 185                 190

Asp Ala Leu Ser Ala Met Arg Ser Leu Lys Gly Ile Gly Ala Thr His
        195                 200                 205

Leu His Glu Gly Arg Asp Pro Arg Ile Leu Thr Arg Ser Gln Leu Gln
    210                 215                 220

Arg Leu Gln Leu Ala Trp Pro Gln Gln Gln Gly Arg Tyr Pro Leu Thr
225                 230                 235                 240

Tyr His Leu Phe Leu Gly Val Ile Ala Arg Glu
                245                 250
```

(2) INFORMATION FOR SEQ ID NO: 4:

(i) SEQUENCE CHARACTERISTICS:
(A) LENGTH: 429 amino acids
(B) TYPE: amino acid
(D) TOPOLOGY: linear (ii) MOLECULE TYPE: protein (xi) SEQUENCE DESCRIPTION: SEQ ID NO: 4:

```
Met Thr Thr Asp Asp Leu Ala Phe Asp Gln Arg His Ile Trp His Pro
  1               5                  10                  15

Tyr Thr Ser Met Thr Ser Pro Leu Pro Val Tyr Pro Val Val Ser Ala
             20                  25                  30

Glu Gly Cys Glu Leu Ile Leu Ser Asp Gly Arg Arg Leu Val Asp Gly
        35                  40                  45

Met Ser Ser Trp Trp Ala Ala Ile His Gly Tyr Asn His Pro Gln Leu
    50                  55                  60

Asn Ala Ala Met Lys Ser Gln Ile Asp Ala Met Ser His Val Met Phe
 65                  70                  75                  80

Gly Gly Ile Thr His Ala Pro Ala Ile Glu Leu Cys Arg Lys Leu Val
                 85                  90                  95

Ala Met Thr Pro Gln Pro Leu Glu Cys Val Phe Leu Ala Asp Ser Gly
            100                 105                 110

Ser Val Ala Val Glu Val Ala Met Lys Met Ala Leu Gln Tyr Trp Gln
        115                 120                 125

Ala Lys Gly Glu Ala Arg Gln Arg Phe Leu Thr Phe Arg Asn Gly Tyr
    130                 135                 140

His Gly Asp Thr Phe Gly Ala Met Ser Val Cys Asp Pro Asp Asn Ser
145                 150                 155                 160

Met His Ser Leu Trp Lys Gly Tyr Leu Pro Glu Asn Leu Phe Ala Pro
                165                 170                 175

Ala Pro Gln Ser Arg Met Asp Gly Glu Trp Asp Glu Arg Asp Met Val
            180                 185                 190

Gly Phe Ala Arg Leu Met Ala Ala His Arg His Glu Ile Ala Ala Val
        195                 200                 205

Ile Ile Glu Pro Ile Val Gln Gly Ala Gly Gly Met Arg Met Tyr His
    210                 215                 220

Pro Glu Trp Leu Lys Arg Ile Arg Lys Ile Cys Asp Arg Glu Gly Ile
225                 230                 235                 240

Leu Leu Ile Ala Asp Glu Ile Ala Thr Gly Phe Gly Arg Thr Gly Lys
                245                 250                 255

Leu Phe Ala Cys Glu His Ala Glu Ile Ala Pro Asp Ile Leu Cys Leu
            260                 265                 270

Gly Lys Ala Leu Thr Gly Gly Thr Met Thr Leu Ser Ala Thr Leu Thr
        275                 280                 285

Thr Arg Glu Val Ala Glu Thr Ile Ser Asn Gly Glu Ala Gly Cys Phe
    290                 295                 300

Met His Gly Pro Thr Phe Met Gly Asn Pro Leu Ala Cys Ala Ala Ala
305                 310                 315                 320

Asn Ala Ser Leu Ala Ile Leu Glu Ser Gly Asp Trp Gln Gln Gln Val
                325                 330                 335

Ala Asp Ile Glu Val Gln Leu Arg Glu Gln Leu Ala Pro Ala Arg Asp
            340                 345                 350

Ala Glu Met Val Ala Asp Val Arg Val Leu Gly Ala Ile Gly Val Val
        355                 360                 365
```

```
Glu Thr Thr His Pro Val Asn Met Ala Ala Leu Gln Lys Phe Phe Val
    370                 375                 380

Glu Gln Gly Val Trp Ile Arg Pro Phe Gly Lys Leu Ile Tyr Leu Met
385                 390                 395                 400

Pro Pro Tyr Ile Ile Leu Pro Gln Gln Leu Gln Arg Leu Thr Ala Ala
                405                 410                 415

Val Asn Arg Ala Val Gln Asp Glu Thr Phe Phe Cys Gln
            420                 425
```

(2) INFORMATION FOR SEQ ID NO: 5:

(i) SEQUENCE CHARACTERISTICS:
(A) LENGTH: 158 amino acids
(B) TYPE: amino acid
(D) TOPOLOGY: linear (ii) MOLECULE TYPE: protein (xi) SEQUENCE DESCRIPTION: SEQ ID NO: 5:

```
Met Lys Leu Ile Ser Asn Asp Leu Arg Asp Gly Asp Lys Leu Pro His
  1               5                  10                  15

Arg His Val Phe Asn Gly Met Gly Tyr Asp Gly Asp Asn Ile Ser Pro
             20                  25                  30

His Leu Ala Trp Asp Asp Val Pro Ala Gly Thr Lys Ser Phe Val Val
         35                  40                  45

Thr Cys Tyr Asp Pro Asp Ala Pro Thr Gly Ser Gly Trp Trp His Trp
     50                  55                  60

Val Val Val Asn Leu Pro Ala Asp Thr Arg Val Leu Pro Gln Gly Phe
 65                  70                  75                  80

Gly Ser Gly Leu Val Ala Met Pro Asp Gly Val Leu Gln Thr Arg Thr
                 85                  90                  95

Asp Phe Gly Lys Thr Gly Tyr Asp Gly Ala Ala Pro Pro Lys Gly Glu
            100                 105                 110

Thr His Arg Tyr Ile Phe Thr Val His Ala Leu Asp Ile Glu Arg Ile
        115                 120                 125

Asp Val Asp Glu Gly Ala Ser Gly Ala Met Val Gly Phe Asn Val His
    130                 135                 140

Phe His Ser Leu Ala Ser Ala Ser Ile Thr Ala Met Phe Ser
145                 150                 155
```

(2) INFORMATION FOR SEQ ID NO: 6:

(i) SEQUENCE CHARACTERISTICS:
(A) LENGTH: 5872 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (vi) ORIGINAL SOURCE:
(A) ORGANISM: Escherichia coli
(B) STRAIN: DSM498

(vii) IMMEDIATE SOURCE:
(B) CLONE: pBO30A15-9

(ix) FEATURE:
(A) NAME/KEY: CDS
(B) LOCATION: 1154..2308
(C) IDENTIFICATION METHOD: experimental -continued

```
        (D) OTHER INFORMATION: /codon_start= 1154
             /EC_number= 2.3.1.47
             /product= "KAPA synthase"
             /evidence= EXPERIMENTAL
             /gene= "bioF"
             /number= 2
             /standard_name= "8-Amino-7-oxononanoate synthase"

    (ix) FEATURE:
        (A) NAME/KEY: CDS
        (B) LOCATION: 3043..3753
        (C) IDENTIFICATION METHOD: experimental
        (D) OTHER INFORMATION: /codon_start= 3043
             /EC_number= 6.3.3.3
             /product= "DTB synthase"
             /evidence= EXPERIMENTAL
             /gene= "bioD"
             /number= 4
             /standard_name= "Dethiobiotin synthase"

    (ix) FEATURE:
        (A) NAME/KEY: RBS
        (B) LOCATION: 1141..1156
        (D) OTHER INFORMATION: /standard_name= "bioF RBS"

    (ix) FEATURE:
        (A) NAME/KEY: RBS
        (B) LOCATION: 3030..3045
        (D) OTHER INFORMATION: /standard_name= "bioD RBS"

     (x) PUBLICATION INFORMATION:
        (H) DOCUMENT NUMBER: WO 87/01391 B1
        (I) FILING DATE: 26-AUG-1986
        (J) PUBLICATION DATE: 07-APR-1993

    (xi) SEQUENCE DESCRIPTION: SEQ ID NO: 6:

AAGCTTACTC CCCATCCCCC TGTTGACAAT TAATCATCGG CTCGTATAAT GTGTGGAATT      60

GTGAGCGGAT AACAATTTCA CACAGGAAAC AGGATCGGTA CCTAAGGAGA CTAGTCATGG     120

CTCACCGCCC ACGCTGGACA TTGTCGCAAG TCACAGAATT ATTTGAAAAA CCGTTGCTGG     180

ATCTGCTGTT TGAAGCGCAG CAGGTGCATC GCCAGCATTT CGATCCTCGT CAGGTGCAGG     240

TCAGCACGTT GCTGTCGATT AAGACCGGAG CTTGTCCGGA AGATTGCAAA TACTGCCCGC     300

AAAGCTCGCG CTACAAAACC GGGCTGGAAG CCGAGCGGTT GATGGAAGTT GAACAGGTGC     360

TGGAGTCGGC GCGCAAAGCG AAAGCGGCAG GATCGACGCG CTTCTGTATG GGCGCGGCGT     420

GGAAGAATCC CCACGAACGC GATATGCCGT ACCTGGAACA AATGGTGCAG GGGGTAAAAG     480

CGATGGGGCT GGAGGCGTGT ATGACGCTGG GCACGTTGAG TGAATCTCAG GCGCAGCGCC     540

TCGCGAACGC CGGGCTGGAT TACTACAACC ACAACCTGGA CACCTCGCCG GAGTTTTACG     600

GCAATATCAT CACCACACGC ACTTATCAGG AACGCCTCGA TACGCTGGAA AAAGTGCGCG     660

ATGCCGGGAT CAAAGTCTGT TCTGGCGGCA TTGTGGGCTT AGGCGAAACG GTAAAAGATC     720

GCGCCGGATT ATTGCTGCAA CTGGCAAACC TGCCGACGCC GCCGGAAAGC GTGCCAATCA     780

ACATGCTGGT GAAGGTGAAA GGCACGCCGC TTGCCGATAA CGATGATGTC GATGCCTTTG     840

ATTTTATTCG CACCATTGCG GTCGCGCGGA TCATGATGCC AACCTCTTAC GTGCGCCTTT     900

CTGCCGGACG CGAGCAGATG AACGAACAGA CTCAGGCGAT GTGCTTTATG GCAGGCGCAA     960

ACTCGATTTT CTACGGTTGC AAACTGCTGA CCACGCCGAA TCCGGAAGAA GATAAAGACC    1020

TGCAACTGTT CCGCAAACTG GGGCTAAATC CGCAGCAAAC TGCCGTGCTG GCAGGGGATA    1080

ACGAACAACA GCAACGTCTT GAACAGGCGC TGATGACCCC GGACACCGAC GAATATTACA    1140

ACGCGGCAGC ATT ATG AGC TGG CAG GAG AAA ATC AAC GCG GCG CTC GAT       1189
               Met Ser Trp Gln Glu Lys Ile Asn Ala Ala Leu Asp
                 1               5                  10
```

-continued

```
GCG CGG CGT GCT GCC GAT GCC CTG CGT CGC CGT TAT CCG GTG GCG CAA      1237
Ala Arg Arg Ala Ala Asp Ala Leu Arg Arg Arg Tyr Pro Val Ala Gln
         15                  20                  25

GGA GCC GGA CGC TGG CTG GTG GCG GAT GAT CGC CAG TAT CTG AAC TTT      1285
Gly Ala Gly Arg Trp Leu Val Ala Asp Asp Arg Gln Tyr Leu Asn Phe
     30                  35                  40

TCC AGT AAC GAT TAT TTA GGT TTA AGC CAT CAT CCG CAA ATT ATC CGT      1333
Ser Ser Asn Asp Tyr Leu Gly Leu Ser His His Pro Gln Ile Ile Arg
 45                  50                  55                  60

GCC TGG CAG CAG GGG GCG GAG CAA TTT GGC ATC GGT AGC GGC GGC TCC      1381
Ala Trp Gln Gln Gly Ala Glu Gln Phe Gly Ile Gly Ser Gly Gly Ser
                 65                  70                  75

GGT CAC GTC AGC GGT TAT AGC GTG GTG CAT CAG GCA CTG GAA GAA GAG      1429
Gly His Val Ser Gly Tyr Ser Val Val His Gln Ala Leu Glu Glu Glu
             80                  85                  90

CTG GCC GAG TGG CTT GGC TAT TCG CGG GCA CTG CTG TTT ATC TCT GGT      1477
Leu Ala Glu Trp Leu Gly Tyr Ser Arg Ala Leu Leu Phe Ile Ser Gly
         95                 100                 105

TTC GCC GCT AAT CAG GCA GTT ATT GCC GCG ATG ATG GCG AAA GAG GAC      1525
Phe Ala Ala Asn Gln Ala Val Ile Ala Ala Met Met Ala Lys Glu Asp
    110                 115                 120

CGT ATT GCT GCC GAC CGG CTT AGC CAT GCC TCA TTG CTG GAA GCT GCC      1573
Arg Ile Ala Ala Asp Arg Leu Ser His Ala Ser Leu Leu Glu Ala Ala
125                 130                 135                 140

AGT TTA AGC CCG TCG CAG CTT CGC CGT TTT GCT CAT AAC GAT GTC ACT      1621
Ser Leu Ser Pro Ser Gln Leu Arg Arg Phe Ala His Asn Asp Val Thr
                145                 150                 155

CAT TTG GCG CGA TTG CTT GCT TCC CCC TGT CCG GGG CAG CAA ATG GTG      1669
His Leu Ala Arg Leu Leu Ala Ser Pro Cys Pro Gly Gln Gln Met Val
            160                 165                 170

GTG ACA GAA GGC GTG TTC AGC ATG GAC GGC GAT AGT GCG CCA CTG GCG      1717
Val Thr Glu Gly Val Phe Ser Met Asp Gly Asp Ser Ala Pro Leu Ala
        175                 180                 185

GAA ATC CAG CAG GTA ACG CAA CAG CAC AAT GGC TGG TTG ATG GTC GAT      1765
Glu Ile Gln Gln Val Thr Gln Gln His Asn Gly Trp Leu Met Val Asp
    190                 195                 200

GAT GCC CAC GGC ACG GGC GTT ATC GGG GAG CAG GGG CGC GGC AGC TGC      1813
Asp Ala His Gly Thr Gly Val Ile Gly Glu Gln Gly Arg Gly Ser Cys
205                 210                 215                 220

TGG CTG CAA AAG GTA AAA CCA GAA TTG CTG GTA GTG ACT TTT GGC AAA      1861
Trp Leu Gln Lys Val Lys Pro Glu Leu Leu Val Val Thr Phe Gly Lys
                225                 230                 235

GGA TTT GGC GTC AGC GGG GCA GCG GTG CTT TGC TCC AGT ACG GTG GCG      1909
Gly Phe Gly Val Ser Gly Ala Ala Val Leu Cys Ser Ser Thr Val Ala
            240                 245                 250

GAT TAT CTG CTG CAA TTC GCC CGC CAC CTT ATC TAC AGC ACC AGT ATG      1957
Asp Tyr Leu Leu Gln Phe Ala Arg His Leu Ile Tyr Ser Thr Ser Met
        255                 260                 265

CCG CCC GCT CAG GCG CAG GCA TTA CGT GCG TCG CTG GCG GTC ATT CGC      2005
Pro Pro Ala Gln Ala Gln Ala Leu Arg Ala Ser Leu Ala Val Ile Arg
    270                 275                 280

AGT GAT GAG GGT GAT GCA CGG CGC GAA AAA CTG GCG GCA CTC ATT ACG      2053
Ser Asp Glu Gly Asp Ala Arg Arg Glu Lys Leu Ala Ala Leu Ile Thr
285                 290                 295                 300

CGT TTT CGT GCC GGA GTA CAG GAT TTG CCG TTT ACG CTT GCT GAT TCA      2101
Arg Phe Arg Ala Gly Val Gln Asp Leu Pro Phe Thr Leu Ala Asp Ser
                305                 310                 315

TGC AGC GCC ATC CAG CCA TTG ATT GTC GGT GAT AAC AGC CGT GCG TTA      2149
Cys Ser Ala Ile Gln Pro Leu Ile Val Gly Asp Asn Ser Arg Ala Leu
            320                 325                 330
```

-continued

```
CAA CTG GCA GAA AAA CTG CGT CAG CAA GGC TGC TGG GTC ACG GCG ATT     2197
Gln Leu Ala Glu Lys Leu Arg Gln Gln Gly Cys Trp Val Thr Ala Ile
        335                 340                 345

CGC CCG CCA ACC GTA CCC GCT GGT ACT GCG CGA CTG CGC TTA ACG CTA     2245
Arg Pro Pro Thr Val Pro Ala Gly Thr Ala Arg Leu Arg Leu Thr Leu
    350                 355                 360

ACC GCT GCG CAT GAA ATG CAG GAT ATC GAC CGT CTG CTG GAG GTG CTG     2293
Thr Ala Ala His Glu Met Gln Asp Ile Asp Arg Leu Leu Glu Val Leu
365                 370                 375                 380

CAT GGC AAC GGT TAATAAACAA GCCATTGCAG CGGCATTTGG TCGGGCAGCC         2345
His Gly Asn Gly
                385

GCACACTATG AGCAACATGC AGATCTACAG CGCCAGAGTG CTGACGCCTT ACTGGCAATG   2405

CTTCCACAGC GTAAATACAC CCACGTACTG GACGCGGGTT GTGGACCTGG CTGGATGAGC   2465

CGCCACTGGC GGGAACGTCA CGCGCAGGTG ACGGCCTTAG ATCTCTCGCC GCCAATGCTT   2525

GTTCAGGCAC GCCAGAAGGA TGCCGCAGAC CATTATCTGG CGGGAGATAT CGAATCCCTG   2585

CCGTTAGCGA CTGCGACGTT CGATCTTGCA TGGAGCAATC TCGCAGTGCA GTGGTGCGGT   2645

AATTTATCCA CGGCACTCCG CGAGCTGTAT CGGGTGGTGC GCCCCAAAGG CGTGGTCGCG   2705

TTTACCACGC TGGTGCAGGG ATCGTTACCC GAACTGCATC AGGCGTGGCA GGCGGTGGAC   2765

GAGCGTCCGC ATGCTAATCG CTTTTTACCG CCAGATGAAA TCGAACAGTC GCTGAACGGC   2825

GTGCATTATC AACATCATAT TCAGCCCATC ACGCTGTGGT TTGATGATGC GCTCAGTGCC   2885

ATGCGTTCGC TGAAAGGCAT CGGTGCCACG CATCTTCATG AAGGGCGCGA CCCGCGAATA   2945

TTAACGCGTT CGCAGTTGCA GCGATTGCAA CTGGCCTGGC CGCAACAGCA GGGGCGATAT   3005

CCTCTGACGT ATCATCTTTT TTTGGGAGTG ATTGCTC GTG AGT AAA CGT TAT TTT    3060
                                         Val Ser Lys Arg Tyr Phe
                                           1               5

GTC ACC GGA ACG GAT ACC GAA GTG GGG AAA ACT GTC GCC AGT TGT GCA     3108
Val Thr Gly Thr Asp Thr Glu Val Gly Lys Thr Val Ala Ser Cys Ala
            10                  15                  20

CTT TTA CAA GCC GCA AAG GCA GCA GGC TAC CGG ACG GCA GGT TAT AAA     3156
Leu Leu Gln Ala Ala Lys Ala Ala Gly Tyr Arg Thr Ala Gly Tyr Lys
        25                  30                  35

CCG GTC GCC TCT GGC AGC GAA AAG ACC CCG GAA GGT TTA CGC AAT AGC     3204
Pro Val Ala Ser Gly Ser Glu Lys Thr Pro Glu Gly Leu Arg Asn Ser
    40                  45                  50

GAC GCG CTG GCG TTA CAG CGC AAC AGC AGC CTG CAG CTG GAT TAC GCA     3252
Asp Ala Leu Ala Leu Gln Arg Asn Ser Ser Leu Gln Leu Asp Tyr Ala
 55                  60                  65                  70

ACA GTA AAT CCT TAC ACC TTC GCA GAA CCC ACT TCG CCG CAC ATC ATC     3300
Thr Val Asn Pro Tyr Thr Phe Ala Glu Pro Thr Ser Pro His Ile Ile
                75                  80                  85

AGC GCG CAA GAG GGC AGA CCG ATA GAA TCA TTG GTA ATG AGC GCC GGA     3348
Ser Ala Gln Glu Gly Arg Pro Ile Glu Ser Leu Val Met Ser Ala Gly
            90                  95                 100

TTA CGC GCG CTT GAA CAA CAG GCT GAC TGG GTG TTA GTG GAA GGT GCT     3396
Leu Arg Ala Leu Glu Gln Gln Ala Asp Trp Val Leu Val Glu Gly Ala
        105                 110                 115

GGC GGC TGG TTT ACG CCG CTT TCT GAC ACT TTC ACT TTT GCA GAT TGG     3444
Gly Gly Trp Phe Thr Pro Leu Ser Asp Thr Phe Thr Phe Ala Asp Trp
    120                 125                 130

GTA ACA CAG GAA CAA CTG CCG GTG ATA CTG GTA GTT GGT GTG AAA CTC     3492
Val Thr Gln Glu Gln Leu Pro Val Ile Leu Val Val Gly Val Lys Leu
135                 140                 145                 150
```

-continued

```
GGC TGT ATT AAT CAC GCG ATG TTG ACT GCA CAG GTA ATA CAA CAC GCC     3540
Gly Cys Ile Asn His Ala Met Leu Thr Ala Gln Val Ile Gln His Ala
                155                 160                 165

GGA CTG ACT CTG GCG GGT TGG GTG GCG AAC GAT GTT ACG CCT CCG GGA     3588
Gly Leu Thr Leu Ala Gly Trp Val Ala Asn Asp Val Thr Pro Pro Gly
            170                 175                 180

AAA CGT CAC GCT GAA TAT ATG ACC ACG CTC ACC CGC ATG ATT CCC GCG     3636
Lys Arg His Ala Glu Tyr Met Thr Thr Leu Thr Arg Met Ile Pro Ala
        185                 190                 195

CCG CTG CTG GGA GAG ATC CCC TGG CTT GCA GAA AAT CCA GAA AAT GCG     3684
Pro Leu Leu Gly Glu Ile Pro Trp Leu Ala Glu Asn Pro Glu Asn Ala
    200                 205                 210

GCA ACC GGA AAG TAC ATA AAC CTT GCC TTC GTC GAC GCG TCG ACT CTA     3732
Ala Thr Gly Lys Tyr Ile Asn Leu Ala Phe Val Asp Ala Ser Thr Leu
215                 220                 225                 230

GGG TTT ACA AGT CGA TTA TGACAACGGA CGATCTTGCC TTTGACCAAC            3780
Gly Phe Thr Ser Arg Leu
                235

GCCATATCTG GCACCCATAC ACATCCATGA CCTCCCCTCT GCCGGTTTAT CCGGTGGTGA   3840

GCGCCGAAGG TTGCGAGCTG ATTTTGTCTG ACGGCAGACG CCTGGTTGAC GGTATGTCGT   3900

CCTGGTGGGC GGCGATCCAC GGCTACAATC ACCCGCAGCT TAATGCGGCG ATGAAGTCGC   3960

AAATTGATGC CATGTCGCAT GTGATGTTTG GCGGTATCAC CCATGCGCCA GCCATTGAGC   4020

TGTGCCGCAA ACTGGTGGCG ATGACGCCGC AACCGCTGGA GTGCGTTTTT CTCGCGGACT   4080

CCGGTTCCGT AGCGGTGGAA GTGGCGATGA AAATGGCGTT GCAGTACTGG CAAGCCAAAG   4140

GCGAAGCGCG CCAGCGTTTT CTGACCTTCC GCAATGGTTA TCATGGCGAT ACCTTTGGCG   4200

CGATGTCGGT GTGCGATCCG GATAACTCAA TGCACAGTCT GTGGAAAGGC TACCTGCCAG   4260

AAAACCTGTT TGCTCCCGCC CCGCAAAGCC GCATGGATGG CGAATGGGAT GAGCGCGATA   4320

TGGTGGGCTT TGCCCGCCTG ATGGCGGCGC ATCGTCATGA AATCGCGGCG GTGATCATTG   4380

AGCCGATTGT CCAGGGCGCA GGCGGGATGC GCATGTACCA TCCGGAATGG TTAAAACGAA   4440

TCCGCAAAAT ATGCGATCGC GAAGGTATCT TGCTGATTGC CGACGAGATC GCCACTGGAT   4500

TTGGTCGTAC CGGGAAACTG TTTGCCTGTG AACATGCAGA AATCGCGCCG GACATTTTGT   4560

GCCTCGGTAA AGCCTTAACC GGCGGCACAA TGACCCTTTC CGCCACACTC ACCACGCGCG   4620

AGGTTGCAGA AACCATCAGT AACGGTGAAG CCGGTTGCTT TATGCATGGG CCAACTTTTA   4680

TGGGCAATCC GCTGGCCTGC GCGGCAGCAA ACGCCAGCCT GGCGATTCTC GAATCTGGCG   4740

ACTGGCAGCA ACAGGTGGCG GATATTGAAG TACAGCTGCG CGAGCAACTT GCCCCCGCCC   4800

GTGATGCCGA AATGGTTGCC GATGTGCGCG TACTGGGGGC CATTGGCGTG GTCGAAACCA   4860

CTCATCCGGT GAATATGGCG GCGCTGCAAA AATTCTTTGT CGAACAGGGT GTCTGGATCC   4920

GGCCTTTTGG CAAACTGATT TACCTGATGC CGCCCTATAT TATTCTCCCG CAACAGTTGC   4980

AGCGTCTGAC CGCAGCGGTT AACCGCGCGG TACAGGATGA AACATTTTTT TGCCAATAAC   5040

GAGAAGTCCG CGTGAGGGTT TCTGGCTACA CTTTCTGCAA ACAAGAAAGG AGGGTTCATG   5100

AAACTCATCA GTAACGATCT GCGCGATGGC GATAAATTGC CGCATCGTCA TGTCTTTAAC   5160

GGCATGGGTT ACGATGGCGA TAATATTTCA CCGCATCTGG CGTGGGATGA TGTTCCTGCG   5220

GGAACGAAAA GTTTTGTTGT CACCTGCTAC GACCCGGATG CGCCAACCGG CTCCGGCTGG   5280

TGGCACTGGG TAGTTGTTAA CTTACCCGCT GATACCCGCG TATTACCGCA AGGGTTTGGC   5340

TCTGGTCTGG TAGCAATGCC AGACGGCGTT TTGCAGACGC GTACCGACTT TGGTAAAACC   5400

GGGTACGATG GCGCAGCACC GCCGAAAGGC GAAACTCATC GCTACATTTT TACCGTTCAC   5460
```

-continued

```
GCGCTGGATA TAGAACGTAT TGATGTCGAT GAAGGTGCCA GCGGCGCGAT GGTCGGGTTT   5520

AACGTTCATT TCCACTCTCT GGCAAGCGCC TCGATTACTG CGATGTTTAG TTAATCACTC   5580

TGCCAGATGG CGCAATGCCA TCTGGTATCA CTTAAAGGTA TTAAAAACAA CTTTTTGTCT   5640

TTTTACCTTC CCGTTTCGCT CAAGTTAGTA TAAAAAAGCA GGCTTCAACG GATTCATTTT   5700

TCTATTTCAT AGCCCGGAGC AACCTGTGAA CACATTTTCA GTTTCCCGTC TGGCGCTGGC   5760

ATTGGCTTTT GGCGTGACGC TGACCGCCTG TAGCTCAACC CCGCCCGATC AACGTCCTTC   5820

TGATCAAACC GCGCCTGGTA CCGAGCTCGA ATTCCTGCAG GCATGCAAGC TT           5872
```

(2) INFORMATION FOR SEQ ID NO: 7:

(i) SEQUENCE CHARACTERISTICS:
(A) LENGTH: 384 amino acids
(B) TYPE: amino acid
(D) TOPOLOGY: linear (ii) MOLECULE TYPE: protein (xi) SEQUENCE DESCRIPTION: SEQ ID NO: 7:

```
Met Ser Trp Gln Glu Lys Ile Asn Ala Ala Leu Asp Ala Arg Arg Ala
  1               5                  10                  15

Ala Asp Ala Leu Arg Arg Arg Tyr Pro Val Ala Gln Gly Ala Gly Arg
             20                  25                  30

Trp Leu Val Ala Asp Asp Arg Gln Tyr Leu Asn Phe Ser Ser Asn Asp
        35                  40                  45

Tyr Leu Gly Leu Ser His His Pro Gln Ile Ile Arg Ala Trp Gln Gln
    50                  55                  60

Gly Ala Glu Gln Phe Gly Ile Gly Ser Gly Gly Ser Gly His Val Ser
 65                  70                  75                  80

Gly Tyr Ser Val Val His Gln Ala Leu Glu Glu Glu Leu Ala Glu Trp
                 85                  90                  95

Leu Gly Tyr Ser Arg Ala Leu Leu Phe Ile Ser Gly Phe Ala Ala Asn
            100                 105                 110

Gln Ala Val Ile Ala Ala Met Met Ala Lys Glu Asp Arg Ile Ala Ala
        115                 120                 125

Asp Arg Leu Ser His Ala Ser Leu Leu Glu Ala Ala Ser Leu Ser Pro
    130                 135                 140

Ser Gln Leu Arg Arg Phe Ala His Asn Asp Val Thr His Leu Ala Arg
145                 150                 155                 160

Leu Leu Ala Ser Pro Cys Pro Gly Gln Gln Met Val Val Thr Glu Gly
                165                 170                 175

Val Phe Ser Met Asp Gly Asp Ser Ala Pro Leu Ala Glu Ile Gln Gln
            180                 185                 190

Val Thr Gln Gln His Asn Gly Trp Leu Met Val Asp Asp Ala His Gly
        195                 200                 205

Thr Gly Val Ile Gly Glu Gln Gly Arg Gly Ser Cys Trp Leu Gln Lys
    210                 215                 220

Val Lys Pro Glu Leu Leu Val Val Thr Phe Gly Lys Gly Phe Gly Val
225                 230                 235                 240

Ser Gly Ala Ala Val Leu Cys Ser Ser Thr Val Ala Asp Tyr Leu Leu
                245                 250                 255

Gln Phe Ala Arg His Leu Ile Tyr Ser Thr Ser Met Pro Pro Ala Gln
            260                 265                 270

Ala Gln Ala Leu Arg Ala Ser Leu Ala Val Ile Arg Ser Asp Glu Gly
```

-continued

```
        275                 280                 285

Asp Ala Arg Arg Glu Lys Leu Ala Ala Leu Ile Thr Arg Phe Arg Ala
    290                 295                 300

Gly Val Gln Asp Leu Pro Phe Thr Leu Ala Asp Ser Cys Ser Ala Ile
305                 310                 315                 320

Gln Pro Leu Ile Val Gly Asp Asn Ser Arg Ala Leu Gln Leu Ala Glu
                325                 330                 335

Lys Leu Arg Gln Gln Gly Cys Trp Val Thr Ala Ile Arg Pro Pro Thr
            340                 345                 350

Val Pro Ala Gly Thr Ala Arg Leu Arg Leu Thr Leu Thr Ala Ala His
        355                 360                 365

Glu Met Gln Asp Ile Asp Arg Leu Leu Glu Val Leu His Gly Asn Gly
    370                 375                 380
```

(2) INFORMATION FOR SEQ ID NO: 8:

(i) SEQUENCE CHARACTERISTICS:
(A) LENGTH: 236 amino acids
(B) TYPE: amino acid
(D) TOPOLOGY: linear (ii) MOLECULE TYPE: protein (xi) SEQUENCE DESCRIPTION: SEQ ID NO: 8:

```
Val Ser Lys Arg Tyr Phe Val Thr Gly Thr Asp Thr Glu Val Gly Lys
  1               5                  10                  15

Thr Val Ala Ser Cys Ala Leu Leu Gln Ala Ala Lys Ala Ala Gly Tyr
             20                  25                  30

Arg Thr Ala Gly Tyr Lys Pro Val Ala Ser Gly Ser Glu Lys Thr Pro
         35                  40                  45

Glu Gly Leu Arg Asn Ser Asp Ala Leu Ala Leu Gln Arg Asn Ser Ser
     50                  55                  60

Leu Gln Leu Asp Tyr Ala Thr Val Asn Pro Tyr Thr Phe Ala Glu Pro
 65                  70                  75                  80

Thr Ser Pro His Ile Ile Ser Ala Gln Glu Gly Arg Pro Ile Glu Ser
                 85                  90                  95

Leu Val Met Ser Ala Gly Leu Arg Ala Leu Glu Gln Gln Ala Asp Trp
            100                 105                 110

Val Leu Val Glu Gly Ala Gly Gly Trp Phe Thr Pro Leu Ser Asp Thr
        115                 120                 125

Phe Thr Phe Ala Asp Trp Val Thr Gln Glu Gln Leu Pro Val Ile Leu
    130                 135                 140

Val Val Gly Val Lys Leu Gly Cys Ile Asn His Ala Met Leu Thr Ala
145                 150                 155                 160

Gln Val Ile Gln His Ala Gly Leu Thr Leu Ala Gly Trp Val Ala Asn
                165                 170                 175

Asp Val Thr Pro Pro Gly Lys Arg His Ala Glu Tyr Met Thr Thr Leu
            180                 185                 190

Thr Arg Met Ile Pro Ala Pro Leu Leu Gly Glu Ile Pro Trp Leu Ala
        195                 200                 205

Glu Asn Pro Glu Asn Ala Ala Thr Gly Lys Tyr Ile Asn Leu Ala Phe
    210                 215                 220

Val Asp Ala Ser Thr Leu Gly Phe Thr Ser Arg Leu
225                 230                 235
```

(2) INFORMATION FOR SEQ ID NO: 9:

```
     (i) SEQUENCE CHARACTERISTICS:
          (A) LENGTH: 143 base pairs
          (B) TYPE: nucleic acid
          (C) STRANDEDNESS: double
          (D) TOPOLOGY: linear

    (ii) MOLECULE TYPE: DNA (genomic)

   (iii) HYPOTHETICAL: NO

   (iii) ANTI-SENSE: NO

    (vi) ORIGINAL SOURCE:
          (A) ORGANISM: Escherichia coli

   (vii) IMMEDIATE SOURCE:
          (B) CLONE: pBO30

    (ix) FEATURE:
          (A) NAME/KEY: CDS
          (B) LOCATION: 1..24
          (D) OTHER INFORMATION: /partial
               /EC_number= 6.3.3.3
               /product= "Dethiobiotin synthase"
               /gene= "bioD"

    (ix) FEATURE:
          (A) NAME/KEY: CDS
          (B) LOCATION: 120..143
          (D) OTHER INFORMATION: /partial
               /codon_start= 120
               /EC_number= 2.6.1.62
               /product= "DAPA synthase"
               /gene= "bioA"
               /pseudo

    (ix) FEATURE:
          (A) NAME/KEY: RBS
          (B) LOCATION: 111..122
          (D) OTHER INFORMATION: /standard_name= "bioA RBS"

    (ix) FEATURE:
          (A) NAME/KEY: stem_loop
          (B) LOCATION: 38..85

     (x) PUBLICATION INFORMATION:
          (H) DOCUMENT NUMBER: WO 87/01391 B1
          (I) FILING DATE: 26-AUG-1986
          (J) PUBLICATION DATE: 07-APR-1993

    (xi) SEQUENCE DESCRIPTION: SEQ ID NO: 9:

TAC ATA AAC CTT GCC TTG TTG TAGCCATTCT GTATTTGGTT AAATTGCGAG          51
Tyr Ile Asn Leu Ala Leu Leu
  1               5

CGAGATCGCG TCTTCGATTG ACTGCAATTT AACCCTCTAG AGTCGACTCT AGGGTTTACA    111

AGTCGATT ATG ACA ACG GAC GAT CTT GCC TTT                             143
         Met Thr Thr Asp Asp Leu Ala Phe
           1               5


(2) INFORMATION FOR SEQ ID NO: 10:

     (i) SEQUENCE CHARACTERISTICS:
          (A) LENGTH: 7 amino acids
          (B) TYPE: amino acid
          (D) TOPOLOGY: linear

    (ii) MOLECULE TYPE: protein

    (xi) SEQUENCE DESCRIPTION: SEQ ID NO: 10:

Tyr Ile Asn Leu Ala Leu Leu
  1               5
```

-continued (2) INFORMATION FOR SEQ ID NO: 11:

(i) SEQUENCE CHARACTERISTICS:
(A) LENGTH: 8 amino acids
(B) TYPE: amino acid
(D) TOPOLOGY: linear (ii) MOLECULE TYPE: protein (xi) SEQUENCE DESCRIPTION: SEQ ID NO: 11:

```
Met Thr Thr Asp Asp Leu Ala Phe
  1               5
```

(2) INFORMATION FOR SEQ ID NO: 12:

(i) SEQUENCE CHARACTERISTICS:
(A) LENGTH: 93 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iii) ANTI-SENSE: NO (vi) ORIGINAL SOURCE:
(A) ORGANISM: Escherichia coli (vii) IMMEDIATE SOURCE:
(B) CLONE: pBO30A-9

(ix) FEATURE:
(A) NAME/KEY: CDS
(B) LOCATION: 1..24
(D) OTHER INFORMATION: /partial
/codon_start= 1
/EC_number= 6.3.3.3
/product= "DTB synthase"
/gene= "bioD"

(ix) FEATURE:
(A) NAME/KEY: CDS
(B) LOCATION: 70..93
(D) OTHER INFORMATION: /partial
/codon_start= 70
/EC_number= 2.6.1.62
/product= "DAPA synthase"
/gene= "bioA"

(ix) FEATURE:
(A) NAME/KEY: RBS
(B) LOCATION: 61..72
(D) OTHER INFORMATION: /standard_name= "bioA RBS"

(x) PUBLICATION INFORMATION:
(H) DOCUMENT NUMBER: WO 87/01391 B1
(I) FILING DATE: 26-AUG-1986
(J) PUBLICATION DATE: 07-APR-1993

(xi) SEQUENCE DESCRIPTION: SEQ ID NO: 12:

```
TAC ATA AAC CTT GCC TTG TTG TAGCCATTCT GTATTTGGTT CGTCGACTCT          51
Tyr Ile Asn Leu Ala Leu Leu
  1               5

AGGGTTTACA AGTCGATT ATG ACA ACG GAC GAT CTT GCC TTT                   93
                    Met Thr Thr Asp Asp Leu Ala Phe
                      1               5
```

(2) INFORMATION FOR SEQ ID NO: 13:

(i) SEQUENCE CHARACTERISTICS:
(A) LENGTH: 7 amino acids
(B) TYPE: amino acid

-continued (D) TOPOLOGY: linear (ii) MOLECULE TYPE: protein (xi) SEQUENCE DESCRIPTION: SEQ ID NO: 13:

```
Tyr Ile Asn Leu Ala Leu Leu
  1               5
```

(2) INFORMATION FOR SEQ ID NO: 14:

(i) SEQUENCE CHARACTERISTICS:
(A) LENGTH: 8 amino acids
(B) TYPE: amino acid
(D) TOPOLOGY: linear (ii) MOLECULE TYPE: protein (xi) SEQUENCE DESCRIPTION: SEQ ID NO: 14:

```
Met Thr Thr Asp Asp Leu Ala Phe
  1               5
```

(2) INFORMATION FOR SEQ ID NO: 15:

(i) SEQUENCE CHARACTERISTICS:
(A) LENGTH: 77 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iii) ANTI-SENSE: NO (vi) ORIGINAL SOURCE:
(A) ORGANISM: Escherichia coli (vii) IMMEDIATE SOURCE:
(B) CLONE: pBO30A-15

(ix) FEATURE:
(A) NAME/KEY: CDS
(B) LOCATION: 1..57
(D) OTHER INFORMATION: /partial
/codon_start= 1
/function= "altered 3'-end"
/EC_number= 6.3.3.3
/product= "DTB synthase"
/gene= "bioD"

(ix) FEATURE:
(A) NAME/KEY: CDS
(B) LOCATION: 54..77
(D) OTHER INFORMATION: /partial
/codon_start= 54
/EC_number= 2.6.1.62
/product= "DAPA synthase"
/gene= "bioA"

(ix) FEATURE:
(A) NAME/KEY: RBS
(B) LOCATION: 45..56
(D) OTHER INFORMATION: /standard_name= "bioA RBS"

(x) PUBLICATION INFORMATION:
(H) DOCUMENT NUMBER: WO 87/01391 B1
(I) FILING DATE: 26-AUG-1986
(J) PUBLICATION DATE: 07-APR-1993

(xi) SEQUENCE DESCRIPTION: SEQ ID NO: 15:

```
TAC ATA AAC CTT GCC TTC GTC GAC GCG TCG ACT CTA GGG TTT ACA AGT       48
Tyr Ile Asn Leu Ala Phe Val Asp Ala Ser Thr Leu Gly Phe Thr Ser
  1               5                  10                  15
```

-continued

```
CGA TTA TGACAACGGA CGATCTTGCC TTT                                    77
Arg Leu


(2) INFORMATION FOR SEQ ID NO: 16:

     (i) SEQUENCE CHARACTERISTICS:
          (A) LENGTH: 18 amino acids
          (B) TYPE: amino acid
          (D) TOPOLOGY: linear

    (ii) MOLECULE TYPE: protein

    (xi) SEQUENCE DESCRIPTION: SEQ ID NO: 16:

Tyr Ile Asn Leu Ala Phe Val Asp Ala Ser Thr Leu Gly Phe Thr Ser
  1               5                  10                  15

Arg Leu


(2) INFORMATION FOR SEQ ID NO: 17:

     (i) SEQUENCE CHARACTERISTICS:
          (A) LENGTH: 125 base pairs
          (B) TYPE: nucleic acid
          (C) STRANDEDNESS: double
          (D) TOPOLOGY: linear

    (ii) MOLECULE TYPE: DNA (genomic)

   (iii) HYPOTHETICAL: NO

   (iii) ANTI-SENSE: NO

    (vi) ORIGINAL SOURCE:
          (A) ORGANISM: Escherichia coli

   (vii) IMMEDIATE SOURCE:
          (B) CLONE: pBO30A-15/985E

    (ix) FEATURE:
          (A) NAME/KEY: -10_signal
          (B) LOCATION: 45..49
          (D) OTHER INFORMATION: /standard_name= "promoter ptac"

    (ix) FEATURE:
          (A) NAME/KEY: promoter
          (B) LOCATION: 1..96
          (C) IDENTIFICATION METHOD: experimental
          (D) OTHER INFORMATION: /function= "promoter ptac"
               /evidence= EXPERIMENTAL

     (x) PUBLICATION INFORMATION:
          (H) DOCUMENT NUMBER: WO 87/01391 B1
          (I) FILING DATE: 26-AUG-1986
          (J) PUBLICATION DATE: 07-APR-1993

    (xi) SEQUENCE DESCRIPTION: SEQ ID NO: 17:

AAGCTTACTC CCCATCCCCC TGTTGACAAT TAATCATCGG CTCGTATAAT GTGTGGAATT     60

GTGAGCGGAT AACAATTTCA CACAGGAAAC AGGATCGGTA CCTTAGGAGG TGACTAGTCA    120

TGGCT                                                                125


(2) INFORMATION FOR SEQ ID NO: 18:

     (i) SEQUENCE CHARACTERISTICS:
          (A) LENGTH: 126 base pairs
          (B) TYPE: nucleic acid
          (C) STRANDEDNESS: double
          (D) TOPOLOGY: linear

    (ii) MOLECULE TYPE: DNA (genomic)

   (iii) HYPOTHETICAL: NO
```

-continued (iii) ANTI-SENSE: NO (vi) ORIGINAL SOURCE:
(A) ORGANISM: Escherichia coli (vii) IMMEDIATE SOURCE:
(B) CLONE: pBO30A-15/16

(ix) FEATURE:
(A) NAME/KEY: promoter
(B) LOCATION: 1..96
(C) IDENTIFICATION METHOD: experimental
(D) OTHER INFORMATION: /function= "promoter ptac"
/evidence= EXPERIMENTAL (ix) FEATURE:
(A) NAME/KEY: RBS
(B) LOCATION: 105..123
(C) IDENTIFICATION METHOD: experimental
(D) OTHER INFORMATION: /evidence= EXPERIMENTAL
/standard_name= "bioB RBS no.16"

(x) PUBLICATION INFORMATION:
(H) DOCUMENT NUMBER: WO 87/01391 B1
(I) FILING DATE: 26-AUG-1986
(J) PUBLICATION DATE: 07-APR-1993

(xi) SEQUENCE DESCRIPTION: SEQ ID NO: 18:

```
AAGCTTACTC CCCATCCCCC TGTTGACAAT TAATCATCGG CTCGTATAAT GTGTGGAATT     60

GTGAGCGGAT AACAATTTCA CACAGGAAAC AGGATCGGTA CCTAAGGAGG TTTACTAGTC    120

ATGGCT                                                               126
```

(2) INFORMATION FOR SEQ ID NO: 19:

(i) SEQUENCE CHARACTERISTICS:
(A) LENGTH: 122 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iii) ANTI-SENSE: NO (vi) ORIGINAL SOURCE:
(A) ORGANISM: Escherichia coli (vii) IMMEDIATE SOURCE:
(B) CLONE: pBO30A-15/9

(ix) FEATURE:
(A) NAME/KEY: promoter
(B) LOCATION: 1..96
(C) IDENTIFICATION METHOD: experimental
(D) OTHER INFORMATION: /function= "promoter ptac"
/evidence= EXPERIMENTAL (ix) FEATURE:
(A) NAME/KEY: RBS
(B) LOCATION: 105..119
(C) IDENTIFICATION METHOD: experimental
(D) OTHER INFORMATION: /evidence= EXPERIMENTAL
/standard_name= "bioB RBS no. 9"

(x) PUBLICATION INFORMATION:
(H) DOCUMENT NUMBER: WO 87/01391 B1
(I) FILING DATE: 26-AUG-1986
(J) PUBLICATION DATE: 07-APR-1993

(xi) SEQUENCE DESCRIPTION: SEQ ID NO: 19:

```
AAGCTTACTC CCCATCCCCC TGTTGACAAT TAATCATCGG CTCGTATAAT GTGTGGAATT     60
```

-continued

```
GTGAGCGGAT AACAATTTCA CACAGGAAAC AGGATCGGTA CCTAAGGAGA CTAGTCATGG    120

CT                                                                   122
```

BIOTECHNOLOGICAL METHOD OF PRODUCING BIOTIN

BACKGROUND OF THE INVENTION

The invention relates to recombinant genetic material for expression of the genes of the biotin metabolic pathway in enterobacteria, microorganisms which contain this recombinant genetic material, and the use of such microorganisms in a biotechnological method of producing biotin. The invention furthermore relates to a method of producing biotin which comprises conversion of dethiobiotin by means of biotin synthase in a cell-free system.

Biotin (vitamin H) is a vitamin which is important for humans and animals and whose deficiency may cause, for example, seborrhoea, dermatitis, loss of appetite and lassitude. Accordingly, biotin is a beneficial additive to human and animal foods.

The production of biotin by methods of synthetic organic chemistry is elaborate and costly. For this reason, increasing attention is being paid to biotechnological methods in which biotin can be synthesized with the aid of microorganisms from low-cost starting materials such as glucose.

*Escherichia coli* (*E. coli*) is a microorganism which is able to synthesize biotin starting from simple carbon sources such as glycerol or glucose (FIG. 1). The genes responsible for biosynthesis of biotin in *E. coli* are present in an operon which has already been cloned and comprises the five genes bioA, bioB, bioC, bioD and bioF (also called bio genes hereinafter) (Gupta et al., Gene 1:331–345; 1977). These genes are transcribed in two different directions by a promoter-operator region which is located between the bioA and bioB genes. Related to the conventional gene map, the bioB, bioF, bioC and bioD genes are on the right and the bioA gene is on the left of the promoter-operator region. The DNA to the left of the promoter-operator region comprises, downstream of the bioA gene, another gene which is called ORFI (ORF=open reading frame) which codes for a polypeptide having 158 amino acids and is transcribed together with the bioA gene (Otsuka et al., J. Biol. Chem., 263:19577–19585; 1988). The function of the latter gene is as yet unknown. Other strains from the family of enterobacteria, for example of the genus Salmonella or Citrobacter, have a biotin operon of *E. coli*-analogous structure (Shiuan and Campbell, Gene 67:203–211; 1988).

Biotechnological methods of producing biotin which are carried out using microorganisms which are transformed with the cloned biotin operon of *E. coli* have already been disclosed. These methods are carried out starting from glucose. EP-B-236 429 describes, for example, microorganisms which are transformed with the biotin operon of *E. coli,* with the host organisms being mutated in their biA/bioR gene.

EP-A-316 229 describes *E. coli* mutants which produce less acetate and have likewise been transformed with the cloned biotin operon.

EP-A-449 724 discloses microorganisms which have been transformed with the biotin operon and additionally have mutations which result in smaller glucose consumption.

EP-A-266 240 furthermore discloses the cloning of the genes responsible for biotin synthesis in *Bacillus sphaericus* and a method, based on this, for producing biotin. This method must, owing to the metabolism of *Bacillus sphaericus,* be carried out starting from costly pimelic acid.

The yields obtained in the biotechnological methods disclosed are, however, as yet unsatisfactory from economic points of view.

SUMMARY OF THE INVENTION

It is therefore an object of the present invention to provide a biotechnological method of producing biotin which makes higher yields of biotin possible and is thus more economic.

This object has been achieved by using DNA fragments and vectors which comprise the bioB, bioF, bioC, bioD and bioA genes or their functionally equivalent genetic variants and mutants from enterobacteria, these genes being organized in a transcription unit.

By transcription unit is meant in this connection a DNA sequence in which the genes are arranged in one direction of transcription and are transcribed under common transcription control into a continuous transcript, where the DNA sequence comprises, besides the relevant genes, also the genetic control elements, such as promoters and ribosome binding sites, which are necessary for gene expression.

By "functionally equivalent genetic variants and mutants" are meant genes which are derived from the wild-type genes of the original organisms, that is to say the enterobacteria, and have base exchanges within the scope of the known degeneracy of the genetic code. Base exchanges of these types can be of natural origin or generated artificially, for example in order to adapt the gene sequence to the preferred codon usage of a particular microorganism in which expression is to take place. The genetic variants and mutants furthermore comprise deletions, insertions and substitutions of bases or codons which leave the gene product of such a modified sequence with its function basically intact. The sequences particularly comprise those which, under the usual hybridization conditions, that is to say at temperatures between 55 and 66° C. and with a salt content of 0.03 to 0.3 M, hybridize with the wild-type sequences, that is to say sequences which have a high degree of homology, for example higher than 70%, with the wild-type sequences.

BRIEF DESCRIPTION OF THE DRAWINGS

FIGS. 6A–6H show the DNA sequence and amino-acid sequence of the genes in the plasmid pBO30A-15/9 coding for biotin biosynthesis together with the genetic control elements (SD: Shine-Dalgarno sequence). Amino acids in italics at the COOH terminus of the bioD15 gene represent substitutions compared with the wild-type sequence of the bioD gene of *E. coli.*

Figure 1:
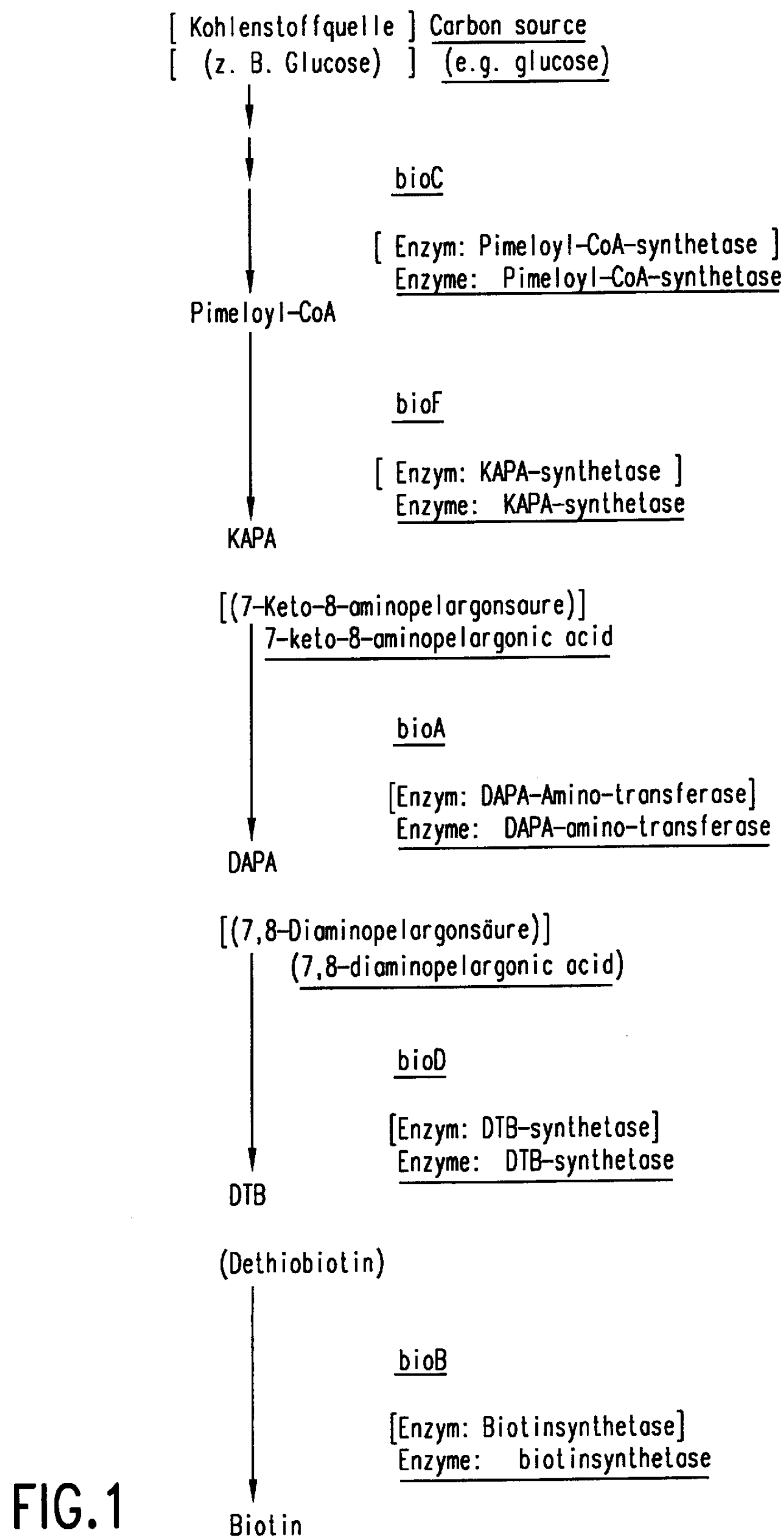
FIG. 1 shows the enzymes of the metabolic pathway of biotin biosynthesis.
Figure 2A:
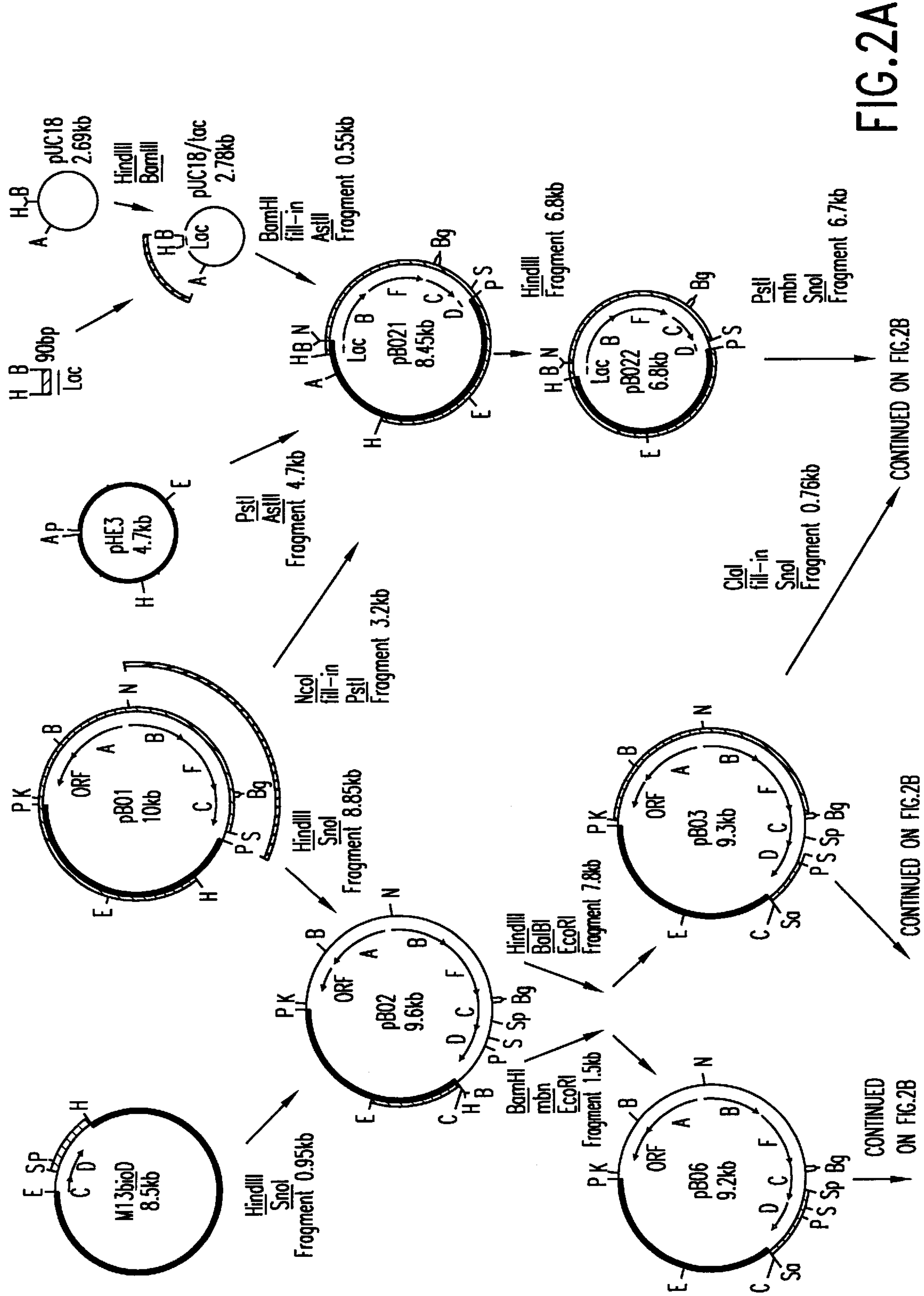
FIG. 2 shows the construction scheme for the plasmid pBO30.
Figure 2B:
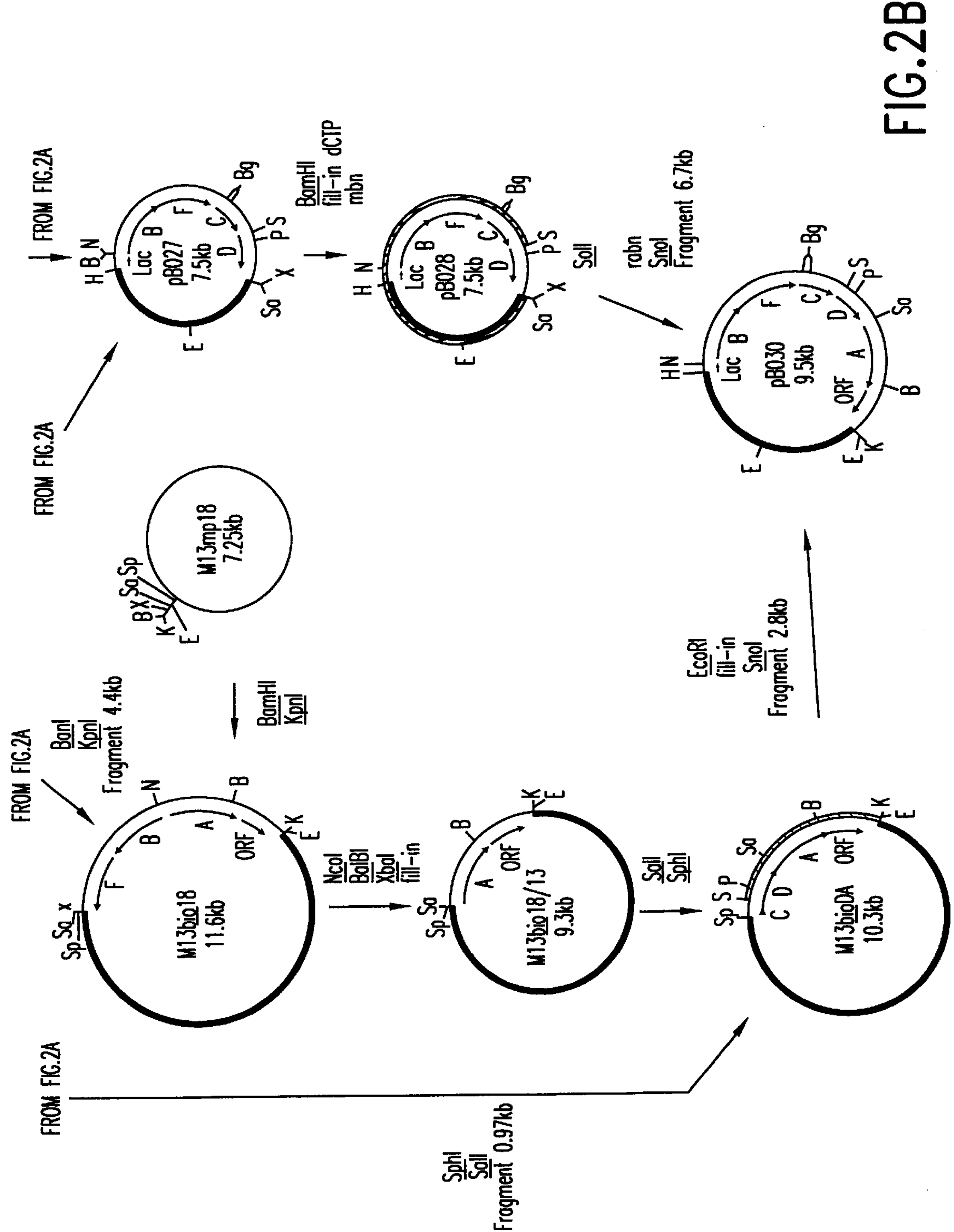
Figure 5:
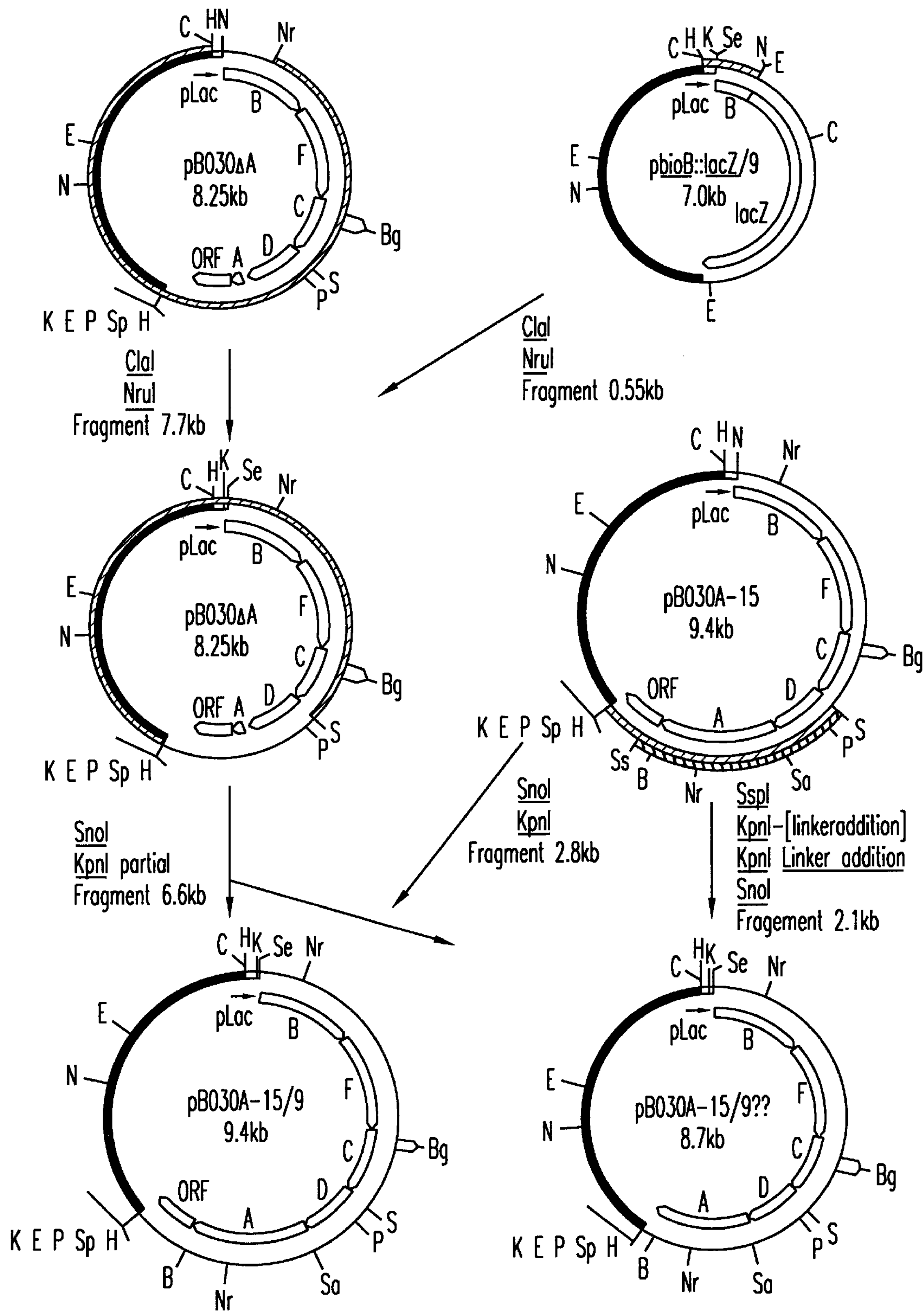
FIG. 5 shows the construction scheme for the plasmids pBO30A-15/9 and pBO30A-15/9ΔorfI.

The meanings in FIGS. 2 and 5 are A: AatII; B: BamHI; Bg: BglII; C: ClaI; E: EcoRI; H: HindIII; K: KpnI; N: NcoI; Nr: NruI; P: PstI; S: SnoI; Sa: SalI; Se: SseI; Sp: SphI; Ss: SspI; and X: XbaI. "Fill-in": filling in of recessive 3' ends with Klenow polymerase; mbn: deletion of protruding 5' or 3' ends with mung bean nuclease; Bal31: progressive deletion of DNA with exonuclease Bal31. The vector content of the plasmids is shown bold. The parts with different shading in the plasmids were used in each case for the subsequent cloning step. Arrows indicate the position and orientation of the bio genes.

To construct the DNA fragments and vectors according to the invention, the genes of the biotin operon are initially expediently isolated from the chromosome of a suitable microorganism and subsequently linked together under the control of gene-regulatory elements such as promoters and ribosome binding sites so that they are present organized in a single transcription unit. Starting material which can be used for isolating the bio genes are bacterial strains from the family of enterobacteria, for example of genus Escherichia, Salmonella or Citrobacter. The starting material is expediently a microorganism of the species *Escherichia coli,* which is characterized best.

The construction of the DNA fragments and vectors according to the invention can start, for example, from a gene bank of a suitable microorganism such as *E. coli,* from which the bio genes or fragments thereof can be isolated and cloned in a known manner by hybridization with labelled oligonucleotides which contain part-sequences of the bio genes. The isolated and cloned bio genes are subsequently linked together by known methods of DNA recombination under the control of a common promoter so that they are present as a single transcription unit. The bio genes are expediently arranged such that the bioA gene is located downstream of the bioB, bioF, bioC and bioD genes, which are already present in a transcription unit in the wild-type operon of *E. coli.* The bioB gene encodes, in biotin synthase, the key enzyme of the entire biotin synthesis pathway because conversion of dethiobiotin to biotin by biotin synthase as yet represents the rate-determining step of the 5-stage biotin synthesis pathway. The bioB gene is therefore expediently the first gene within the transcription unit, because optimal expression of this gene can take place because of the vicinity to the promoter (FIGS. 2, 4, 5 and 6).

The second transcription unit in the wild-type biotin operon of *E. coli,* which contains the bioA gene, additionally comprises another gene, ORFI, which codes for a polypeptide having 158 amino acids. Experiments carried out with expression plasmids in which no ORFI gene is present show that this gene is not essential for biotin biosynthesis under normal fermentation conditions. However, it cannot be ruled out that this polypeptide, whose function is as yet unknown, also plays a part in biotin synthesis under certain conditions. Although the presence of the ORFI gene in the DNA fragments according to the invention is therefore not absolutely necessary, in an expedient embodiment the transcription unit with the bio genes additionally also comprises the ORFI gene. (FIGS. 2, 5 and 6).

The bio genes in the DNA fragments and vectors according to the invention are advantageously not under the control of the natural biotin promoter of *E. coli.* On the contrary, the bio genes are, to improve transcription, expediently placed under the control of a strong foreign promoter. The choice of the promoter depends on the desired expression conditions, for example on whether constitutive or induced expression is required, or on the microorganism in which expression is to take place. Examples of suitable promoters are the promoters $P_L$ and $P_R$ of the phage lambda (compare Schauder et al., Gene 52:279–283; 1987), the promoter pxylS of the TOL plasmid of *Pseudomonas putida* with the neighbouring regulator gene xylR (Franklin et al., J. Bacteriol. 154:676–685; 1983), the trc promoter (Amann et al., Gene 69:301–315; 1988), the trp promoter (Amann et al., Gene 25:167–178; 1983), the promoter pdegQ from *Bacillus subtilis,* which is active in the stationary phase (Dahl et al., J. Bacteriol. 173:1539–1547; 1991) and the lacUV5 promoter (Amann et al., Gene 25:167–178; 1983). The promoter preferably chosen is the tac promoter, a hybrid of the trp promoter and the lacUV5 promoter of *E. coli,* which can be employed as constitutive or inducible promoter (Russell and Bennett, Gene 20:231–243; 1982).

It has additionally been found that expression of the bioA gene in the preferred arrangement described above can be further improved when the distance between the bioD and bioA genes which are consecutive in the transcription unit is as short as possible, that is to say preferably less than 50 bp (base pairs). It has been found, surprisingly, that expression is particularly high when the sequence of the 3' end of the bioD gene, which codes for the COOH terminus of dethiobiotin (DTB) synthetase, simultaneously contains the ribosome binding site of the following bioA gene. It is advantageous for there simultaneously to be an overlap of the reading frames of the bioD and bioA genes. Such a situation can be achieved by fusing the 5' end of the bioA gene together with its ribosome binding site to the bioD gene in such a way that its 3' end is substituted by the sequence with the ribosome binding site upstream of the bioA gene and, where appropriate, the 5' terminus of the bioA gene (FIGS. 3 and 6; Seq ID No: 1, 6 and 8–16). This effect is all the more surprising since with such a fusion the COOH terminus of DTB synthetase can be exchanged without the enzyme losing its activity. Similar overlaps are also found in the wild-type biotin operon of *E. coli* between the reading frames of the bioB, bioF, bioC and bioD genes.

Expression of the bioB gene can be further optimized by optimizing the ribosome binding site in front of the bioB gene. This expediently entails starting from a construct in which the bioB gene is already under the control of a strong promoter, for example of the tac promoter. Optimization of the ribosome binding site of the bioB gene, that is to say alteration of the Shine-Dalgarno sequence and its distance from the 5' end of the structural gene, can take place by the usual methods of DNA recombination. The influence of a particular ribosome binding site on translation can be determined in a manner known per se, for example by gene fusion of the gene to be tested with the lacZ gene and subsequent assay with the chromogenic substrate 5-bromo-4-chloro-3-indolyl-β-D-galactopyranoside (X-Gal).

DNA fragments which comprise the bio genes in a transcription unit can be incorporated into a large number of vectors by known techniques of DNA recombination. For example the plasmids pBO30A-15/9 (FIGS. 5 and 6, seq ID No: 1 and 6; Example 1.5.2) and pBO47 (Example 1.7) were obtained in this way. Plasmid pBO30A-15/9 was deposited on 28.9.1992 at the Deutsche Sammlung für Mikroorganismen und Zellkulturen GmbH, D-3300 Braunschweig, Mascheroderweg 1b, in *E. coli* XL1-Blue and *E. coli* BM4062 under deposit numbers DSM 7246 and 7247 respectively, and on 17.9.1993 in *E. coli* ED8767 under deposit number DSM 8554. Plasmid pBO47 was deposited on 17.9.1993 at the Deutsche Sammlung für Mikroorganismen und Zellkulturen GmbH in *Agrobacterium/Rhizobium* sp HK4 under the deposit number DSM 8555.

Depending on the nature of the chosen vectors, the genes for the enzymes of the biotin synthesis pathway can be expressed in various organisms. Suitable vectors are both vectors with a specific host spectrum and vectors with a broad host spectrum ("broad host range"). Examples of vectors with a specific host spectrum, for example for *E. coli,* are pBR322 (Bolivar et al., Gene 2:95–113; 1977), pUC18/19 (Yanisch-Perron et al., Gene 33:103–119; 1985), pK18/19 (Pridmore, Gene 56:309–312; 1987) and pRA95 (obtainable from Nycomed Pharma AS, Evidovre, Denmark).

Vectors which can be employed as "broad host range" vectors are all those suitable for Gram-negative bacteria. Examples of such "broad host range" vectors are pRK290 (Ditta et al., Proc. Natl. Acad. Sci. USA 77:7347–7351; 1980), pKT240 (Bagdasarian et al., Gene 26:273–282; 1983), derivatives of pRK290 such as pLAFR1 (Long et al., Nature 298:485–488; 1982) and pRK290X (Alvarez-Morales et al., Nucl. Acid. Res. 14:4207–4227; 1986), derivatives of pKT240 such as pMMB66EH (Fürste et al., Gene 48:119–131; 1986) or pGSS33 (Sharpe, Gene 29:93–102; 1984).

To produce the producer strains for the fermentation, that is to say the strains for biotin production, the DNA fragment according to the invention must be introduced into the desired host strains suitable for expression. Microorganisms suitable for the expression of the bio genes, preferably strains with a wide substrate spectrum, are, for example, enterobacteria, preferably of the genus Escherichia, or microorganisms of the genus Rhizobium, Agrobacterium, Rhizobium/Agrobacterium, Acinetobacter, Azotobacter, Pseudomonas and Comamonas. Particularly preferred microorganisms are of the species *E. coli,* Rhizobium/Agrobacterium sp., HK4 (as described in EP-B 158 194), *Pseudomonas mendocina, Pseudomonas aeruginosa* or *Acinetobacter calcoaceticus.* The microorganisms can contain the DNA fragment according to the invention either on a vector molecule or integrated into their chromosome. The introduction of the DNA fragment into the microorganisms can take place, for example, by transformation or conjugation. The selected microorganisms are expediently transformed in a manner known per se with vectors which contain the DNA fragments according to the invention. Examples of suitable producer strains are *E. coli* XL1-Blue, *E. coli* BM4062 and *E. coli* ED8767, each containing plasmid pBO30A-15/9 (DSM 7246, DSM 7247 and DSM 8554) and Agrobacterium/Rhizobium sp EK4 with plasmid pBO47 (DSM 8555).

The transformed host strains are expediently isolated from a selective nutrient medium to which is added an antibiotic against which the host strains are resistant owing to a marker gene present on the vector or DNA fragment.

The biotechnological production of biotin takes place using the microorganisms which contain the DNA fragments or vectors according to the invention. The method of producing biotin is carried out in a conventional way in cultures starting from a carbon source which is suitable as growth substrate for the particular microorganism and is finally converted into biotin. Particularly suitable as carbon source are simple sugar molecules, for example glucose or glycerol. Accordingly, it is possible to use as growth media commercially available media such as for example, nutrient yeast broth (NYB: nutrient broth No. 2, Oxoid, 25 g/l; yeast extract, Oxoid, 5 g/l) or glycerol and glucose minimal media.

The fermentation, that is to say the production of biotin, is preferably carried out as so-called "fed-batch method", that is to say in a batch fermentation into which is fed, continuously or at intervals, a volume stream containing fresh nutrients, although no culture solution is drawn off. In a method of this type, preferably a glycerol solution is fed in at a variable inflow rate adapted to the particular biomass growth as "feed".

The fermentation takes place within the pH and temperature ranges physiologically tolerated by the particular microorganisms. It is expedient for the pH to be within a range from 6 to 8 and for the temperature to be within a range from 20 to 45° C.

The biotin yield can be further improved by varying the nutrients in the medium and by adapting the fermentation conditions to the particular microorganism in a conventional way.

The present invention furthermore relates to a method of producing biotin which comprises conversion of dethiobiotin to biotin in a cell-free system using the enzyme biotin synthase, wherein the conversion is carried out in the presence of thiamine pyrophosphate, NADPH, S-adenosylmethionine, $Fe^{2+}$ ions, cysteine and at least one other amino acid from the group consisting of asparagine, aspartic acid, glutamine and serine.

Biotin synthase can be employed either in purified form or in the form of cell extract. The cell extract or the purified biotin synthase is expediently obtained from a strain with high-level expression of biotin synthase, for example from *E. coli* XL1-Blue with the plasmid pBO30A-15/9 (DSM 7246). The production of the cell extract and, where appropriate, the purification of biotin synthase can take place by methods customary in biochemistry, for example by homogenization of the cells, gel filtration, ammonium sulphate fractionation and ion exchange chromatography.

It has been found that the conversion of dethiobiotin to biotin in a cell-free system using biotin synthase can be carried out with good yields only when the conversion takes place with the addition of cofactors and amino acids.

The cofactors necessary for the conversion comprise S-adenosylmethionine (SAM), thiamine pyrophosphate (TPP), reduced nicotinamide adenine dinucleotide phosphate (NADPH) and $Fe^{2+}$ ions. The cofactors are expediently added in concentrations of 1 to 500 $\mu$M. It is also expedient to add to the mixture dithiothreitol (DTT) in a concentration of 0.1 to 10 mM.

Amino acids required for the conversion are cysteine as sulphur donor and at least one other amino acid from the group consisting of asparagine, aspartic acid, glutamine and serine. Aspartic acid is expediently added as aspartate. Cysteine is expediently added in concentrations of 10 to 500 $\mu$M, and the other amino acids in concentrations of 1 to 50 mM.

Figure 7:
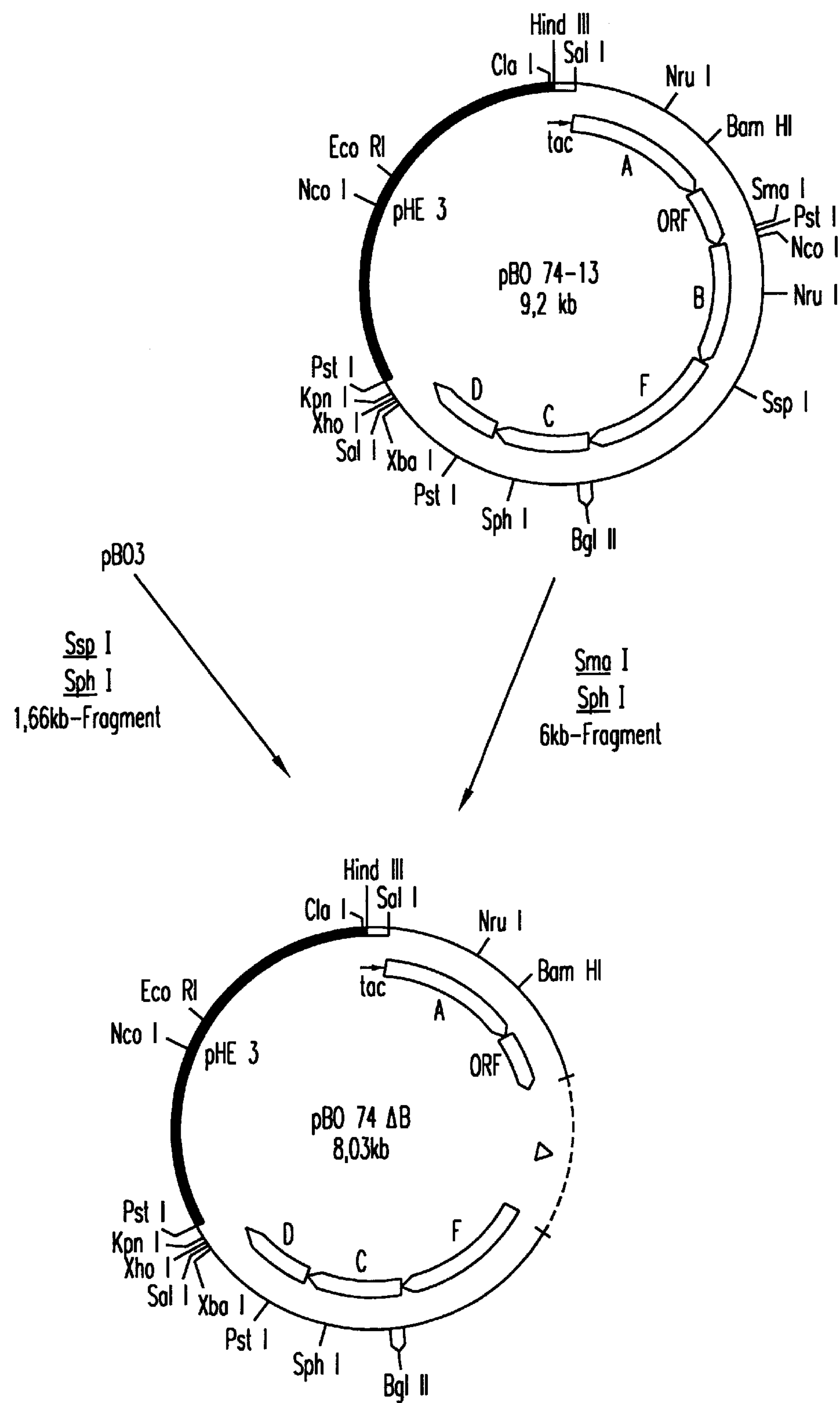
FIG. 7 shows the construction scheme for plasmid pBO74ΔB starting from the plasmids pBO74-13 and pBO3; arrows indicate the position and orientation of the tac promoter and of the bio genes. The vector content of the plasmids is shown bold. Dashed lines indicate the extent of deletion of the bioB gene.

It has furthermore been found that the conversion of dethiobiotin to biotin takes place on use of a purified biotin synthase only in the presence of flavodoxin and ferredoxin (flavodoxin)-NADP$^+$ reductase. It is therefore expedient to add, especially when the biotin synthase is not employed in the form of a cell extract, flavodoxin and ferredoxin (flavodoxin)-NADP$^+$ reductase for the conversion. Flavodoxin and ferredoxin(flavodoxin)-NADP$^+$ reductase (EC No. 1.18.1.2) are known proteins which can be obtained in a known manner, for example by ammonium sulphate fractionation and subsequent ion exchange chromatography and gel filtration chromatography, independently of the expression of biotin synthase from cell extracts of *E. coli*. Thus, it was possible to isolate flavodoxin and ferredoxin (flavodoxin)-NADP$^+$ reductase for example both from *E. coli* XL1-Blue with the plasmid pBO30A-15/9 (DSM 7246), which displays high-level biotin synthase expression, and from *E. coli* XL1-Blue with the plasmid pBO74ΔB (DSM 7245), in which the biotin synthase gene bioB is deleted (FIG. 7). Plasmid pBO74ΔB was deposited in *E. coli* XL1-Blue on 28.9.1992 at the Deutsche Sammlung für Mikroorganismen und Zellkulturen GmbH, D-3300 Braunschweig, Mascheroderweg 1b, under deposit number DSM 7245.

It has additionally been found that, besides biotin synthase, other proteins are necessary for the conversion of dethiobiotin to biotin, and these are normally present in an *E. coli* cell extract. These proteins are present in a protein fraction obtainable by ammonium sulphate precipitation at 45% saturation with ammonium sulphate from *E. coli* cell extracts. As the isolation of a protein fraction of this type from *E. coli* XL1-Blue with the plasmid pBO74AB (DSM 7245) shows, the expression of biotin synthase is not necessary for the presence and for obtaining these proteins. The precipitate obtained after the ammonium precipitation can be further purified, for example, by chromatographic methods such as ion exchange chromatography and gel filtration chromatography. It is therefore expedient to add to the mixture for the conversion of dethiobiotin to biotin, especially when biotin synthase is not employed in the form of a cell extract, a protein fraction obtainable as described above.

The conversion takes place in a suitable buffer system, expediently within the pH and temperature ranges in which the enzymes are physiologically active, preferably in a pH range from 6 to 9 and at a temperature between 4 and 50° C.

The present invention is explained further in the following examples.

General methods

Restriction endonucleases were employed with 3 to 5 units/μg DNA in accordance with the manufacturers' instructions. Labelling and phosphorylation of DNA linkers (purchased from Boehringer Mannheim, FRG) for incorporation of restriction cleavage sites, and of synthetic oligonucleotides (purchased from Microsynth, Windisch, CH), for example for use as probes for DNA/DNA hybridizations and as "primers" for sequencing reactions, took place with T4 polynucleotide kinase (Boehringer Mannheim, FRG) as described by Sambrook et al. (Molecular Cloning: A laboratory manual. 2nd edition, Cold Spring Harbour Laboratory, Cold Spring Harbour, N.Y.; 11.31 and 5.68; 1989). Ligation reactions took place with T4 DNA ligase in accordance with the manufacturers' instructions.

DNA sequencings took place by the chain-termination method of Sanger et al. (Proc. Natl. Acad. Sci. USA 94:5463–5467; 1977). All sequence reactions were carried out with the Sequenase kit from United States Biochemicals (Cleveland, Ohio, USA) in accordance with the manufacturer's protocol. Sequenase (Version 2.0, a genetically engineered T7 DNA polymerase) yielded uniform, readily readable DNA sequences over more than 600 bp; it was possible easily to break up compressions in GC-rich DNA regions when the nucleotide dITP was used in place of dGTP. The templates used for the sequence reaction were, as a rule, the single-stranded forms of the vectors M13mp18/19 (Yanisch-Perron et al., 1985, ibid.) or pBluescript KS$^+$/SK$^+$ (ap$^R$ lacZ'; obtainable from Stratagene, La Jolla, Calif.), which were isolated as described by Messing (Methods Enzymol. 101:20–79; 1983). For sequencing double-stranded plasmid DNA, the plasmid DNA was purified by CsCl gradients or "Gene Clean" (BIO 101, La Jolla, Calif.). α[$^{35}$]-dATP (NEN-Du Pont, NEG-034H) was used as radioactively labelled nucleotide. The fractionation by electrophoresis took place either on the customary 4% or 6% bis/acrylamide gels with 7 M urea and 1×TBE buffer (90 mM Tris, 90 mM boric acid, 2.5 mM EDTA), or else on gels from 5% HydroLink Long Ranger (AT Biochem, Malvern, Pa., USA, via Chemie Brunschwig, Basel) with 7 M urea and 1.2×TBE buffer. The gels were 550 mm long and 0.2 mm thick; the electrophoresis took place in an LKB Macrophor apparatus with thermostat at a voltage of 2100 V and a temperature of 60° C. The gels were then dried on Whatman 3 MM paper and autoradiographed with Fuji RX or Amersham Hyperfilm βmax X-ray film.

The isolation of extrachromosomal DNA took place either in relatively small amounts by the "rapid alkaline SDS" ("Miniprep") method of Birnboim and Doly (Nucl. Acid. Res. 7:1513–1523; 1979), or, to isolate larger amounts, by caesium chloride density gradient centrifugation by a modified method of Clewell and Helsinki (Proc. Natl. Acad. Sci. USA 42:1159–1166; 1969). Alternatively, QIAGEN packs from DIAGEN, Düsseldorf (FRG) were used.

To transform *E. coli* with plasmid DNA, the cells were made competent by the method of Cohen et al. (Proc. Natl. Acad. Sci. USA 69:2110–2114; 1972) in 50 mM $CaCl_2$. Transformation with plasmid DNA and selection of plasmid-harbouring clones took place as described by Sambrook et al. (1989; ibid. 1.82–1.84).

EXAMPLE 1

Cloning of the *E. coli* biotin operon in a single transcription unit 1.1 Construction of pBO1 and M13bioD For the cloning of the bio genes, the chromosomal DNA was isolated from *E. coli* DSM 498 (K12 "wild-type"; Deutsche Sammlung für Mikroorganismen und Zellkulturen GmbH). The isolation took place essentially as described by Hahn and Hennecke (Mol. Gen. Genet. 193:46–52; 1984). Subsequently, 2 μg of complete DNA from *E. coli* DSM 498 were cut with the restriction enzyme PstI. The DNA fragments were fractionated by electrophoresis in a horizontal 0.7% agarose gel in a conventional way (Sambrook et al., 1989, ibid.; 6.19 to 6.9) and transferred onto "Gene Screen" membranes (nylon membranes from NEN-Du Pont) (Southern, J. Mol. Biol., 98:503–517; 1975). The DNA was fixed on the dried filters by incubation at 80° C. in a vacuum oven for two hours. To identify DNA fragments with the bio operon, a 25 nucleotide-long synthetic oligonucleotide with the sequence 5'-GGCTCACCGCCCACGCTGGACATTG-3', corresponding to a sequence from the 5' end of the bioB gene (Otsuka, A. J., Dissertation, University of California, San Diego, Calif.; 1978), was hybridized as probe with the filter-bound DNA. For this purpose, initially 40 pmol of this oligonucleotide were end-labelled with T4 polynucleotide kinase and γ-[$^{32}$P]-ATP (75 μCi). The hybridization of the filter-bound DNA with the radioactively labelled probe took place as described by Sambrook et al., (1989, ibid., 9.52–9.55). For this purpose, the DNA was initially prehybridized in 5×Denhardt's solution (1×Denhardt's solution: 0.02% bovine serum albumin, 0.02% Ficoll, 0.01% polyvinylpyrrolidone), 6×SSC buffer (1×SSC: 150 mM NaCl, 15 mM sodium citrate, pH 7.2) and 150 μg/ml salmon sperm DNA for 2 h, subsequently hybridized in 2×Denhardt's solution, 6×SSC, 0.5% SDS, 150 μg/ml salmon sperm DNA for 18 h, and washed for 2 h and finally washed four times in 2×SSC, 0.1% SDS for 30 min each time. The temperature was 65° C. in all steps. The labelled oligonucleotide hybridized on this "Southern blot" with a 5.4 kb-long PstI fragment.

To clone this 5.4 kb PstI fragment with the biotin operon, initially 50 μg of the complete DNA from *E. coli* DSM 498 were cut with PstI and fractionated on a 0.7% agarose gel as above. Fragments with a size of 4.5 kb to 6.5 kb were cut out of the gel and isolated by electrodialysis in dialysis tubes. Approximately 0.6 μg of these fragments were ligated with 0.6 μg of the PstI-cut vector pHE3 (Hennecke et al., Gene 19:231–234; 1982). This vector contains the gene for chloramphenicol resistance ($Cm^R$), the ColE1 replicon from pACYC184 (Chang and Cohen, J. Bacteriol., 134:1141–1156; 1978) and the *E. coli* gene pheS for phenylalanine-tRNA synthetase, which has a PstI site.

0.2 ml of competent cells of *E. coli* RR28 (Hennecke et al., 1982, ibid.) in 50 mM $CaCl_2$ were transformed with this ligation mixture. *E. coli* RR28 has a mutated pheS gene (pheS12) in the chromosome and is therefore resistant to p-fluorophenylalanine (pFphe) in the growth medium. On the other hand, when RR28 harbours the plasmid pRE3 with the pheS wild-type gene, the strain is sensitive to pFphe. Insertion of DNA fragments into the PstI cleavage site of pEE3 interrupts the pheS wild-type gene; RR28 with a recombinant plasmid is therefore pFphe-resistant ($pFphe^R$). Transformed cells were plated on pFphe minimal medium (7.1 g/l $Na_2HPO_4$, 13.6 g/l $KH_2PO_4$, 0.014 g/l $CaCl_2 \times 2H_2O$, 0.25 g/l $MgSO_4$, 1.58 g/l $(NH_4)_2SO_4$, 15 g/l agar, 4 g/l glucose, 0.005 g/l thiamine, 0.05 g/l leucine, 0.05 g/l proline, 0.2 g/l D,L-p-fluorophenyl-alanine, 0.02 g/l chloramphenicol; Hennecke et al., 1982, ibid.) and about 2500 $Cm^R$ $pFphe^R$ clones which contained the plasmid pHE3 ($Cm^R$) with an insert in the pheS gene ($pFphe^R$) were isolated. 600 of these clones were replica plated onto nitrocellulose filters which were lying on nutrient agar (NA) plates (NA: Blood Agar Base (Oxoid), 40 g/l; yeast extract (Oxoid), 5 g/l) containing 20 μg/ml Cm. Filters on which colonies grew (3–5 m diameter) were treated as described by Grunstein and Hogness (Proc. Natl. Acad. Sci. USA 72:3961–3965; 1975) in order to lyse the cells and bind the liberated DNA. Filters with the lysed and fixed *E. coli* cells were hybridized with the above-described 25 nucleotide-long and $^{32}P$-labelled bioB oligonucleotide. The hybridization took place in accordance with the modifications for colony hybridization described by Sambrook et al. (1989, ibid., 11.00), that is to say prehybridization, hybridization and the first washing step took place in 4×Denhardt's solution, 6×SSC, 100 μg/ml salmon sperm DNA, followed by washing 6×in 2×SSC. The temperature was 65° C. 3 clones bound the bioB oligonucleotide; the plasmid pBO1 with the 5.4 kb-long PstI fragment (FIG. 2) was isolated from one of these clones. Restriction analyses and comparison with published data (Szybalski and Szybalski, Gene 19:93–103; 1982) showed that pBO1 contained all the genes of the biotin operon with the exception of bioD.

To clone the bioD gene, a probe with parts of the bioC and bioD genes consisting of a 520 bp-long SphI/PstI fragment from pBO1 was used. This fragment was isolated from an agarose gel and 0.2 μg of the isolated fragment was radioactively labelled by "nick translation" with DNA polymerase I (Boehringer Mannheim, FRG; holoenzyme from *E. coli;* this so-called "Kornberg polymerase" was used together with DNase I) and 25 μCi of α-[$^{32}P$]-dATP (NEN-Du Pont, NEG-012H) (Sambrook et al., 1989, ibid. 10.8.). The hybridization of this probe with restriction fragments of the *E. coli* DSM 498 chromosome generated by SspI on a "Southern blot" as described above showed, on the one hand, the 1.6 kb SspI fragment with bioF and bioC known from pBO1 and, on the other hand, a 1.1 kb SspI fragment with bioD and sequences of the adjacent uvrB gene (Sancar et al., Cell, 28;523–520; 1982).

To clone the 1.1 kb SspI fragment, once again a partial gene bank was set up. For this purpose, 30 μg of DNA from *E. coli* DSM 498 were cut with SspI and fractionated on a 0.7% agarose gel. Fragments with a size from 0.9 kb to 1.3 kb were cut out and isolated by electrodialysis. 0.5 μg of these fragments was ligated with 0.5 μg of the SmaI-cut phage vector M13mp19 (Yanisch-Perron et al., 1985, ibid.). This ligation mixture was used to transfect *E. coli* JM109 (Yanisch-Perron et al., 1985, ibid.) by the method of Messing (Methods Enzymol., 101:20–79; 1983). 150 phage clones with the insert ($LacZ^-$ phenotype) were isolated and grown in NYB medium. After the *E. coli* cells had been spun down, the phages in 50 μl of each of the supernatants were applied using a Schleicher & Schüll "minifold I" apparatus as "dot blot" to a nitrocellulose filter (Schleicher & Schüll BA 85). To denature the phages, the filters were treated with 0.1 M NaOH/1.5 M NaCl buffer for 5 min and subsequently neutralized with 0.5 M tris-HCl, pH 7.5/2.5 M NaCl (5 min). The DNA was fixed on the filter by incubation at 80° C. (2 h). The filter was hybridized as described (Sambrook et al., 1989, ibid., 9.52–9.55) with the radioactively labelled 520 bp-long SphI/PstI fragment at 60° C. In this way the phage clone M13bioD with the above-described 1.1 kb SspI fragment which contains the bioD gene was identified (FIG. 2).

1.2 Construction of pBO2

In each case 0.5 μg of the plasmid pBO1 and 0.5 μg of the phage M13bioD were cut with the restriction enzymes Snol and HindIII and religated in one mixture. After transformation of *E. coli* RR28 with this mixture, recombinant plasmids were examined by restriction analysis. One plasmid was selected, pBO2 (FIG. 2), in which one approximately 1.5 kb-long Snol/HindIII fragment of pBO1 which contains part of the bioD gene and non-essential sequences of the vector pHE3 is replaced by a 0.95 kb-long SnoI/HindIII fragment from M13bioD. Analysis showed that the plasmid pBO2 contained the complete bio operon as present in *E. coli* together with sequences of the uvrB promoter (Sancar et al., Cell 28:523–530; 1982) downstream of bioD.

1.3 Construction of pBO3 and pBO6

It was observed that *E. coli* RR28 with pBO2 grows less well and forms distinctly smaller colonies on NA plates than with pBO1. The possible reason for this was the uvrB sequences in pBO2. To delete these uvrB sequences, 20 μg of pBO2 DNA were cut with HindIII and taken up in 150 μl of Bal31 buffer (600 mM NaCl, 12.5 mM $MgCl_2$, 12.5 mM $CaCl_2$, 1 mM EDTA, 20 mM tris-HCl, pH 7.2). Then, for stepwise truncation of the linear plasmids Bal31 (from *Alteromonas espejiani,* Boehringer Mannheim, FRG) was added. After incubation at 30° C. for 3, 6, 9, 12 and 15 min, aliquots each of 30 μl were removed and the Bal31 reaction was stopped by adding in each case 2 μl of 0.5 M EGTA (ethylene glycol-bis-(2-aminoethyl) tetraacetic acid), pH 7.5, and subsequent phenol extraction. The aliquots were then taken up in 40 μl of mung bean nuclease buffer (30 mM sodium acetate, 50 mM NaCl, 1 mM $ZnCl_2$, 5% glycerol, pH 4.6) and treated with mung bean nuclease (Boehringer Mannheim, FRG) at 37° C. for 10 min to delete unpaired single-strand ends and generate non-specific blunt ends.

The treatment with Bal31 deletes not only the uvrB sequences but also essential sequences of the vector pHE3. For this reason, the truncated pBO2 plasmids were cut after the treatment with mung bean nuclease with EcoRI in order to delete the part of the vector DNA of pHE3 which was truncated by Bal31. The original vector sequence was then regenerated by ligating the treated pBO2 plasmid to a 1.5 kb DNA fragment which was isolated from pBO2 after restriction with BamHI, treatment with mung bean nuclease and another restriction with EcoRI and which has the previously deleted essential vector sequences of pEE3. Since this ligation resulted in complete regeneration of the Cm resistance of the vector, intact plasmids can be identified by their property of conferring resistance to Cm.

*E. coli* RR28 was transformed with the ligation mixtures and plated on NA plates containing 20 μg/ml Cm. Small, slow-growing colonies as are typical of pBO2, and large, normally growing colonies were observed. The number of large colonies per pBO2 aliquot increased with the duration of the Bal31 incubation.

Plasmid DNA was isolated from 22 normally growing colonies and examined by restriction analysis and sequence analysis. The plasmids pBO3 and pBO6 in which about 330 bp and 410 bp, respectively, of the uvrB region were deleted but which still had the complete bioD gene were obtained in this way.

1.4 Cloning of the bio genes in a transcription unit 1.4.1. Construction of pBO22: tac promoter in front of bioB To incorporate a suitable promoter in front of the bioB gene, the unwanted wild-type promoter in front of the bioBFCD genes must be deleted. This can take place by cutting with NcoI, which simultaneously exposes the start codon of the bioB gene. In the present case, the promoter chosen was the tac promoter (Russell and Bennett, 1982, ibid.) because it can be employed as constitutive or inducible promoter and has very good activity not only in *E. coli* but also in many other Gram-negative bacteria.

A DNA fragment with the tac promoter with HindIII and BamHI ends was purchased from Pharmacia-LKB (Uppsala, Sweden) and inserted into the HindIII and BamHI-cut plasmid pUC18 (Yanisch-Perron et al., 1985, ibid.). The plasmid pUC18/tac (FIG. 2) resulted. 8 μg of this plasmid were then cut with BamHI and, to fill in the recessive 3' ends, incubated with Klenow polymerase, (DNA polymerase I from *E. coli;* Boehringer Mannheim FRG) in Klenow polymerase buffer (20 mM tris-HCl, pH 7.5, 10 mM $MgCl_2$, 6 mM β-mercaptoethanol) with the addition of 100 μM DATP, dGTP, dCTP and dTTP in each case. A second restriction with AatII was subsequently carried out. It was possible in this way to isolate a 0.55 kb-long DNA fragment having the tac promoter.

A 3.2 kb fragment with the bioB, bioF, bioC genes and the 5' end of the bioD gene was isolated from pBO1. For this purpose, 8 μg of pBO1 were cut with NcoI and subsequently treated, to fill in the recessive 3' ends, with Klenow polymerase as above. A second restriction with PstI was subsequently carried out, followed by isolation of the required 3.2 kb fragment. Finally, 4 μg of the vector pHE3 were cut with PstI and AatII, and the P15A replicon from pHE3 (Hennecke et al., 1982, ibid.) was isolated.

These three fragments were treated for ligation of the protruding and blunt ends in one mixture in equimolar amounts with T4 DNA ligase (Boehringer Mannheim, FRG), there being in each case ligation of the protruding ends of PstI with PstI and of AatII with AatII and the blunt ends, after the treatment with Klenow polymerase, of BamHI and NcoI. The BamHI and NcoI cleavage sites are regenerated in the ligation of the BamHI end filled in using Klenow polymerase to the NcoI end treated in the same way. *E. coli* RR28 was transformed with this ligation mixture and selected for $Cm^R$. The plasmid DNA from transformants with $Cm^R$ was examined by restriction analysis. The plasmid pBO21 (FIG. 2) in which the tac promoter is located in front of the bioB gene was obtained in this way. Deletion of a 1.5 kb-long HindIII fragment from pBO21 which has non-essential sequences from the plasmid vectors pHE3 and pUC18 finally resulted in pBO22 (FIG. 2).

1.4.2. Construction of pBO27 and pBO28

5 μg of pBO22 were cut with PstI, and the protruding PstI end was truncated to a blunt end by treatment with mung bean nuclease. It was then cut with SnoI, and the resulting 6.8 kb-long DNA fragment was isolated. A 0.76 kb DNA fragment with the 3' end of the bioD gene was isolated from 5 μg of pBO3 after restriction with ClaI, filling in the protruding ClaI ends using Klenow polymerase and restriction with SnoI. The two DNA fragments were ligated using T4 DNA ligase and then *E. coli* was transformed with the ligation mixture. After selection on chloramphenicol, the plasmid pBO27 was obtained from the transformants with $Cm^R$ after restriction analysis. This plasmid contains the tac promoter together with the bioB, bioF, bioC genes and complete bioD gene in a transcription unit (FIG. 2).

To delete the BamHI cleavage site in pBO27, 5 μg of pBO27 were cut with BamHI, incubated with Klenow polymerase and the nucleotide dGTP as described above, and then treated with mung bean nuclease. Religation of this DNA with T4 DNA ligase and transformation of *E. coli* DH5 (Hanahan, J. Mol. Biol. 166:557–580; 1983) resulted in plasmid pBO28 in which the BamHI cleavage site is deleted, while the NcoI cleavage site is retained (FIG. 2).

1.4.3 Construction of M13bio18 and M13bio18/13

To delete the unwanted wild-type promoter in front of the bioA gene, initially a 4.4 kb fragment with the bioB, bioF, bioA and ORFI genes was isolated by restriction of 5 μg of pBO3 with BglII and KpnI. 0.5 μg of this fragment was ligated to 0.5 μg of the BamHI- and KpnI-cut phage vector M13mp18 (Yanisch-Perron et al., 1985, ibid.). After transformation of *E. coli* JM109 (Yanisch-Perron et al., 1985, ibid.) with this ligation mixture, recombinant phage clones which had an insert were identified as described by Messing (1983, ibid.); double-stranded phage DNA from such clones was isolated and examined by restriction analysis. In this way, the phage M13bio18 with the required 4.4 kb fragment was obtained (FIG. 2).

25 μg of double-stranded DNA of the phage M13bio18 were linearized by restriction with NcoI, taken up in 160 μl of Bal31 buffer and, subsequently, Bal31 was added to delete the bioA promoter. Aliquots each of 25 μl were removed after incubation at room temperature for 20, 40, 60, 80, 100 and 120 seconds, and the Bal31 reaction was stopped by adding 2 μl of 0.5 M EGTA, pH 7.5, and phenol extraction. In each case 3 aliquots were combined and cut with XbaI in order to delete the bioB and bioF genes. Subsequently, the DNA was treated with Klenow polymerase as above in order to fill in protruding 5' ends to blunt ends. The DNA treated in this way was religated, and *E. coli* JM109 was transformed with the ligated DNA. Single-stranded DNA was isolated from 24 phage clones (Messing, 1983, ibid.) and the DNA sequence at the 5' end of the bioA gene was analysed by the method of Sanger et al. (1977; ibid.). The phage clone M13bio18/13 in which the wild-type promoter in front of the bioA gene is deleted and which simultaneously has a SalI cleavage site 26 bp upstream from the bioA gene was obtained in this way (FIG. 2).

1.4.4. Construction of M13bioDA

To arrange the bioD and bioA genes in a transcription unit, 5 $\mu$g of the plasmid pBO6 (FIG. 2) were cut with SphI and SalI. The resulting 0.97 kb-long DNA fragment which contains the bioD gene and 72 bp of the DNA downstream of the bioD gene up to the SalI end was isolated. 2 $\mu$g of M13bio18/13 were likewise cut with SphI and SalI. The DNA fragments were ligated with T4 DNA ligase, and *E. coli* JM109 was transformed. Double-stranded phage DNA was isolated from 24 recombinant clones and characterized via restriction analysis. The clone M13bioDA in which the bioD and bioA genes are a distance of 98 bp apart was obtained in this way (FIG. 2).

1.4.5 Construction of pBO30

To construct a transcription unit with the tac promoter in front of the bio genes, 5 $\mu$g of DNA from M13bioDA were cut with EcoRI, treated with Klenow polymerase to fill in protruding EcoRI ends as above and then cut with SnoI. The resulting 2.6 kb-long DNA fragment with the bioD, bioA and ORFI genes was isolated. 5 $\mu$g of the plasmid pBO28 (FIG. 2) were cut with SalI, treated with mung bean nuclease to eliminate protruding SalI ends and then likewise cut with SnoI. A 6.7 kb-long DNA fragment with vector DNA, tac promoter and bioBFC genes was isolated.

The isolated DNA fragments were ligated with T4 DNA ligase, and the biotin-auxotrophic strain *E. coli* SA291 (Cleary and Campbell, J. Bacteriol. 112:830–839; 1972) was transformed with this ligation mixture. Clones having a complete biotin operon in the plasmid were selected by plating out on NA plates containing 20 $\mu$g/ml Cm and 8 $\mu$g/ml avidin. Plasmids from such clones were checked by restriction analysis. Plasmid pBO30 which contains the bioB, bioF, bioC, bioD and bioA genes and the ORFI gene together with the tac promoter in a transcription unit was obtained in this way (FIG. 2).

1.5 Construction of plasmids with improved expression of the bio genes 1.5.1. Construction of pBO30A-9 and pBO30A-15

The DAPA aminotransferase encoded by the bioA gene was expressed considerably more weakly than the other enzymes for biotin synthesis in minicells of *E. coli* DS410 (Dougan and Sheratt, Mol. Gen. Genet. 151:151–160; 1977) with the plasmid pBO30. In an attempt to improve the expression of the bioA gene, the distance between the bioD gene and the bioA gene was shortened with exonuclease Bal31 in order to delete possible interfering sequences such as "stem-loop" structures. For this purpose, 25 $\mu$g of pBO30 were cut with SalI and then treated with exonuclease Bal31 and with Klenow polymerase as described above. The SalI cleavage site was regenerated by ligation to a synthetic oligonucleotide with the sequence 5'-CGTCGACG-3', a SalI linker. The DNA was then cut with SalI and SnoI, and the bioD fragments truncated at the 3' end and with a length of about 640 bp were isolated. These fragments were ligated to a fragment 8.25 kb in size from pBO30 which it was possible, after cutting this plasmid with SalI and SnoI, to isolate and which contains the unchanged bioA gene.

The biotin-auxotrophic strain *E. coli* SA291 was transformed with the above ligation mixture in order then to select clones with intact bioD gene on NA plates containing 60 $\mu$g/ml Cm and 5 $\mu$g/ml avidin. 26 such clones were obtained and were examined by restriction analysis. 8 of these clones with obvious truncation of the region upstream of the SalI site were characterized in detail by DNA sequence analysis. In five of these clones about 20 to 45 bp of the DNA between the bioD gene and the bioA gene were deleted as desired. In *E. coli* minicells, these clones in fact increased the expression of the bioA gene by a factor of 2 compared with pBO30. One example of a plasmid with expression improved in this way is the plasmid pBO30A-9 obtained in this way (FIG. 3).

Surprisingly, three other plasmids in which 70 to 90 bp of the DNA between the bioD gene and the bioA gene were deleted were isolated. The deletions thus extended into the bioD structural gene. The result of this was (i) a different COOH terminus of the DTB synthetase in each case without a large change in enzyme activity and (ii) an overlap of the modified bioD genes with the bioA reading frame. In this way, for example, plasmid pBO30A-15 with the bioD gene mutant bioDI5 was obtained (FIGS. 3, 5 and 6). In *E. coli* minicells with pBO30A-15, bioA expression is increased by a factor of 4 compared with pBO30.

Figure 3:
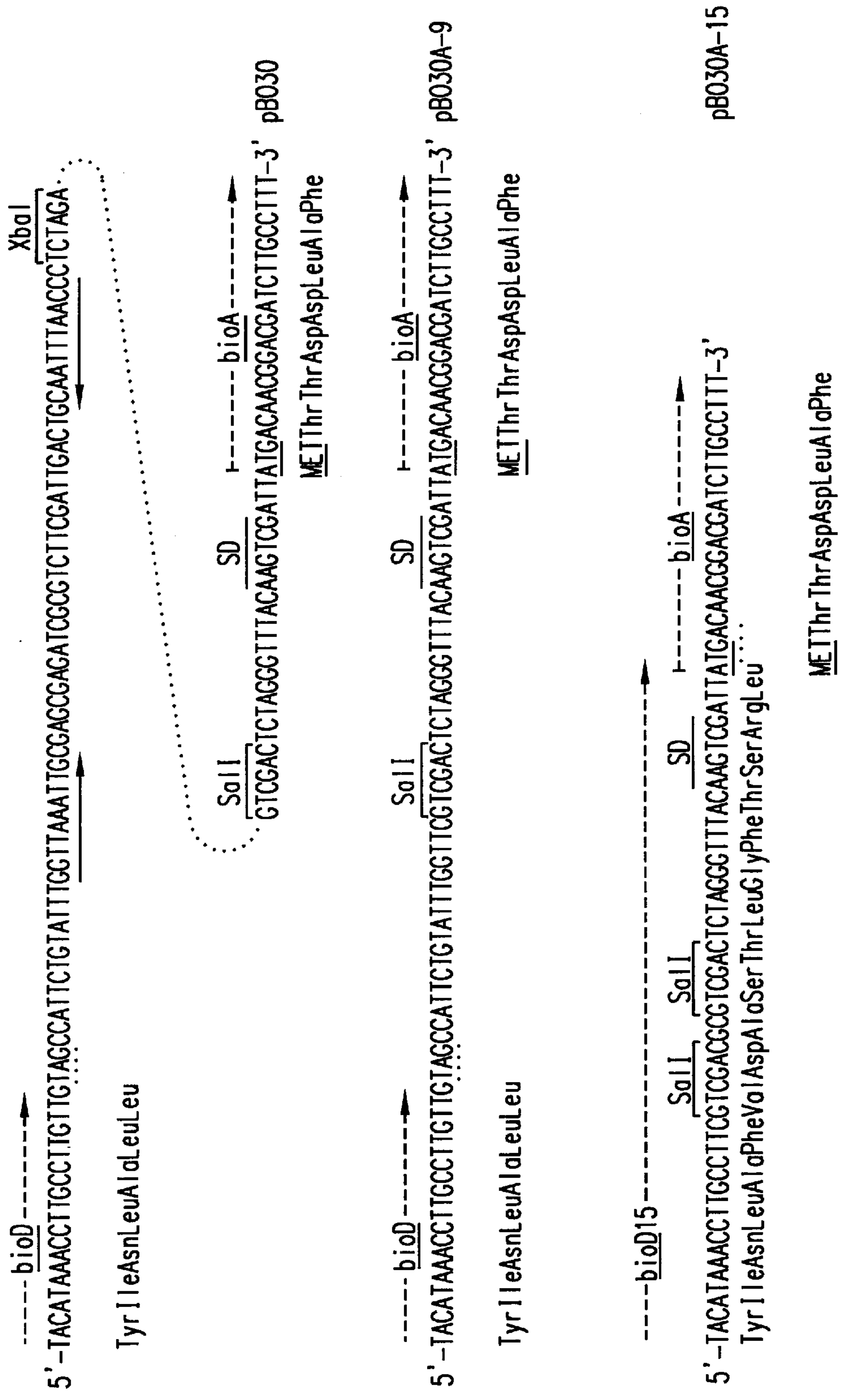
FIG. 3 shows the DNA sequence of the plasmids pBO30, pBO30A-9 and pBO30A-15 for the region of the 3' end of the bioD gene and of the 5' end of the bioA gene (dashed arrow; the bioA start codon is underlined, the bioD stop codon is shown dotted) together with the restriction cleavage sites which are relevant for plasmid construction, and the Shine-Dalgarno (SD) sequence of the bioA gene. Potential "stem-loop" structures are identified by full arrows.

The DNA sequences of the bioDA region and the amino-acid sequences, derived therefrom, of the plasmids pBO30, pBO30A-9 and pBO30A-15 are depicted in FIG. 3 (Seq ID No: 9–16).

1.5.2 Construction of plasmids with improved ribosome binding site in front of the bioB gene To improve translation of the bioB gene, whose expression in pBO30 is distinctly weaker than, for example, that of the bioD gene, the sequence which is upstream of the bioB gene in pBO30 and which comprises the tac promoter and a ribosome binding site which is present in the cloned tac promoter fragment was modified. For this purpose, synthetic, so-called "mixed" oligonucleotides with variable sequences were placed in front of the bioB gene. For simple selection of favourable ribosome binding sites, a test plasmid with a translational bioB::lacZ gene fusion, pbioB::lacZ-2, was used. pbioB::lacZ-2 is identical in the vector part, in the tac promoter with the ribosome binding site and in the 5' end of the bioB gene to the plasmid pBO22 (FIG. 2). However, the 3' end of the bioB gene and the remaining bio genes have been deleted at an NruI cleavage site after nucleotide 326 of the bioB structural gene, and the lacZ gene of *E. coli* (Casadaban et al., Methods Enzymol. 100:293–308; 1983) has been incorporated in such a way that bioB and lacZ were fused in the correct reading frame for expression of a bioB::lacZ fusion protein, and that the NruI cleavage site has been regenerated.

Figure 4A:
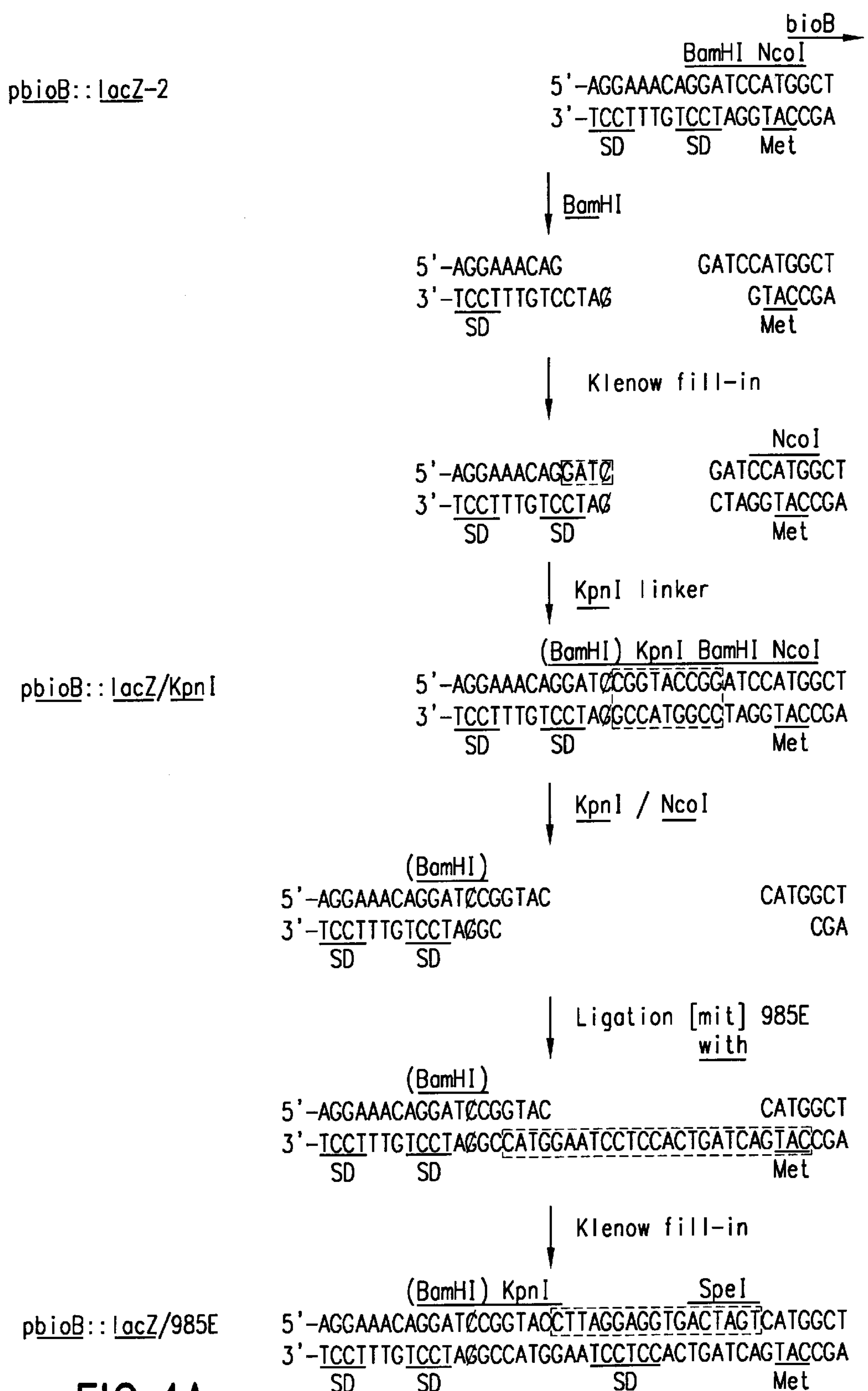
FIGS. 4A and 4B show the steps for modifying the sequence upstream of the bioB gene starting from plasmid pbioB::lacZ-2 for constructing improved ribosome binding sites indicating the restriction cleavage sites used, the particular Shine-Dalgarno sequences (SD) and the bioB start codon (Met). The sequences upstream of the bioB gene and the 5' terminus of the bioB gene are depicted. The dashed lines identify the inserted oligonucleotide 985E. Nucleotides which are crossed out ought theoretically to be present but are missing in plasmid pbioB::lacZ/985E and the plasmids pbioB::lacZ/9 and pbioB::lacZ/16 derived therefrom, which results in loss of a BamHI site (BamHI). "Fill-in": filling in with Klenow polymerase.
Figure 4B:
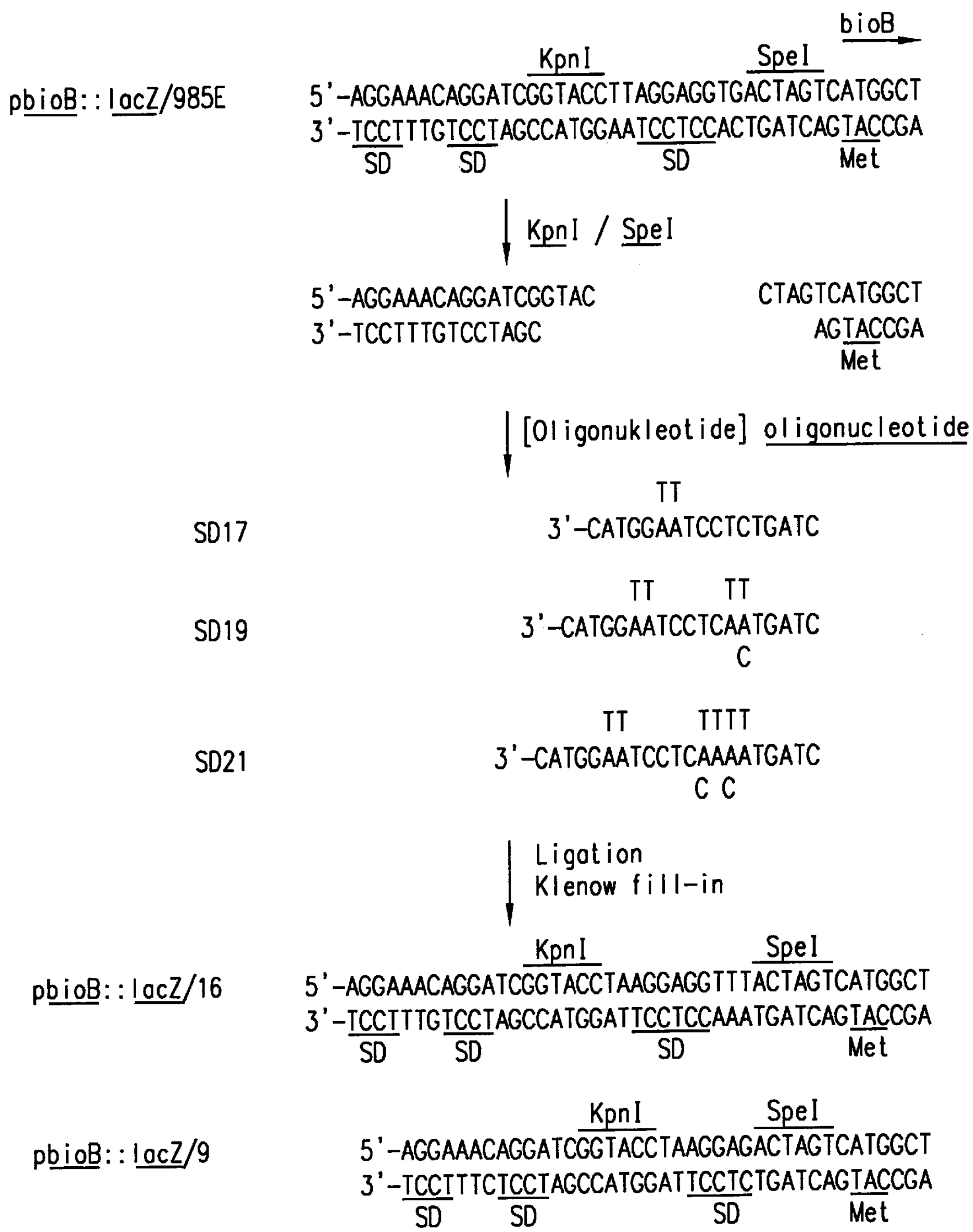

The oligonucleotide 985E with the sequence 5'-CATGGAATCCTCCACTGATCAGTAC-3' was inserted in front of the bioB gene in the plasmid pbioB::lacZ-2 in several steps (FIG. 4). For this purpose, pbioB::lacZ-2 was initially cleaved with BamHI and then the protruding BamHI ends were filled in as described with Klenow polymerase. During these steps there was evidently non-specific deletion of a guanine residue (G), which resulted in loss of a BamHI cleavage site in the subsequent plasmids. After insertion of a KpnI linker, *E. coli* XL1-Blue (Bullock et al., Biotechniques 5:376–379; 1987) was transformed with the ligation mixture, and the plasmid pbioB::lacZ/KpnI was isolated. This plasmid was partially cut with NcoI and then subsequently cut with KpnI. After ligation to the oligonucleotide 985E, the second DNA strand was filled in with Klenow polymerase. It was possible to isolate the plasmid pbioB::lacZ/985E after transformation of *E. coli* XL1-Blue and selection on NA plates containing 20 $\mu$g/ml Cm, 30 $\mu$g/ml X-Gal and 0.5 mM IPTG (isopropyl thiogalactoside) (FIG. 4). Plasmid pbioB::lacZ/985E was further modified by cutting out the ribosome binding site by restriction with KpnI and SPeI and replacing it by three different mixed oligonucleotides, SD17, SD19 and SD21 (FIG. 4). After ligation to these oligonucleotides, the gap in the second DNA strand was closed by incubation with Klenow polymerase. *E. coli* XL1-Blue bacterial cells were transformed with this DNA and plated as above on NA plates containing 20 μg/ml Cm, 30 μg/ml X-Gal and 0.5 mM IPTG. 20 clones with good expression of the bioB::lacZ fusion protein, which formed dark blue colonies on this medium, were selected, and the β-galactosidase activity of these clones was measured by an enzyme assay as described by Miller (Experiments in Molecular Genetics, Cold Spring Harbor Laboratory, Cold Spring Harbor, N.Y., pages 352–355; 1972). For this purpose, the *E. coli* strains with bio::lacZ plasmids had previously been grown in liquid culture to an optical density at 600 nm ($OD_{600}$) of about 0.5.

The highest β-galactosidase activity was shown by the plasmids pbioB::lacZ/985E, pbioB::lacZ/16 and pbioB::lacZ/9 (FIG. 4) in which the β-galactosidase activity was increased by a factor of 2.1, 3.4 and 5.9, respectively, compared with pbioB::lacZ-2. The DNA sequence of the optimized ribosome binding sites for the bioB gene in these plasmids was determined by the method of Sanger et al. (1977, ibid.).

To incorporate the optimized ribosome binding sites in a transcription unit with the bio genes, in each case 5 μg of the plasmids pbioB::lacZ/985E, pbioB::lacZ/16 or pbioB::lacZ/9 were cut with ClaI and NruI and an approximately 550 bp-long DNA fragment with the tac promoter, the particular ribosome binding site and the 5' end of the bioB gene was isolated. At the same time, 5 μg of the plasmid pBO30ΔA (FIG. 5) was cut with ClaI and NruI, and a 7.7 kb-long DNA fragment was isolated. In pBO30ΔA, which is derived from pBO30, a SalI/BamHI fragment with most of the bioA gene and an interfering NruI cleavage site is deleted (FIG. 5). The two fragments were ligated, and clones with recombinant plasmids were isolated. The plasmids pBO30ΔA/9, pBO30ΔA/16 and pBO30ΔA/985 were obtained in this way. FIG. 5 shows a construction of this type in the example of pBO30ΔA/9 with the ribosome binding site from pbioB::lacZ/9.

2 μg of each of the plasmids pBO30ΔA/9, pBO30ΔA/16 and pBO30ΔA/985E were cut with SnoI and KpnI, employing KpnI in a small amount for only partial cutting. In each case 6.6 kb-long DNA fragments which contained the vector DNA, the tac promoter, the bioB gene with the improved ribosome binding site and the bioFC genes were then isolated. The plasmid pBO30A-15 (4 μg) was likewise cut with SnoI and NcoI, and a 2.8 kb fragment with the bioDA-ORFI genes was isolated. The isolated fragments were ligated, and *E. coli* RR28 was transformed with the ligation mixture. Recombinant plasmids with a complete biotin operon were identified by restriction analysis. The plasmids pBO30A-15/9, pBO30A-15/16 and pBO30A-15/985E were obtained in this way. These all contain the optimized bioDA region from pBO30A-15 with the corresponding optimized ribosome binding sites from the plasmids pbioB::lacZ/9, pbioB::lacZ/16 and pbioB::lacZ/985E respectively. The genetic control elements in these plasmids, namely the combination of tac promoter and optimized ribosome binding site which are directly linked to the bioB gene and bring about its efficient expression, have the following sequences:

```
pBO30A-15/985E (seq ID No: 17)
5'-AAGCTTACTC CCCATCCCCC TGTTGACAAT TAATCATCGG CTCGTATAAT GTGTGGAATT
   GTGAGCGGAT AACAATTTCA CACAGGAAAC AGGATCGGTA CCTTAGGAGG TGACTAGTC-3'

pBO30A-15/16 (seq ID No: 18)
5'-AAGCTTACTC CCCATCCCCC TGTTGACAAT TAATCATCGG CTCGTATAAT GTGTGGAATT
   GTGAGCGGAT AACAATTTCA CACAGGAAAC AGGATCGGTA CCTAAGGAGG TTTACTAGTC-3'

pBO30A-15/9 (seq ID No: 19)
5'-AAGCTTACTC CCCATCCCCC TGTTGACAAT TAATCATCGG CTCGTATAAT GTGTGGAATT
   GTGAGCGGAT AACAATTTCA CACAGGAAAC AGGATCGGTA CCTAAGGAGA CTAGTC-3'
```

FIG. 5 shows the construction of plasmids which contain the bioB, bioF, bioC, bioD and bioA genes together with an optimized ribosome binding site in the example of the construction of pBO30A-15/9.

The complete transcription unit of the bio genes in pBO30A-15/9 was sequenced. The sequence and the gene products derived therefrom are depicted in FIG. 6 (Seq ID No: 1–8).

1.6 Construction of pBO30A-9ΔorfI

2 μg of the plasmid pBO30ΔA/9 were cut with SnoI and KpnI as above, and the 6.6 kb-long DNA fragment was isolated. 4 μg of the plasmid pBO30A-15 were cut with SspI. Ligation of the resulting linear DNA with a KpnI linker of the sequence 5'-CGGTACCG-3' led to insertion of a new KpnI site downstream of the bioA gene. After cutting with SnoI, a 2.1 kb fragment with the bioDA genes was isolated. The isolated DNA fragments were ligated, and *E. coli* RR28 was transformed with the ligation mixture. Recombinant plasmids with the bioBFCDA genes were identified by restriction analysis. pBO30A-15/9ΔorfI with a deletion of the ORFI gene was obtained in this way (FIG. 5).

1.7 Construction of plasmid pB047

5 μg of the plasmid pBO30A-15/9 were cut with the restriction enzymes XbaI and EcoRI. The resulting restriction fragment 5.8 kb in size with the tac promoter and the biotin operon was isolated and subsequently ligated to the "broad-host range" plasmid pRK290X (Alvarez-Morales et al., Nucl. Acid. Res. 14, 4207–4227, 1986; modified by deletion of an XhoI restriction site and insertion of an XbaI site at the same position), which was likewise cut with XbaI and EcoRI. The ligation mixture was used to transform *E. coli* S17-1 (Simon et al., Biotechnology 1:784–791; 1983). Recombinant plasmids were characterized by restriction analysis; plasmid pBO47 which contains the biotin operon integrated into pRK290X was obtained in this way.

The plasmid pBO47 was transferred into the bacterial strains Rhizobium/Agrobacterium sp. EK4, *Pseudomonas mondocina, Pseudomonas aeruginosa* PA01 (Holloway, J. Gen. Microbiol. 13:572–581; 1955) and *Acinetobacter calcoaceticus* DSM 588 by conjugation with the strain *E. coli* S17-1/pBO47.

1.8 Construction of pBO74ΔB

Construction of plasmid pBO74ΔB with a deletion of the bioB gene took place starting from plasmid pBO74-13 (FIG. 7). Plasmid pBO74-13 consists of the same DNA building blocks as pBO30 (FIG. 2). The sequence of the bio genes inside the plasmid pBO74-13 is, however, different.

5 μg of the plasmid pBO74-13 were cut with SmaI. After extraction with phenol/chloroform, the plasmid DNA was cut with SphI, and a 6 kb fragment containing the vector DNA, the tac promoter and the bioA-ORFI and bioCD genes was isolated. 18 μg of the plasmid pBO3 (FIG. 2) were cut with SspI and SphI, and a 1.66 kb fragment with the bioF gene and part of the bioC gene was isolated. The isolated fragments were ligated together and *E. coli* RR28 was transformed with the ligation mixture. Recombinant plasmids were analysed by restriction analysis. Plasmid pBO74ΔB which differs from plasmid pBO74-13 by deletion of the bioB gene was obtained in this way (FIG. 7)

EXAMPLE 2

In vivo biotin fermentations 2.1 In vivo biotin fermentation with *Escherichia coli* producer strains Cells of the *E. coli* strain XL1-Blue with pBO30A-15/9 (DSM 7246) were cultured using a 20 l MBR fermenter in glycerol minimal medium (3% glycerol at the start of the culture) in a fed batch method at 37° C. for 30 h until the optical density at 650 nm ($OD_{650}$) was 20. The presence of the plasmid pBO30A-15/9 was ensured by adding chloramphenicol (50 μg/ml) in the preculture (3 l of glycerol minimal medium) and the batch phase of the fermentation. It was just as practicable to use other carbon sources such as glucose or succinate (0.4% at the start of the batch fermentation phase). The metabolic activity of the cells was followed by means of their specific oxygen uptake rate. The production of biotin during the fermentation was followed by titration of the biotin levels in the fermenter medium using a bioassay with *Lactobacillus plantarum* (E. DeMoll and W. Shive, Anal. Chem. 158:55–58, 1986).

The carbon source, in this case a 50% strength glycerol solution in deionized water, was fed in at a variable inflow rate adapted to the particular growth of biomass. An empirical value of 2 g of glycerol per liter of culture for an OD increase from OD 1 to OD 2 was used as basis for the "feed" rate of glycerol.

The pH of the fermenter was controlled automatically at pH 7 by pumping in 40% strength $H_3PO_4$ or 25% strength $NH_3$. The aeration was controlled by blowing in 10–25 L(STP)/min of air and rotating the stirrer at 300–700 rpm in accordance with the particular growth of biomass. An oxygen saturation between 15 and 40% was aimed at. The oxygen content and the $CO_2$ content of the exit air were measured paramagnetically and using infra-red respectively. The temperature of the fermenter was controlled at 37° C. At 37° C., the culture grew with a doubling time of 2.5 hours up to an $OD_{650}$ of 20 and then became stationary.

During the fermentation, 35 mg/l D(+)-biotin accumulated within 25 hours. In *E. coli* strains, worthwhile biotin synthesis can be achieved only in growing cultures.

Further suitable producer strains have proved to be *E. coli* ED8767 (N. E. Murray et al., Mol. Gen. Genet. 150:53–61; 1975) with pBO30A-15/9 (DSM 8554) or *E. coli* BM4062 (D. F. Barker and A. M. Campbell, J. Bacteriol. 143:789–800; 1980) with pBO30A-15/9 (DSM 7247);

In a similar way the plasmids pBO3, pBO30 and pBO30A-15/9ΔORFI were tested and the biotin productivity was determined. The following Table I shows the great improvement in biotin productivity of strains having the plasmids pBO30, pBO30A-15/9 and pBO30A-15/9ΔORFI, which have the bio genes in a transcription unit, compared with *E. coli* S17-1 (wild-type, biotin genes on the chromosome) and *E. coli* S17-1/pBO3 (biotin genes on the plasmid but divergent transcription as in the wild-type operon). The experiments furthermore show that the absence of the ORFI gene has no effect on biotin productivity.

TABLE I

| Strain | Biotin productivity pmol/min × $10^9$ cells |
|---|---|
| *E. coli* S17-1 | 0.01–0.02 |
| *E. coli* S17-1/pBO3 | 0.02–0.04 |
| *E. coli* BM 4062/pBO30 | 3.0–5.0 |
| *E. coli* XL1 Blue/pBO30A-15/9 | 10.0–20.0 |
| *E. coli* BM 4062/pBO30A-15/9ΔORFI | 10.0–20.0 |

| Glycerol minimal batch medium (in deionized $H_2O$) | |
|---|---|
| Glycerol | 30 g/l |
| $MgCl_2 \times 6H_2O$ | 0.8 g/l |
| $CaCl_2$ | 0.16 g/l |
| $(NH_4)_2SO_4$ | 2.0 g/l |
| Trace elements SLF[a)] | 1.0 ml/l |
| Fe-EDTA[b] | 1.5 ml/l |
| PPG-2000 | 0.1 g/l |
| $KH_2PO_4$ | 1 g/l |
| $K_2HPO_4$ | 1 g/l |
| $Na_2HPO_4$ | 1 g/l |
| Thiamine | 1 g/l |
| Chloramphenicol | 50 mg/l |
| IPTG | 0.5 mM |

| a) Stock solution of trace elements SLF (in deionized $H_2O$) | |
|---|---|
| KOH | 15 g/l |
| $EDTA\text{-}Na_2 \times 2H_2O$ | 100 g/l |
| $ZnSO_4 \times 7H_2O$ | 9 g/l |
| $MnCl_2 \times 4H_2O$ | 4 g/l |
| $H_3BO_3$ | 2.7 g/l |
| $CoCl_2 \times 6H_2O$ | 1.8 g/l |
| $CuCl_2 \times 2H_2O$ | 1.5 g/l |
| $NiCl_2 \times 6H_2O$ | 0.18 g/l |
| $Na_2MoO_4 \times 2H_2O$ | 0.2 g/l |

| b) Stock solution of Fe-EDTA (in deionized $H_2O$) | |
|---|---|
| EDTA $Na_2 \times 2H_2O$ | 50 g/l |
| $FeSO_4 \times 7H_2O$ | 20 g/l |
| KOH | 10 g/l |

Antibiotic supplements: (final concentrations)

100 μg/ml ampicillin (sodium salt, Fluka) and 50 μg/ml chloramphenicol (Fluka)

2.2 In vivo biotin fermentation with the Agrobacterium/Rhizobium producer strain HK4/pBO47

Cells of the biotin auxotrophic strain Agrobacterium/Rhizobium sp HK4 with the biotin producer plasmid pBO47 (DSM 8555) were cultured in a 2 l MBR fermenter in an L-glutamic acid/betaine minimal medium in a fed-batch method at 30° C. until the $OD_{650}$ was 70. HK4/pBO47 is characterized by a remarkably stable biotin synthesis rate even when growth is extremely slow ("maintenance growth"). For this reason, in this experiment the cultivation of the biomass was followed by a long maintenance phase (500 hours) with a greatly reduced carbon "feed".

After the exponential growth phase and after an $OD_{650}$ of 12 had been reached, a glucose/betaine "feed" (360 g/l glucose plus 103 g/l betaine dissolved in deionized water) was fed in at a slow rate (1.5 ml/hour) in order to allow long-lasting slow growth or "maintenance growth". At the 150-hour timepoint, $Fe^{2+}$ gluconate was then fed into the fermenter to a final concentration of 100 mg/l. At the 200, 360 and 550-hour timepoints, 10 ml of salt solution and 1.36 ml of standard vitamin solution were then fed in.

The pH of the fermenter was controlled automatically at 7 by pumping in 85% strength phosphoric acid or 3 M potassium hydroxide solution. The aeration was controlled by blowing in 1–3 L(STP)/min air and rotating the stirrer at 300–1,000 rpm in accordance with the particular growth of biomass so that an oxygen tension of 1–4 mg/l was ensured. The temperature of the fermenter was controlled at 30° C. The culture grew in the exponential growth phase with a doubling time of 5.6 hours and in the phase with severely limited "feed" with a doubling time of 300 hours and then changed over to "maintenance growth".

At the start of the fermentation, after 200 hours and after 415 hours, diaminopelargonic acid was added to the culture (DAPA; twice to a final concentration of 200 μg/ml, finally to a final concentration of 100 μg/ml). HK4 itself is biotin-auxotrophic. The strain was able to produce dethiobiotin from the biotin precursor DAPA and convert it finally into D(+)-biotin in high yield. 110 mg/l D(+)-biotin accumulated. The remarkable fact here is that this synthesis was predominantly performed by non-growing cells.

Glutamic acid/betaine minimal medium

The following were dissolved in or added to 1.25 liters of deionized water:

31.25 g of L-glutamic acid monosodium salt×$H_2O$
12.5 g of betaine
0.2 g of $CaCl_2$
1.0 g of $MgCl_2$×6$H_2O$
1.25 g of $K_2SO_4$
1.25 ml of trace elements SLF (Example 2.1)
1.87 ml of Fe-EDTA (Example 2.1)
0.25 ml of tetracycline (10 mg/ml in 70% ethanol)

Salt solution 0.03 g of $CaCl_2$
0.16 g of $MgCl_2$×6$H_2O$
0.2 g of $K_2SO_4$
200 μl of SLF (Example 2.1)
300 μl of HCl conc.
(dissolved in 10 ml of deionized $H_2O$)

Standard vitamin solution (in deionized $H_2O$)

10 mg/l pyridoxal hydrochloride
5 mg/l riboflavin
5 mg/l nicotinamide
5 mg/l thiamine hydrochloride
2 mg/l biotin
5 mg/l pantothenic acid
5 mg/l 4-aminobenzoic acid
2 mg/l folic acid
5 mg/l vitamin B12

EXAMPLE 3

Production of biotin starting from dethiobiotin (measurement of the biotin synthase reaction in vitro)

3.1 Production of *E. coli* cell extracts

In each case a cell extract of *E. coli* XL1-Blue (DSM 7246) with the plasmid pBO30A-15/9 (extract Z) and a cell extract of *E. coli* XL1-Blue with the plasmid pBO74ΔB (DSM 7245; extract W) was produced. For this purpose, the microorganism cells were cultured at 37° C. in a volume of 800 1 with an $OD_{600}$ of 2 in a medium containing 20 g/l nutrient broth, 5 g/l yeast extract and 20 mg/l Cm. The cells were harvested by filtration and subsequently centrifuged at 5,000×g for 15 min.

To produce the cell-free extract, the cells were washed with 100 mM HEPES buffer (pH 7.5), then resuspended in the same buffer to adjust to an $OD_{600}$ of approximately 1,000 and then treated with DNAse. The cells were subsequently disrupted using a continuous cell homogenizer at 100,000 Pa. The homogenate was centrifuged at 20,000×g for 30 min, and the resulting supernatant was stored at −80° C. It was then possible for extract Z to be used to measure (assay) the biotin synthase reaction either directly or only after purification by gel filtration on a column loaded with Sephadex G25M PD-10 (Pharmacia, column volume: 9.1 ml). Extract W was either employed directly for assay of the biotin synthase reaction or fractionated as in Example 3.3.

3.2 In vitro assay of the biotin synthase reaction (standard assay)

The in vitro assay investigated either the reaction of $^{14}C$-labelled dethiobiotin (0.1 μCi; 1.95 nmol) to $^{14}C$-labelled biotin or the reaction of unlabelled dethiobiotin with $^{35}S$-labelled cysteine (20 μCi; 1.32 nmol) to $^{35}S$-labelled biotin with the enzyme biotin synthase. Determination of the $^{14}C$-biotin or $^{35}S$-biotin formed during this was easily possible, after extraction, by quantitative HPLC, on an "on-line" radiochemical detector or semiquantitatively by thin-layer chromatography and subsequent application of an X-ray film by autoradiography.

A typical standard assay was composed of the cell-free extract Z or W, of labelled or unlabelled dethiobiotin, depending on the reaction, or of the protein fractions purified therefrom (Examples 3.7–3.9), singly or in combination with one another, and/or of customary cofactors such as SAM (92 μM), $Fe^{2+}$ gluconate (200 μM), NADPH (100 μM), TPP (100 μM), DTT (1 mM) and/or of a combination of amino acids. The protein fractions to be assayed, cofactors or amino acids were added in a final volume of 250 μl. Incubation takes place at between 4 and 50° C. After incubation at 37° C. for one hour, the reaction was stopped by adding 12% by weight trichloroacetic acid (TCA) in water. The precipitated protein was centrifuged and the supernatant was loaded onto a $C_{18}$ "solid phase" extraction column (MACHEREY-NAGEL, 100 mg) which had been equilibrated with methanol (1 ml), water (1 ml) and with acetic acid (1% by volume) in water. This column was subsequently washed with 1 ml of 1% strength acetic acid and 1 ml of water in order then to elute biotin and dethiobiotin with 0.5 ml of methanol. The resulting samples were dried in vacuo and then resuspended in 30 μl of HPLC buffer A (25 mM $KH_2PO_4$, 5 mM tetrabutylammonium chloride, pH 3.4) in order then to inject 25 μl into the HPLC for the quantitative analysis. The HPLC conditions were as follows: Shandon Hypersil BDS $C_{18}$ column (particle size: 5 μm, column size 10 mm×2.0 mm), flow rate 0.35 ml/min, temperature 40° C., eluent: HPLC buffer A with 10% by volume acetonitrile.

After the eluate stream had been mixed with a scintillation measuring solution (Zinsser Quickszint Flow 303; flow rate: 1.25 ml/min), either unreacted $^{14}C$-dethiobiotin and $^{14}C$-biotin formed or $^{35}S$-biotin formed was detected and quantified ("on-line" radioactivity detector: Berthold).

Alternatively, the samples were analysed semi-quantitatively by thin-layer chromatography and autoradiography. For this purpose, the samples were resuspended in 20 μl of a mixture composed of 10% acetic acid, 65% methanol and 25% water, and 2.5 μl was applied to a silica gel "high performance" TLC plate (E. Merck, Darmstadt). The plate was developed with a mobile phase composed of chloroform (17 ml), methanol (3 ml) and formic acid (0.2 ml). After the chromatography, the plate was dried and then an X-ray film was applied overnight.

3.3 Biotin synthase reaction in the presence of amino acids

When the desalted cell-free extract Z was incubated with dethiobiotin in accordance with Example 3.2 and with the cofactors SAM, TPP, NADPH and $Fe^{2+}$ gluconate, no conversion of dethiobiotin to biotin was observed. If cysteine (332 μM) and asparagine (15 mM) or cysteine and aspartate (15 mM) or cysteine and glutamine (15 mM) or cysteine and serine (15 mM) with the cofactors specified in Example 3.4 was added to this cell-free extract, biotin production was detectable.

TABLE II

| Composition of the assay | pmol of biotin produced |
|---|---|
| Extract Z[1] | 0 |
| " + cofactors[2] | 0 |
| " + amino acids[3] | 0 |
| " + cofactors[2] + amino acids[3] | 780 |

[1]desalted
[2]cofactors: SAM, $Fe^{2+}$, TPP, NADPH
[3]Cys + Asn or Cys + Asp or Cys + Gln or Cys + Ser 3.4 Biotin synthase reaction in the presence of one or more customary cofactors When the same desalted cell extract as described in Example 3.3 was incubated with L-cysteine, asparagine, dethiobiotin, SAM, TPP, NADPH and $Fe^{2+}$ gluconate, dethiobiotin was converted into biotin. In order to test the effect of these cofactors on the biotin synthase reaction, they were employed singly and in combination with one another. Only a combination of all these cofactors showed biotin synthase activity. No biotin synthase activity was measurable in the absence of one cofactor, that is to say all cofactors are necessary for biotin synthase activity (Example 3.3, Table II).

3.5 Purification of biotin synthase

To prove that, in addition to biotin synthase, several proteins are responsible for converting dethiobiotin to biotin, initially the cell-free extract Z was subjected to an ammonium sulphate fractionation. This was carried out with a saturation of 25% ammonium sulphate by stirring at 4° C. for 30 min. The mixture was then centrifuged at 10,000×g for 30 min, and the resulting pellet was discarded. The resulting supernatant was saturated with 70% ammonium sulphate, whereupon the biotin synthase was precipitated. The precipitate was resuspended in a small volume of 100 mM HEPES buffer (pH 7.5), desalted (Sephadex G25M PD-10) and then purified by anion exchange chromatography (Q-Sepharose Fast-Flow, Pharmacia) with a continuous gradient of 100 mM–1 M HEPES buffer (pH 7.5). The fractions with biotin synthase activity were concentrated (Amicon ultrafiltration cell, YM-10 membrane), desalted as already described and subsequently rechromatographed on a Q-Sepharose "Hi-Load" anion exchange chromatography column (Pharmacia; 20 mM Tris buffer (pH 7.5) containing 1 m DTT and a 0–1 M NaCl gradient). The fractions with high biotin synthase activity were combined, concentrated and desalted. In these fractions the biotin synthase was no longer contaminated with other proteins necessary for the biotin synthase activity.

In order to measure the biotin synthase activity during the purification steps it was necessary to add extract W to the assay mixture (Example 3.2). Accordingly, other proteins besides biotin synthase are responsible for the conversion of dethiobiotin to biotin.

3.6 Fractionation of proteins from extract W

For this purpose, the extract was precipitated consecutively with 45% and 55% saturation of ammonium sulphate. After addition of ammonium sulphate, the mixture was stirred at 4° C. for 30 min and subsequently centrifuged at 10,000×g for 30 min. The precipitate obtained with 45% saturation of ammonium sulphate was resuspended in 100 mM HEPES buffer (pH 7.5). Subsequently, aliquots of the 45% precipitate, the 55% precipitate and the 55% supernatant were removed and desalted (Sephadex G25M PD-10 column). The individual fractions were assayed both individually and in combination with one another as described in Example 3.2.

2 fractions necessary for biotin synthase were obtained. These fractions were:

- the precipitate from 45% saturation of ammonium sulphate
- the supernatant from 55% saturation of ammonium sulphate 3.7 Purification and identification of flavodoxin The supernatant resulting after 55% saturation of ammonium sulphate from extract W (Example 2.2) was desalted (Sephadex G25M PD-10 column) and subsequently loaded onto an anion exchange chromatography column (Q-Sepharose Fast-Flow (Pharmacia)). This column had previously been equilibrated with 20 mM Tris buffer (pH 7.5) containing 1 mM DTT. The unbound material was removed by washing with this buffer. The proteins bound to the column were eluted with a continuous NaCl gradient (0–1 M). The eluted protein fractions were combined, concentrated (Amicon ultrafiltration cell, YM-10 membrane), desalted (Sephadex G25M PD-10) and subsequently purified on a Mono Q anion exchange chromatography column which had been equilibrated with 20 mM Tris buffer (pH 7.0, containing 1 mM DTT). The purified fractions were then examined by SDS PAGE.

In order to identify the fractions which contain the protein sought during the purification steps, the biotin synthase assay system (Example 3.2) was carried out with purified biotin synthase, protein or proteins from the precipitate of the 45% ammonium sulphate precipitation, with amino acids (Example 3.3) and with low molecular weight cofactors (Example 3.4). Biotin synthase activity was measurable only in the fractions which contained the protein sought.

Subsequently, the amino-acid sequence of this protein was determined as follows. The protein was reduced with DTT in 6 M guanidine HCl buffer for 4 h. The resulting samples were carboxymethylated with iodoacetic acid and then dialysed against 0.1% ammonium bicarbonate for 48 h. The samples were dried and then digested with porcine trypsin in 7 M urea buffer, and the peptides were separated by "reverse phase" HPLC. It was possible to identify 2 peptides with DNA sequences corresponding to *E. coli* flavodoxin. It was possible to obtain homogeneous flavodoxin by these purification steps.

3.8 Purification and identification of ferredoxin (flavodoxin)-$NADP^+$ reductase Extract W was loaded onto an anion exchange chromatography column (Q-Sepharose FastFlow (Pharmacia)). This column had been equilibrated with 20 mM Tris buffer (pH 7.5) containing 1 mM TPP. The proteins bound to the column were eluted with a continuous NaCl gradient (0–1 M). The eluted protein fractions were combined and, as in Example 3.7, concentrated, desalted and loaded onto a Mono-Q anion exchange chromatography column. The proteins bound to this column were eluted with a continuous NaCl gradient (0–0.4 M in 20 mM Tris buffer). The combined eluted protein fractions (concentrated and desalted as already described) were subsequently loaded onto a Superose 12 Prep. gel filtration chromatography column (Pharmacia; equilibrated with 20 mM Tris buffer) and then onto a Sephacryl HR100 gel filtration column (Pharmacia; equilibrated with 20 mM Tris buffer). After elution with 20 mM Tris buffer it was possible to obtain another homogeneous protein (examined by SDS PAGE). The fractions containing this protein were identified in analogy to the assay system described in Example 3.7. Biotin synthase activity was measured only after addition of these fractions.

In order to determine the N-terminal amino-acid sequence of this protein, the purified protein was sequenced directly. The protein had an N-terminal amino-acid sequence corresponding to that of ferredoxin-(flavodoxin)-NADP$^+$ reductase. It was possible by these purification steps to obtain ferredoxin(flavodoxin)-NADP$^+$ reductase homogeneously.

3.9 Enrichment of one or more proteins responsible for the biotin synthase reaction The purified biotin synthase (Example 3.2) had no biotin synthase activity with purified flavodoxin plus ferredoxin (flavodoxin)-NADP$^+$ reductase and with the necessary cofactors, and with the amino acids. In order to achieve activity, another protein or proteins in the 45% ammonium sulphate fraction was sought.

This protein or these proteins were obtained from the cell-free extract W by ammonium sulphate precipitation at a saturation of 45%. The resulting protein pellet was resuspended in 20 mM Tris buffer, pH 7.5, containing 1 mM DTT and TPP (1 g/l) and subsequently desalted with a PD-10 column (Pharmacia). The desalted material was then loaded onto an anion exchange chromatography column (Q-Sepharose HP Hi-Load) which had previously been equilibrated with 20 mM Tris buffer, pH 7.5, containing 1 mM DTT and TPP (1 g/l). The protein fractions with the required activity were eluted with a continuous NaCl gradient (0 mM–600 mM). These protein fractions were subsequently purified further by gel filtration chromatography (Sephacryl HR-100 column, Pharmacia). The protein pellet obtained therefrom was resuspended in 100 mM HEPES buffer (pH 7.5) and then desalted as already described. A protein solution was obtained therefrom and was employed for the in vitro assay as described in Example 3.2.

3.10 Biotin synthase reaction in the presence of flavodoxin, ferredoxin(flavodoxin)-NADP$^+$ reductase, one or more proteins responsible for the biotin synthase reaction, one or more amino acids and the customary cofactors Flavodoxin, ferredoxin(flavodoxin)NADP$^+$ reductase and the protein or proteins responsible for the biotin synthase reaction were added to the cell-free extract Z. Addition of proteins, cofactors and amino acids brought about an increased biotin synthase activity (Table III).

TABLE III

| Composition of the assays | pmol of biotin produced |
|---|---|
| Extract Z with cofactors and amino acids | 390 |
| Extract Z + cofactors + amino acids + flavodoxin + ferredoxin (flavodoxin) -NADP$^+$ reductase + one or more of the proteins responsible for the biotin synthase reaction | 1,560 |

3.11 Biotin synthase reaction with purified biotin synthase in the presence of combinations of flavodoxin, ferrodoxin (flavodoxin)-NADP$^+$ reductase, one or more of the proteins responsible for the biotin synthase reaction, one or more amino acids and the customary cofactors In order to test the effect of these components on the biotin synthase reaction with purified biotin synthase, they were employed singly or in combination with one another. The cofactors were employed in the same amount as in Example 3.4, and the amino acids were employed as in Example 3.3. When all these components were present, dethiobiotin was completely converted to biotin with purified biotin synthase. No activity was measurable when one of these components was absent. Hence all these components are required for converting dethiobiotin to biotin (Table IV).

TABLE IV

| Composition of the assay | pmol of biotin produced |
|---|---|
| Purified biotin synthase | 0 |
| Purified biotin synthase + flavodoxin + ferredoxin (flavodoxin) NADP$^+$ reductase + one or more proteins responsible for the biotin synthase reaction + cofactors + amino acids | 800 |

What is claimed is:

1. A purified and isolated DNA molecule comprising biotin-biosynthesis structural genes bioB, bioF, bioC, bioD and bioA from an enteric bacterium that encode biotin biosynthetic enzymes, wherein the bioB, bioF, bioC, bioD and bioA structural genes are arranged in a single unidirectional transcription unit in said DNA molecule, and transcribed from a common promoter.

2. The DNA molecule according to claim 1, wherein the enteric bacterium is selected from the group consisting of the genera Escherichia, Salmonella and Citrobacter.

3. The DNA molecule according to claim 1, wherein the enteric bacterium is the species *Escherichia coli.*

4. The DNA molecule according to claim 1, wherein the common promoter is a tac promoter.

5. The DNA molecule according to claim 1, wherein the transcription unit has a gene-regulatory element which is operably linked to the bioB structural gene and which comprises the nucleotide of sequence SEQ ID No. 17.

```
AAGCTTACTC CCCATCCCCC TGTTGACAAT TAATCATCGG
CTCGTATAAT GTGTGGAATT GTGAGCGGAT AACAATTTCA
CACAGGAAAC AGGATCGGTA CCTTAGGAGG TGACTAGTC.
```

6. The DNA molecule according to claim 1, wherein the transcription unit has a gene-regulatory element which is operably linked to the bioB structural gene and which comprises the nucleotides numbered 1–120: of sequence SEQ ID NO. 18.

7. The DNA molecule according to claim 1, wherein the transcription unit has a gene-regulatory element which is operably linked to the bioB structural gene and which comprises the nucleotides numbered 1–116 of sequence SEQ ID NO. 19.

8. The DNA molecule of claim 1 wherein the structural genes bioB, bioF, bioC, bioD and bioA are arranged 5' to 3' in the order bioB, bioF, bioC, bioD and bioA.

9. The DNA molecule according to claim 1, wherein the bioD structural gene and the bioA structural gene are located consecutively in the transcription unit.

10. The DNA molecule according to claim 1, wherein the bioD and the bioA structural genes are apart by a distance of not more than 50 base pairs.

11. The DNA molecule according to claim 1, wherein bioD and bioA structural genes are arranged such that the 3'-terminus of the bioD structural gene contains a ribosome binding site for the bioA structural gene.

12. A plasmid containing the DNA molecule according to claim 1.

13. The plasmid according to claim 12 whereby the plasmid is pBO30A-15/9.

14. The plasmid according to claim 12 whereby the plasmid is pBO74ΔB.

15. A microorganism comprising the DNA molecule according to claim 1.

16. A microorganism comprising the plasmid according to claim 12.

17. A microorganism comprising the plasmid according to claim 13.

18. A microorganism comprising the plasmid according to claim 14.

19. The microorganism according to claim 17, wherein the microorganism is *E. coli* XL1-Blue as deposited in the depository Deutsche Sammlung für Mikroorganismen und Zellkulturen GmbH D-3300 Braunschweig, Mascheroderweg 1b and assigned accession number DSM 7246.

20. The microorganism according to claim 17, wherein the microorganism is *E. coli* BM4062 as deposited in the depository Deutsche Sammlung für Zellkulturen GmbH, D-3300 Braunschweig, Mascheroderweg 1b and assigned accession number DSM 7247.

21. The microorganism according to claim 17, wherein the microorganism is *E. coli* ED8767 as deposited in the depository Deutsche Sammlung für Mikroorganismen und Zellkulturen GmbH, D-3300 Braunschweig, Mascheroderweg 1b and assigned accession number DSM 8554.

22. The microorganism according to claim 18, wherein the microorganism is Agrobacterium/Rhizobium sp. HK4 as deposited in the depository Deutsche Sammlung für Mikroorganismen und Zellkulturen GmbH, D-3300 Braunschweig, Mascheroderweg 1b and assigned accession number DSM 8555.

23. A method for biotin synthesis comprising fermenting a metabolizable carbon source to biotin using the microorganism according to claim 15.

24. A method for biotin synthesis comprising fermenting a metabolizable carbon source to biotin using the microorganism according to claim 16.

25. A method for biotin synthesis comprising fermenting a metabolizable carbon source to biotin using the microorganism according to claim 17.

26. A method for biotin synthesis comprising fermenting a metabolizable carbon source to biotin using the microorganism according to claim 18.

27. A method for biotin synthesis comprising fermenting a metabolizable carbon source to biotin using the microorganism according to claim 19.

28. A method for biotin synthesis comprising fermenting a metabolizable carbon source to biotin using the microorganism according to claim 20.

29. A method for biotin synthesis comprising fermenting a metabolizable carbon source to biotin using the microorganism according to claim 21.

30. A method for biotin synthesis comprising fermenting a metabolizable carbon source to biotin using the microorganism according to claim 22.

* * * * *